(12) United States Patent
Denson et al.

(10) Patent No.: US 11,077,011 B2
(45) Date of Patent: Aug. 3, 2021

(54) COMPRESSION GARMENT COMPLIANCE

(71) Applicant: KPR U.S., LLC, Mansfield, MA (US)

(72) Inventors: Jesse Denson, Lincoln, RI (US); Scott Wudyka, Marlboro, MA (US); Paul Becker, Taunton, MA (US)

(73) Assignee: KPR U.S., LLC, Mansfield, MA (US)

( * ) Notice: Subject to any disclaimer, the term of this patent is extended or adjusted under 35 U.S.C. 154(b) by 774 days.

(21) Appl. No.: 15/290,026

(22) Filed: Oct. 11, 2016

(65) Prior Publication Data

US 2017/0100301 A1 Apr. 13, 2017

Related U.S. Application Data

(60) Provisional application No. 62/329,233, filed on Apr. 29, 2016, provisional application No. 62/239,566, (Continued)

(51) Int. Cl.
*A61H 9/00* (2006.01)
*A61B 5/00* (2006.01)
(Continued)

(52) U.S. Cl.
CPC ......... *A61H 9/0078* (2013.01); *A61B 5/4833* (2013.01); *A61F 5/012* (2013.01);
(Continued)

(58) Field of Classification Search
CPC ............ A61H 2230/00; A61H 2230/06; A61H 2230/065; A61H 31/00; A61H 9/00;
(Continued)

(56) References Cited

U.S. PATENT DOCUMENTS 3,866,604 A 2/1975 Curless et al.
4,016,868 A 4/1977 Allison
(Continued)

FOREIGN PATENT DOCUMENTS

CA 2211651 A1 8/1996
CN 201516113 U 6/2010
(Continued)

OTHER PUBLICATIONS

International Search Report and Written Opinion dated Feb. 17, 2017 in related International application PCT/US2016/056296, 12 pages.

(Continued)

*Primary Examiner* — Tu A Vo
*Assistant Examiner* — Alexander Morales
(74) *Attorney, Agent, or Firm* — Arent Fox LLP

(57) ABSTRACT

Determining whether a compression garment is worn by a wearer of the garment by analyzing a pressure signal waveform indicative of a fluid pressure in an inflatable and deflatable bladder of the compression garment. Variance detected in the pressure signal waveform during the analysis is indicative of a change in condition of the compression garment. In one aspect the change in condition is verified using confirmatory analysis. In another aspect, the variance is one of a pressure rise and a pressure impulse. In yet another aspect, the variance is an oscillating amplitude as a function of time representative of a pulse of the wearer.

22 Claims, 30 Drawing Sheets

Related U.S. Application Data filed on Oct. 9, 2015, provisional application No. 62/239,527, filed on Oct. 9, 2015, provisional application No. 62/239,493, filed on Oct. 9, 2015.

(51) Int. Cl.
*A61F 5/058* (2006.01)
*A61F 5/01* (2006.01)
*G01F 1/34* (2006.01)
*G01F 22/02* (2006.01)

(52) U.S. Cl.
CPC .............. *A61F 5/0585* (2013.01); *G01F 1/34* (2013.01); *A61H 2201/0184* (2013.01); *A61H 2201/164* (2013.01); *A61H 2201/165* (2013.01); *A61H 2201/5002* (2013.01); *A61H 2201/5007* (2013.01); *A61H 2201/5071* (2013.01); *A61H 2205/106* (2013.01); *A61H 2209/00* (2013.01); *A61H 2230/065* (2013.01); *A61H 2230/085* (2013.01); *G01F 22/02* (2013.01)

(58) Field of Classification Search
CPC .......... A61H 2201/01; A61H 2201/165; A61H 2201/50; A61H 2201/5058; A61F 5/012; A61F 5/05816; G01F 1/34; G01F 22/02; G05D 15/01; G05D 16/20–2097
USPC .......... 602/13; 700/55, 73–79; 606/201–202; 600/485–499
See application file for complete search history.

(56) References Cited

U.S. PATENT DOCUMENTS

| | | | |
|---|---|---|---|
| 4,353,359 A | 10/1982 | Milbauer | |
| 4,396,010 A | 8/1983 | Arkans | |
| 4,469,099 A | 9/1984 | McEwen | |
| 4,492,234 A | 1/1985 | Arkans | |
| 4,605,010 A | 8/1986 | McEwen | |
| 4,631,683 A * | 12/1986 | Thomas ............. | G05B 19/4065 318/563 |
| 4,671,290 A | 6/1987 | Miller et al. | |
| 4,679,144 A | 7/1987 | Cox et al. | |
| 4,686,998 A | 8/1987 | Robbins | |
| 5,010,893 A | 4/1991 | Sholder | |
| 5,020,527 A | 6/1991 | Dessertine | |
| 5,050,613 A | 9/1991 | Newman et al. | |
| 5,052,375 A | 10/1991 | Stark et al. | |
| 5,103,833 A | 4/1992 | Apple | |
| 5,167,237 A | 12/1992 | Rabin et al. | |
| 5,233,987 A | 8/1993 | Fabian et al. | |
| 5,284,133 A | 2/1994 | Burns et al. | |
| 5,307,791 A | 5/1994 | Senoue et al. | |
| 5,331,548 A | 7/1994 | Rollema et al. | |
| 5,337,750 A | 8/1994 | Walloch | |
| 5,339,825 A | 8/1994 | McNaughton et al. | |
| 5,443,440 A | 8/1995 | Tumey et al. | |
| 5,459,700 A | 10/1995 | Jacobs | |
| 5,474,083 A | 12/1995 | Church et al. | |
| 5,514,079 A | 5/1996 | Dillon | |
| 5,554,103 A * | 9/1996 | Zheng ................. | A61B 5/0535 600/311 |
| 5,575,762 A | 11/1996 | Peeler et al. | |
| 5,591,200 A | 1/1997 | Cone et al. | |
| 5,622,180 A | 4/1997 | Tammi et al. | |
| 5,660,182 A * | 8/1997 | Kuroshaki ......... | A61B 5/02233 600/499 |
| 5,718,232 A | 2/1998 | Raines et al. | |
| 5,769,801 A | 6/1998 | Tumey et al. | |
| 5,806,512 A | 9/1998 | Abramov et al. | |
| 5,810,735 A | 9/1998 | Halperin et al. | |
| 5,840,049 A | 11/1998 | Tumey et al. | |
| 5,843,007 A | 12/1998 | McEwen et al. | |
| 5,929,782 A | 7/1999 | Stark et al. | |
| 5,951,502 A * | 9/1999 | Peeler ................. | A61H 9/0078 601/149 |
| 5,968,073 A | 10/1999 | Jacobs | |
| 5,982,285 A | 11/1999 | Bueche et al. | |
| 6,047,203 A | 4/2000 | Sackner et al. | |
| 6,051,016 A | 4/2000 | Mesaros et al. | |
| 6,102,874 A | 8/2000 | Stone et al. | |
| 6,135,106 A | 10/2000 | Dirks et al. | |
| 6,171,270 B1 | 1/2001 | Gau | |
| 6,188,407 B1 | 2/2001 | Smith et al. | |
| 6,200,265 B1 | 3/2001 | Walsh et al. | |
| 6,231,532 B1 | 5/2001 | Watson et al. | |
| 6,338,719 B1 | 1/2002 | Drzewiecki et al. | |
| 6,381,482 B1 | 4/2002 | Jayaraman et al. | |
| 6,387,065 B1 | 5/2002 | Tumey | |
| 6,416,471 B1 | 7/2002 | Kumar et al. | |
| 6,436,058 B1 | 8/2002 | Krahner et al. | |
| 6,440,082 B1 * | 8/2002 | Joo ...................... | A61B 5/0535 600/483 |
| 6,440,093 B1 | 8/2002 | McEwen et al. | |
| 6,450,981 B1 | 9/2002 | Shabty et al. | |
| 6,468,237 B1 | 10/2002 | Lina | |
| 6,514,200 B1 | 2/2003 | Khouri | |
| 6,527,711 B1 | 3/2003 | Stivoric et al. | |
| 6,544,202 B2 | 4/2003 | McEwen et al. | |
| 6,551,252 B2 | 4/2003 | Sackner et al. | |
| 6,616,579 B1 | 9/2003 | Reinbold et al. | |
| 6,736,787 B1 | 5/2004 | McEwen et al. | |
| 6,775,577 B2 | 8/2004 | Crnkovich et al. | |
| 6,926,667 B2 | 8/2005 | Khouri | |
| 7,115,104 B2 | 10/2006 | Van Brunt et al. | |
| 7,118,534 B2 | 10/2006 | Ward et al. | |
| 7,125,383 B2 | 10/2006 | Hoctor et al. | |
| 7,207,959 B1 | 4/2007 | Chandran | |
| 7,214,192 B2 | 5/2007 | Poliac et al. | |
| 7,220,235 B2 * | 5/2007 | Geheb ................. | A61B 5/11 601/41 |
| 7,244,225 B2 | 7/2007 | Loeb et al. | |
| 7,354,411 B2 | 4/2008 | Perry et al. | |
| 7,395,109 B2 | 7/2008 | Drakulic | |
| 7,398,803 B2 | 7/2008 | Newton | |
| 7,410,475 B2 | 8/2008 | Krensky et al. | |
| 7,425,203 B2 | 9/2008 | Van Brunt et al. | |
| 7,426,157 B2 | 9/2008 | Arnold et al. | |
| 7,593,765 B2 | 9/2009 | Rapoport et al. | |
| 7,618,384 B2 | 11/2009 | Nardi et al. | |
| 7,637,879 B2 | 12/2009 | Barak et al. | |
| 7,883,470 B2 * | 2/2011 | Scheiner ............. | A61B 5/042 600/513 |
| 7,909,786 B2 | 3/2011 | Bonnefin et al. | |
| 7,947,003 B2 | 5/2011 | Bonnefin et al. | |
| 7,972,275 B2 * | 7/2011 | Siejko ................ | A61B 5/02028 600/513 |
| 8,025,632 B2 | 9/2011 | Einarsson | |
| 8,128,584 B2 | 3/2012 | Brown | |
| 8,257,289 B2 | 9/2012 | Vess | |
| 8,578,939 B1 | 11/2013 | Kimani Mwangi et al. | |
| 8,630,699 B2 | 1/2014 | Baker et al. | |
| 8,764,667 B2 * | 7/2014 | Avidor ................ | A61B 5/029 600/302 |
| 8,974,491 B2 * | 3/2015 | Leschinsky ........ | A61B 5/02225 606/202 |
| 9,044,372 B2 | 6/2015 | Wild et al. | |
| 2002/0045804 A1 | 4/2002 | Christopherson et al. | |
| 2002/0087054 A1 | 7/2002 | Lin et al. | |
| 2003/0078528 A1 | 4/2003 | Rahman et al. | |
| 2003/0125649 A1 | 7/2003 | McIntosh et al. | |
| 2003/0135127 A1 | 7/2003 | Sackner et al. | |
| 2003/0216651 A1 | 11/2003 | Burns et al. | |
| 2004/0030270 A1 | 2/2004 | Johnson | |
| 2004/0054306 A1 | 3/2004 | Roth et al. | |
| 2004/0077934 A1 * | 4/2004 | Massad ............... | A61B 5/4857 600/300 |
| 2004/0127937 A1 | 7/2004 | Newton | |
| 2004/0199232 A1 | 10/2004 | Wallace et al. | |
| 2005/0033351 A1 | 2/2005 | Newton | |
| 2005/0107725 A1 | 5/2005 | Wild et al. | |

(56) References Cited

U.S. PATENT DOCUMENTS

| | | |
|---|---|---|
| 2005/0159690 A1 | 7/2005 | Barak et al. |
| 2005/0171248 A1 | 8/2005 | Li et al. |
| 2006/0058716 A1 | 3/2006 | Hui |
| 2006/0122544 A1 | 6/2006 | Ciluffo |
| 2007/0010749 A1 | 1/2007 | Meng |
| 2007/0049853 A1 | 3/2007 | Adams et al. |
| 2007/0083152 A1 | 4/2007 | Williams, Jr. et al. |
| 2007/0088239 A1 | 4/2007 | Roth et al. |
| 2007/0173886 A1 | 7/2007 | Rousso et al. |
| 2007/0249977 A1 | 10/2007 | Bonnefin et al. |
| 2008/0033307 A1 | 2/2008 | Baudoin et al. |
| 2008/0177159 A1 | 7/2008 | Gavriely |
| 2008/0183095 A1 | 7/2008 | Austin et al. |
| 2008/0188781 A1 | 8/2008 | Carkner et al. |
| 2008/0281630 A1 | 11/2008 | Sekura |
| 2008/0312522 A1 | 12/2008 | Rowlandson et al. |
| 2009/0005703 A1 | 1/2009 | Fasciano |
| 2009/0024062 A1 | 1/2009 | Einarsson |
| 2009/0036786 A1 | 2/2009 | Gough et al. |
| 2009/0048525 A1 | 2/2009 | Rogers et al. |
| 2009/0063194 A1 | 3/2009 | Rosneck et al. |
| 2009/0234265 A1 | 9/2009 | Reid, Jr. et al. |
| 2009/0259169 A1 | 10/2009 | Loori et al. |
| 2011/0230806 A1* | 9/2011 | Lou .................. A61F 5/012 602/13 |
| 2012/0083712 A1* | 4/2012 | Watson ............ G06F 19/00 600/587 |
| 2013/0231596 A1 | 9/2013 | Hornbach et al. |

FOREIGN PATENT DOCUMENTS

| | | |
|---|---|---|
| EP | 0396431 A1 | 11/1990 |
| EP | 0898475 B1 | 8/2002 |
| EP | 1645254 A1 | 4/2006 |
| EP | 2359785 A1 | 8/2011 |
| JP | 08280635 A | 10/1996 |
| WO | 00/00155 A1 | 1/2000 |
| WO | 03/007855 A1 | 1/2003 |
| WO | 2004062724 A1 | 7/2004 |
| WO | 2006043080 A1 | 4/2006 |
| WO | 2007041806 A1 | 4/2007 |
| WO | 2011112442 A1 | 9/2011 |
| WO | 2016/055992 A1 | 4/2016 |

OTHER PUBLICATIONS

Bogatin, "PCB Directions," Printed Circuit Design & Manufacture, Oct. 2003, vol. 20, Issue 10, Atlanta, GA, 1 page.

Gungor et al., "A New Micro-Controller based Wear-Time Monitor for Use with Removable Orthodontic Appliances", Proceedings of the 19th Annual International Conference—IEEE/EMBS, Oct. 30 thru Nov. 2, 1997. Chicago, IL, USA. 3 pages.

Kadiallah et al, "Impedance Control is Tuned to Multiple Directions of Movement," Conference Proceedings: Annual International Conference of the IEEE Engineering in Medicine & Biology Society, 2008:5358-61, Aug. 2008, 4 pages.

Prance, "Novel Sensor Enables Remote Biometric-Data Acquisition," Department of Engineering and Design—University of Sussex, 2008 SPIE, 2 pages.

SCD Response Compression System Controller. http://www.kendallvasculartherapy.com/VascularTherapy/ . . . Feb. 9, 2009, 1 page.

"Doctor Life Health Care". www.dsmaref.com as known as 2010, 41 pgs.

Aircast Inc., VenaFlow Operator's Manual, Apr. 4, 2001. 26 pgs.

"Compression Devices" www.mweb.com. vol. 67, No. 2, Feb. 2004. 2 pgs.

Orthofix Vascular Novamedix, "Take a step into the world of foot impulse technology" www.orthofix.com/avimpulse. as known as 2008, 4 pgs.

Tyco/Healthcare Kendall, "SCD Express Compression System". as known as 2001, 24 pgs.

Patel et al., "Detecting Human Movement by Differential Air Pressure Sensing in HVAC System Ductwork: An Exploration in Infrastructure Mediated Sensing," Proceeding Pervasive '08 Proceedings of the 6th International Conference on Pervasive Computing, Sydney, Australia—May 19-22, 2008, 18 pages.

Asada, H. Harry, et al., "Mobile Monitoring with Wearable Photoplethysmographic Biosensors", IEEE Engineering in Medicine and Biology Magazine, May/Jun. 2003, 13 pages.

Breault, Martine, "A Biomechanical Investigation of Blood Flow Occlusion Achieved With the Use of Surgical Pneumatic Tourniquets", B.A.Sc., McGill University, Montreal, 1985, University of British Columbia, Oct. 1988, 252 pages.

Coppin, Rhiannon, et al., "Functional Specifications for an Infant Monitoring System", http://www.sfu.ca/~rtrost/zentech, Feb. 16, 1999, 24 pages.

Côté, MD, Johanne, et al., "Compliance With Peak Expiratory Flow Monitoring in Home Management of Asthma*", Clinical Investigations, Chest / 113 / 4 / Apr. 1998, 5 pages.

Fahrenberg, J. & Myrtek, M (Eds.), "Origins and Developments of Ambulatory Monitoring and Assessment", Progress in Ambulatory Assessment, Computer-assisted Psychological and Psychophysiological Methods in Monitoring and Field Studies, Forschungsgruppe Psychophysiologie, Department of Psychology, University of Freiburg, Germany Chapter 35, 2001, pp. 587-616, 30 pages.

Felton, Kevin, CO, LO, "The Use of Adherence Monitors with Orthoses", JPO 1999; vol. 11, No. 4, p. 98, 3 pages.

Finkelstein, Joseph, et al., "Home Automated Telemanagement (HAT) System to Facilitate Self-Care of Patients with Chronic Diseases", Medical Information Systems Unit, Boston University, Boston, MA, Systemics, Cybernetics and Informatics, 2003, vol. 1, No. 3, 5 pages.

Havey, Robert, BS, et al., "A Reliable and Accurate Method for Measuring Orthosis Wearing Time", Spine vol. 27, No. 2, pp. 211-214, © 2002, Lippincott Williams & Wilkins, Inc., 4 pages.

Lou*, E., et al., "The daily force pattern of spinal orthoses in subjects with adolescent idiopathic scoliosis", Prosthetics and Orthotics International, 2002, 26, 58-63, 6 pages.

Scanlon, Michael V., "Acoustic Sensor for Health Status Monitoring", Army Research Laboratory, Night Vision and Electronic Sensors Directorate, Security Team, 1998, 10221 Burbeck Rd., Ft. Belvoir, VA22060-5806, 19 pages.

Verschelden, P., et al., "Compliance with and accuracy of daily self-assessment of peak expiratory flows (PEF) in asthmatic subjects over a three month period", European Respiratory Journal, 1996, 9, pp. 880-885, 6 pages.

\* cited by examiner

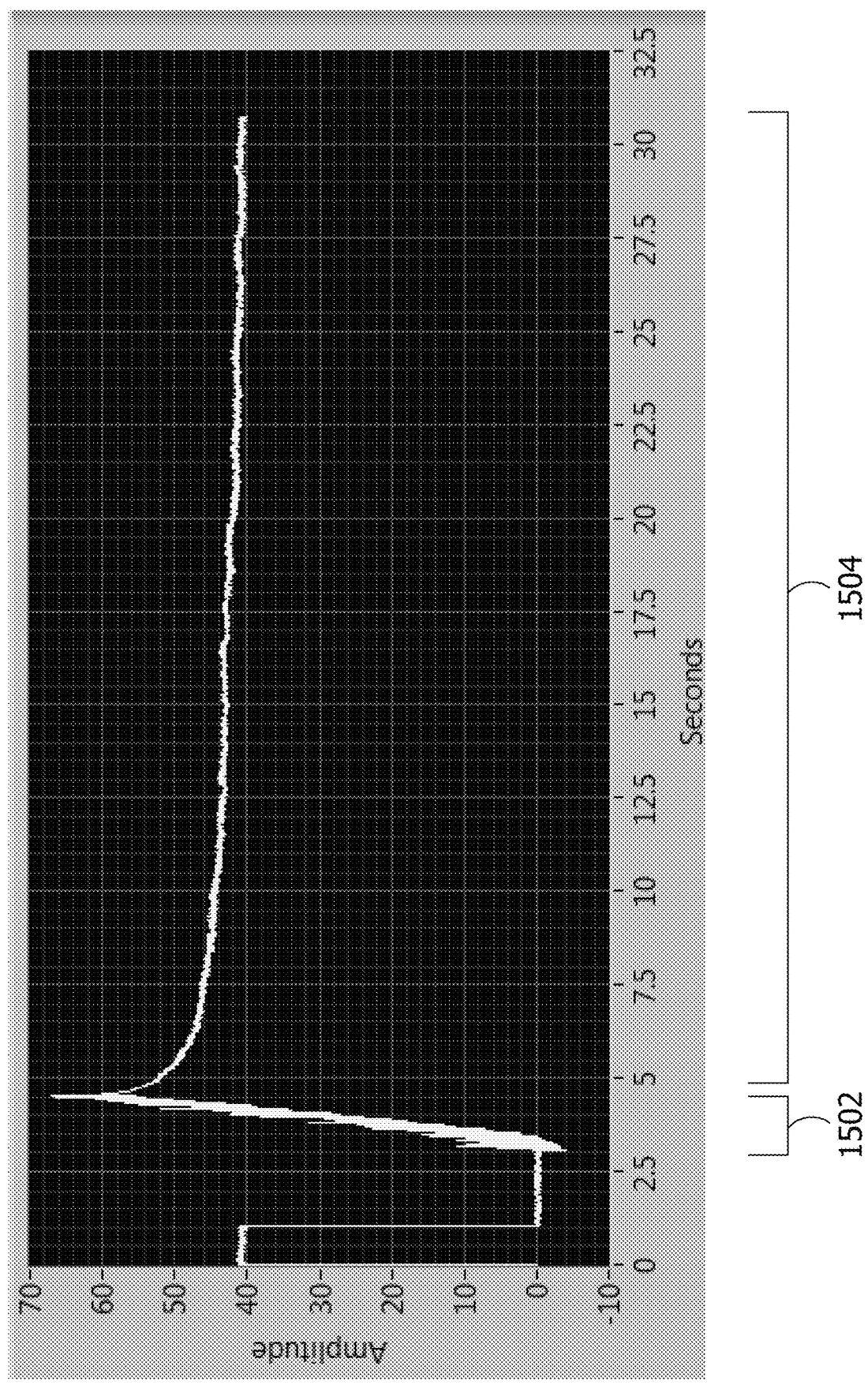

COMPRESSION GARMENT COMPLIANCE

CROSS-REFERENCE TO RELATED APPLICATIONS

This application claims priority from U.S. Provisional Patent Application Ser. No. 62/239,566, filed Oct. 9, 2015, entitled "Compression Garment Compliance," U.S. Provisional Patent Application Ser. No. 62/239,527, filed Oct. 9, 2015, entitled "Determining a Configuration of a Compression Garment," U.S. Provisional Patent Application Ser. No. 62/239,493, filed Oct. 9, 2015, entitled "Determining a Configuration of a Compression Garment," and U.S. Provisional Patent Application Ser. No. 62/329,233, filed Apr. 29, 2016, entitled "Determining a Configuration of a Compression Garment." The entire contents of the above-identified applications are expressly incorporated herein by reference, including the contents and teachings of any references contained therein.

BACKGROUND

Intermittent pneumatic compression (IPC) systems include devices used to apply pressurized fluid, such as air, to a limb of a patient or wearer. In some instances, pressurized air is applied to the lower limb of a patient at risk for the formation of deep vein thrombosis (DVT). An IPC system typically includes a pumping unit to manage pressurization of the fluid, a tubing set to extend the delivery of fluid beyond the pumping unit, and a compression garment which is wrapped around the patient's limb and contains the pressurized fluid. The IPC system intermittently pressurizes the garment to apply therapeutic compression to the patient's limb, moving blood from that area of the limb. The effectiveness of such IPC systems for DVT prophylaxis, however, depends on the patient's adherence to a prescribed treatment protocol including the IPC system.

SUMMARY

In an aspect, the present disclosure is directed to systems and methods of monitoring a wearer's compliance with a compression treatment regimen for use of a compression system. In another aspect, the present disclosure is directed to systems and methods of determining whether a compression garment is applied to a limb of a wearer.

In one aspect, a compression device controller includes a memory device, one or more processors coupled to the memory device, and computer-executable instructions embodied on a computer readable storage medium. The memory device is configured for storing monitored parameters. The computer-executable instructions include instructions for causing the one or more processors to direct the flow of fluid from a pressurized fluid flow source to inflate and deflate an inflatable bladder of a compression garment. The compression garment is configured to be wrapped around a limb of a wearer of the garment. Also included are instructions for causing the one or more processors to receive pressure signals indicative of fluid pressure in the inflatable bladder from a pressure sensor communicatively coupled to the bladder. The one or more processors, when caused by the instructions, process the received pressure signals during at least one of inflation and deflation of the inflatable bladder. The pressure signals are used to detect variance in the signals indicative of a change in condition of the compression garment. The instructions also cause the one or more processors to change a state of at least one of the monitored parameters in the memory device in response to detecting variance in the received pressure signals. The changed state of the monitored parameter is representative of the change in condition of the compression garment.

In another aspect, a computer-implemented method includes computer-executable instructions executing on one or more processors controlling a pressurized fluid flow source through a cycle of operation in which at least one inflatable bladder of a compression garment configured to be wrapped around a limb of a patient is inflated and deflated. The one or more processors receive pressure signals indicative of fluid pressure in the bladder from a pressure sensor communicatively coupled to the bladder. Computer-executable instructions executing on the one or more processors detect variance in the received pressure signals indicative of a change in condition of the compression garment during the inflation and deflation of the bladder. Computer-executable instructions executing on the one or more processors also change a state of at least one monitored parameter stored in a memory device in response to detecting variance in the received pressure signals. The memory device is coupled to the one or more processors and the changed state of the monitored parameter is representative of the change in condition of the compression garment.

In yet another aspect, a system includes a compression garment and a controller. The compression garment includes at least one inflatable and deflatable bladder and is securable about a limb of a wearer. The controller includes a memory device, one or more processors coupled to the memory device, and computer-executable instructions embodied on a computer readable storage medium. The memory device is configured for storing monitored parameters. The computer-executable instructions include instructions for causing the one or more processors to direct the flow of fluid from a pressurized fluid flow source to inflate and deflate the bladder of the compression garment. Also included are instructions for causing the one or more processors to receive pressure signals indicative of fluid pressure in the bladder from a pressure sensor communicatively coupled to the bladder. The one or more processors, when caused by the instructions, process the received pressure signals during at least one of inflation and deflation of the inflatable bladder. The pressure signals are used to detect variance in the signals indicative of a change in condition of the compression garment. The instructions also cause the one or more processors to change a state of at least one of the monitored parameters in the memory device in response to detecting variance in the received pressure signals. The changed state of the monitored parameter is representative of the change in condition of the compression garment.

Embodiments can include one or more of the following advantages.

In some embodiments, compliance monitoring of a compression system is performed using a signal indicative of pressure in an inflatable bladder of a compression garment, providing a real time indication of a wearer's compliance with use of the compression garment. This can, for example, provide a robust indication of compliance while reducing the burden on caregivers to track compliance.

Other aspects, features, and advantages will be apparent from the description and drawings, and from the claims.

BRIEF DESCRIPTION OF THE DRAWINGS

FIGS. 15A-15C are graphical representations of another pressure profile produced by the compression system of FIG. 1 when the compression garment is in a wrapped configuration on a limb of a wearer.

Corresponding reference characters indicate corresponding parts throughout the drawings.

DETAILED DESCRIPTION

As used herein, the terms "proximal" and "distal" represent relative locations of components, parts and the like of a compression garment when the garment is worn. For example, a "proximal" component is disposed most adjacent to the wearer's torso, a "distal" component is disposed most distant from the wearer's torso, and an "intermediate" component is disposed generally anywhere between the proximal and distal components. Further, as used herein, the terms "wrapped" and "unwrapped" define conditions of the garment where the garment is properly applied to the wearer's limb (wrapped) and where the garment is removed from the wearer's limb (unwrapped).

Figure 1:
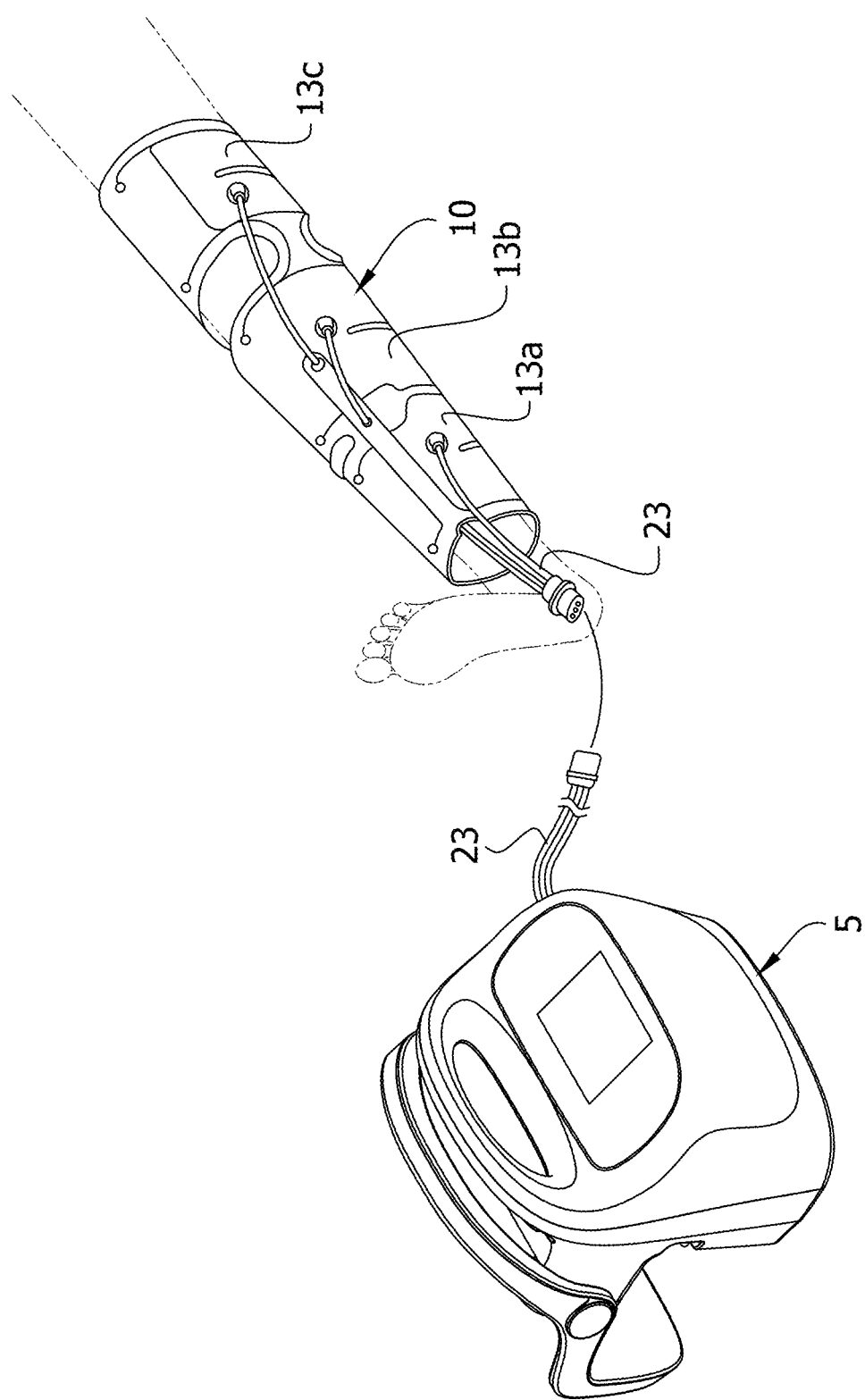
FIG. 1 is a perspective view of a compression system including a compression garment and a controller.
Figure 2:
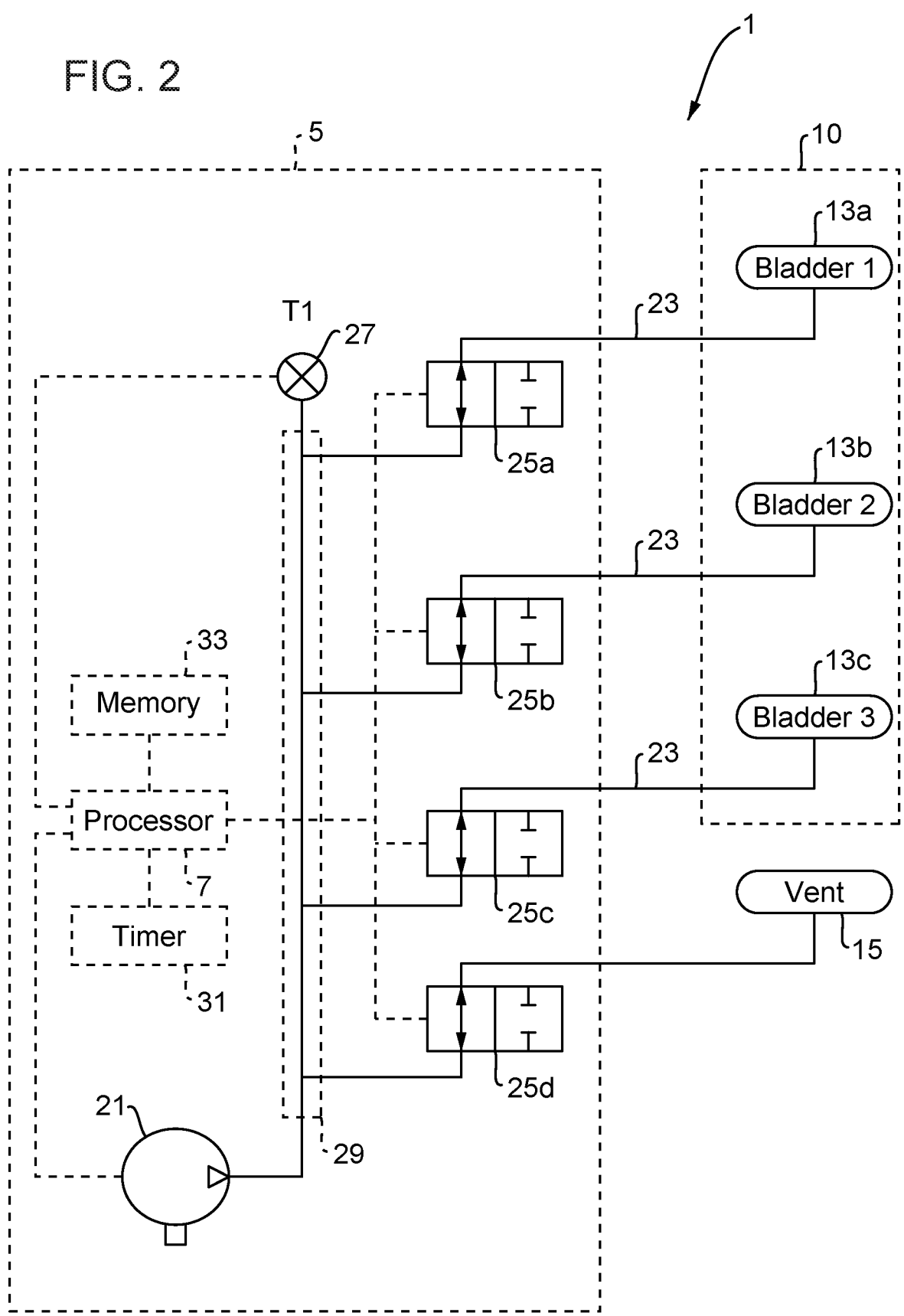
FIG. 2 is a schematic representation of the compression system of FIG. 1, including a schematic of a pneumatic circuit.
Figure 3:
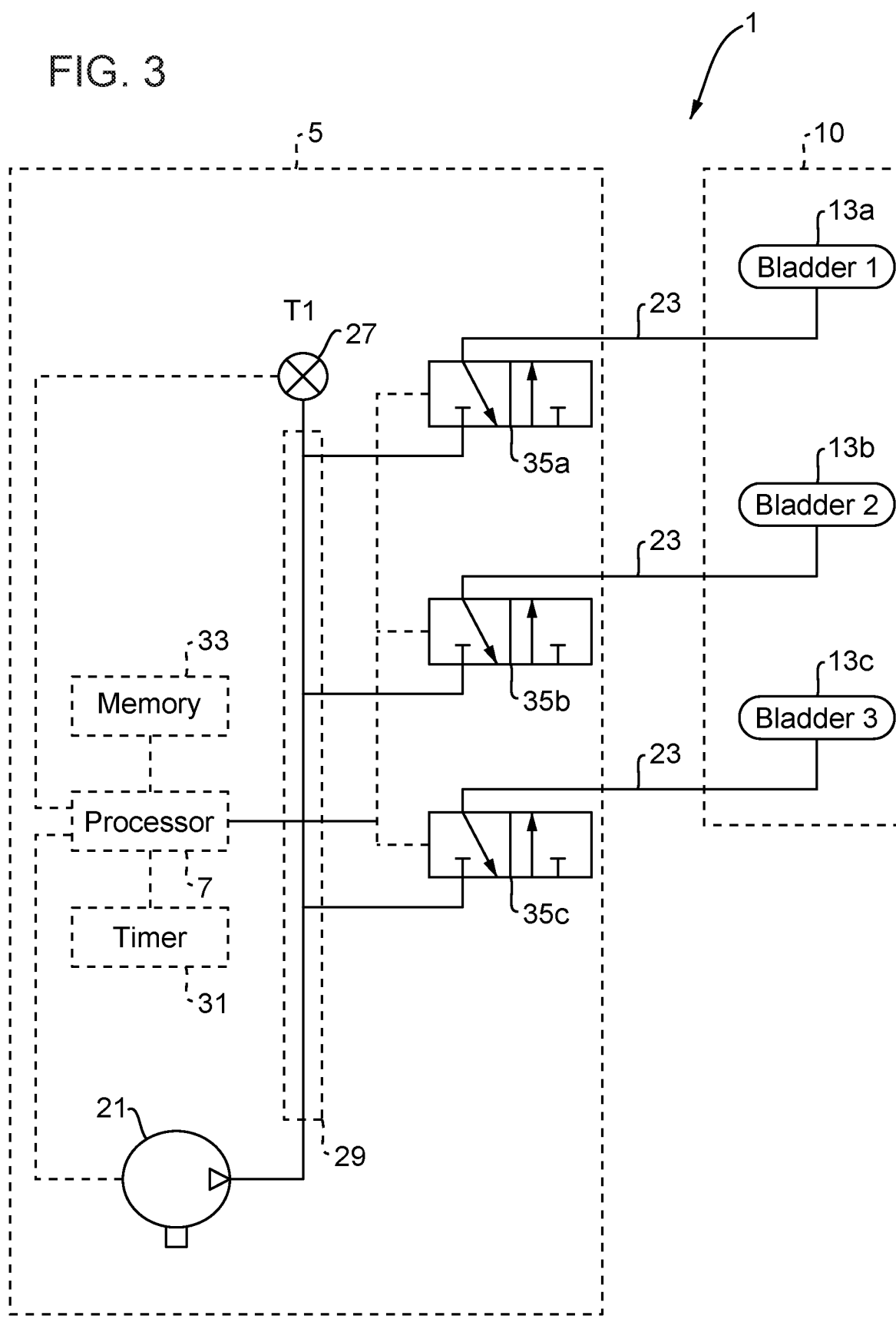
FIG. 3 is a schematic representation of another exemplary compression system of FIG. 1, including a schematic of a pneumatic circuit.

Referring to FIGS. 1-3, a compression system 1 includes a compression garment 10 for applying sequential compression therapy to a limb of a wearer and a controller 5 having one or more processors 7 and computer executable instructions embodied on a computer readable storage medium 33, the computer executable instructions including instructions for causing the one or more processors to control operation of the compression system 1. The compression garment 10 includes a distal inflatable bladder 13a, an intermediate inflatable bladder 13b, and a proximal inflatable bladder 13c. The compression garment 10 can be fastened around the wearer's limb and in one embodiment is adjustable to fit limbs of different circumferences.

As described in further detail below, the controller 5 controls operation of the compression system 1 to perform an inflation cycle, in which the inflatable bladders 13a, 13b, 13c are inflated to apply pressure to the wearer's limb to establish a gradient pressure applied to the wearer's limb by the inflatable bladders 13a, 13b, 13c of the compression garment 10 during one or more compression cycles. As also described in further detail below, for purposes of this description, each therapeutic compression cycle includes inflation phases for all three bladders 13a, 13b, 13c, a decay phase for bladders 13a and 13b, and a vent phase for all three bladders 13a, 13b, 13c. The end-of-cycle pressure of each bladder 13a, 13b, 13c is the pressure in each bladder 13a, 13b, 13c prior to initiation of the vent phase of the respective bladder 13a, 13b, 13c. As will be explained in greater detail below, the controller 5 determines, based at least in part on a measured pressure of one or more of the inflatable bladders 13a, 13b, 13b, whether or not the compression garment 10 is applied to (i.e., in a wrapped configuration around) a wearer's limb and, in some embodiments, provides an indication of the determination (e.g., by incrementing a timer, by pausing a timer, by providing an audible alarm, and/or by providing a visual indication on a graphical user interface). Determining whether the compression garment 10 is being worn (i.e., in a wrapped configuration around a wearer's limb) provides a compliance monitoring function which enables the compression system 1 to track when the garment is being properly used to achieve a prescribed treatment. As also described in further detail below, the controller 5 can control operation of the compression system 1 to perform an inflation cycle, in which the inflatable bladders 13a, 13b, 13c are inflated to apply pressure to the wearer's limb to establish, for example, a gradient pressure applied to the wearer's limb by the inflatable bladders 13a, 13b, 13c of the compression garment 10 during one or more compression cycles.

The compression garment 10 is a thigh-length sleeve positionable around the leg of the wearer, with the distal bladder 13a around the wearer's ankle, the intermediate bladder 13b around the wearer's calf, and the proximal bladder 13c around the wearer's thigh. It will be understood by one of ordinary skill in the art that compression garment 10 may be a knee-length sleeve, a foot garment, and the like without departing from the scope of the invention. The inflatable bladders 13a, 13b, 13c expand and contract under the influence of fluid (e.g., air or other fluids) delivered from a pressurized fluid source 21 (e.g., a pump or compressor) in electrical communication with the controller 5. The pressurized fluid source 21 delivers pressurized fluid (e.g., air) to the inflatable bladders 13a, 13b, 13c through tubing 23.

Referring to FIG. 2, each inflatable bladder 13a, 13b, 13c is in fluid communication with a respective valve 25a, 25b, 25c. A pressure sensor 27 is in communication (e.g., fluid communication) with a manifold 29 to measure a signal indicative of pressure in the manifold 29. Fluid communication between the manifold 29 and the respective inflatable bladders 13a, 13b, 13c can be controlled through control of the position of the respective valves 25a, 25b, 25c (e.g., through activation and/or deactivation of the respective valves 25a, 25b, 25c). The pressure sensor 27 is in electrical communication with the controller 5 such that the controller 5 receives from the pressure sensor 27 signals indicative of the pressure of the manifold 29 and/or one or more of the inflatable bladders 13a, 13b, 13c in fluid communication with the manifold 29 as a result of the positions of the respective valves 25a, 25b, 25c. If only one bladder 13a, 13b or 13c is in fluid communication with the manifold 29, the signal received from the pressure sensor 27 is indicative of the pressure of the respective bladder 13a, 13b, 13c in fluid communication with the manifold 29. For example, the pressure sensor 27 provides a signal indicative of the pressure in the inflatable bladder 13a when valve 25a is open and valves 25b, 25c are closed. Similarly, the pressure sensor 27 provides a signal indicative of the pressure in the bladder 13b when the valve 25b is open and the valves 25a and 25c are closed. Likewise, the pressure sensor 27 provides a signal indicative of the pressure in the inflatable bladder 13c when the valve 25c is open and the valves 25a and 25b are closed. A vent valve 25d is actuatable to control fluid communication between the manifold 29 and a vent port 15, which vents to ambient atmosphere. All bladders 13a, 13b, 13c can be vented using the vent valve 25d.

Each valve 25a, 25b, 25c is a 2-way/2-position, normally open, solenoid valve. Each valve 25a, 25b, 25c includes two ports and is actuatable to place an inlet port in fluid communication with a bladder port in a first, open position. Each valve 25a, 25b, 25c is further actuatable to shut off fluid communication between the inlet port and the bladder port. The inlet port of each valve 25a, 25b, 25c is in fluid communication with the pressurized fluid source 21 and the manifold 29. The bladder port of each valve 25a, 25b, 25c is in fluid communication with a respective inflatable bladder 13a, 13b, 13c.

Any one of the bladders 13a, 13b, 13c can be placed in fluid communication with the pressurized fluid source 21 and the manifold 29 by the respective valve 25a, 25b, 25c to deliver pressurized fluid to the bladder 13a, 13b, 13c. After the bladder 13a, 13b, 13c is inflated, the respective valve 25a, 25b, 25c can be closed to hold the fluid in the respective bladder 13a, 13b, 13c. Thus, the bladders 13a, 13b, 13c of the compression garment 10 can be individually inflated by opening the respective valve 25a, 25b, 25c and closing the other valves 25a, 25b, 25c so that only the one bladder 13a, 13b, 13c associated with the opened valve 25a, 25b, 25c is in fluid communication with the pressurized fluid source 21 and the manifold 29.

The vent valve 25d is also a 2-way/2-position, normally open, solenoid valve. The vent valve 25d includes two ports and is actuatable to place an inlet port in fluid communication with a vent port 15 in a first position. The vent inlet port is in fluid communication with a vent port 15 in a first position. The vent valve 25d is further actuatable to shut off fluid communication between the inlet port and the vent port 15. The inlet port of vent valve 25d is in fluid communication with the pressurized fluid source 21 and the manifold 29. The vent port 15 of the vent valve 25d is in fluid communication with ambient atmosphere.

It should be appreciated that the valves 25a, 25b, 25c, 25d could be other types and have other arrangements within the compression system 1 without departing from the scope of the present disclosure. For example, referring to FIG. 3, the valves may be valves 35a, 35b, 35c, which are 3-way/2-position solenoid valves and are actuatable to control the pressure in bladders 13a, 13b, 13c without a vent valve.

With reference again to FIG. 2, the computer executable instructions embodied on the computer readable storage medium 33 include instructions to cause the one or more processors 7 to pressurize (e.g., inflate) the inflatable bladders 13a, 13b, 13c to provide cyclical therapeutic compression pressure to a wearer's limb. For example, the computer executable instructions embodied on the computer readable storage medium 33 include instructions to cause the one or more processors 7 to control the pressurized fluid source 21 and/or the valves 25a, 25b, 25c, 25d to pressurize the inflatable bladders 13a, 13b, 13c to therapeutic compression pressures for a predetermined amount of time to move the blood in the limb from regions underlying the inflatable bladders 13a, 13b, 13c. The length of time the bladder 13a, 13b is held at the compression pressure is referred to herein as a decay phase. Following the decay phase is a vent phase in which the computer executable instructions include instructions to cause the one or more processors 7 to control the pressurized fluid source 21 and/or the valves 25a, 25b, 25c, 25d to reduce the pressure in the inflatable bladders 13a, 13b, 13c to a lower pressure (e.g., atmospheric pressure).

The compression system 1 can determine whether or not the compression garment 10 is applied (i.e., wrapped) to a wearer's limb and, in certain embodiments, can provide an indication of that determination, which can facilitate, for example, tracking the wearer's compliance with a prescribed therapeutic use of the compression garment 10. The computer executable instructions embodied on the non-transitory computer readable storage medium 33 include instructions to cause the one or more processors 7 to analyze pressure signal data received from the pressure sensor 27 during a decompression period of a therapeutic cycle of the compression system 1. The computer executable instructions embodied on the non-transitory computer readable storage medium 33 include instructions to cause the one or more processors 7 to determine whether or not the characteristics of the received pressure signal data satisfy one or more conditions indicative of the compression garment 10 positioned on a wearer's limb.

In an exemplary embodiment, the computer executable instructions cause the one or more processors 7 to receive pressure signal data from the pressure sensor 27. The computer executable instructions can include instructions to cause the one or more processors 7 to process a single waveform representative of the pressures within one or more of the bladders 13a, 13b, 13c. It should be appreciated that the one or more processors 7 may process multiple waveforms without departing from the scope of the present disclosure. By monitoring the pressure signals and corresponding pressure data during, for example, a decompression period of the therapy cycle, the one or more processors 7 can detect certain characteristics on the waveform that are indicative of whether the compression garment 10 is properly wrapped on a wearer's limb or is unwrapped from a wearer's limb. In certain embodiments, during the decompression period, the pressure sensor 27 remains (or is intentionally placed) in constant communication (e.g., fluidic and/or mechanical communication) with one or more of the bladders 13a, 13b, 13c. Exemplary static periods include non-therapeutic cycles (e.g., pressures in bladders 13a, 13b, 13c of less than about 25 mmHg), a subset of an initial garment detection period, and/or a venous refill measurement period.

In an exemplary operation of the embodiment of FIG. 3, in which 3-way/2-position valves are utilized, the computer-executable instructions embodied on the computer readable storage medium 33 include instructions to cause the one or more processors 7 to control one or more valves 35a, 35b, 35c for one or more of a particular bladder 13a, 13b, 13c such that a fluidic path is established between the pressure sensor 27 and one or more of the bladders 13a, 13b, 13c.

In an exemplary operation of the embodiment of FIG. 2, in which 2-way/2-position valves are utilized, the computer-executable instructions embodied on the computer readable storage medium 33 include instructions to cause the one or more processors 7 to open or close the vent valve 25d such that the manifold 29 can no longer vent. One or more of the computer-executable instructions causes the one or more processors 7 to determine whether the signal received from the pressure sensor 27 for random pressure impulses and spikes that are expected to occur as the wearer moves (e.g., moving leg, flexing calf, coughing, sneezing, general breathing, etc.). Due to a volume of fluid (e.g., air) that is retained within one or more of the bladders 13a, 13b, 13c and extends to the manifold 29, and thus the pressure sensor 27, even slight movement causes the bladder to move or change shape and produce a pressure spike in the pressure signal generated by pressure sensor 27. Conversely, for a compression garment 10 that has been removed from a limb of the wearer, the pressure signal generated by pressure sensor 27 is static and devoid of random noise or pressure impulses.

Figure 4:
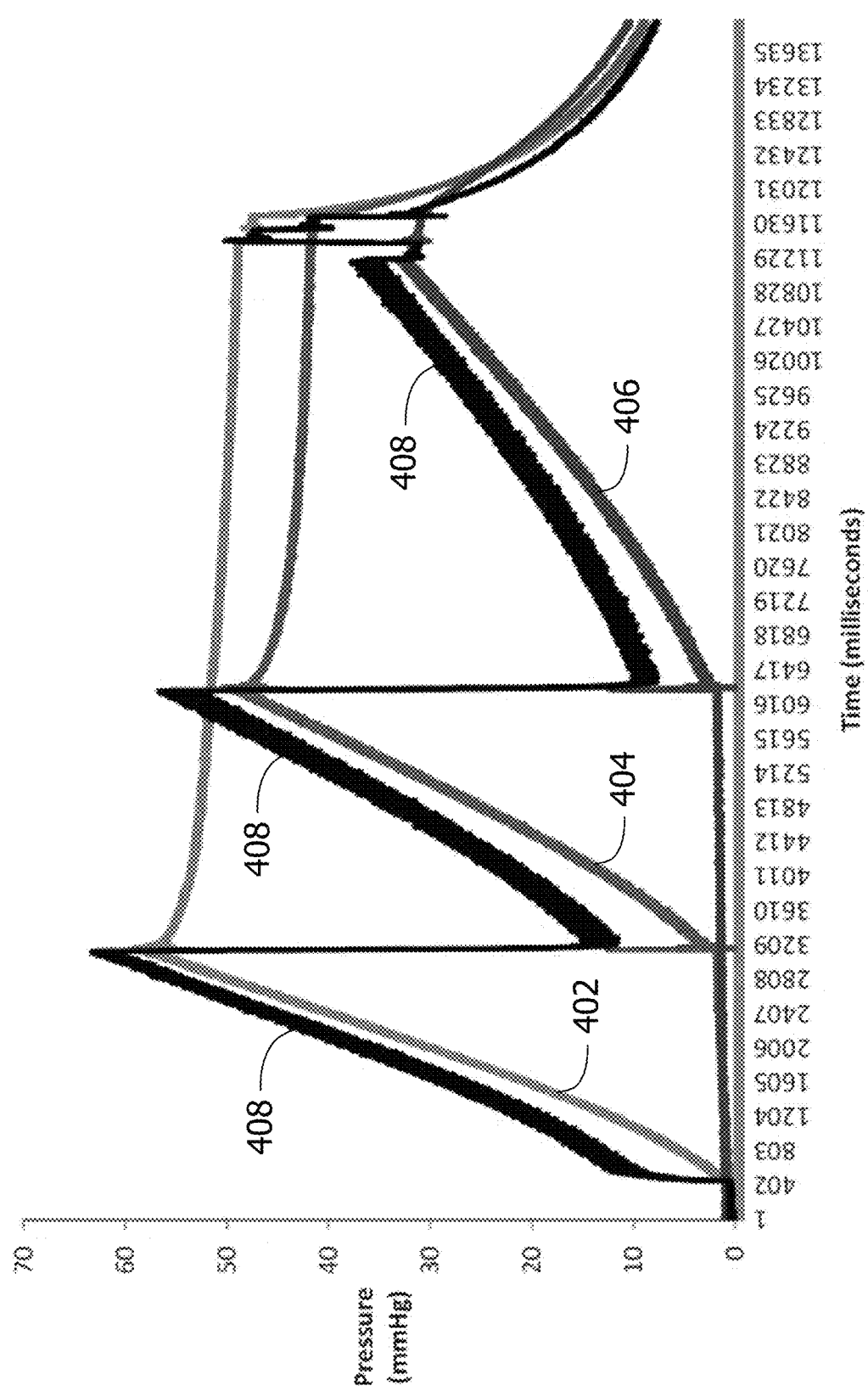
FIG. 4 is a graphical representation of a pressure profile produced by the compression system of FIG. 1 when the compression garment is in a wrapped configuration on a leg form, simulating a limb of a wearer.

Referring now to FIG. 4, a representative compression cycle pressure profile is shown for the compression garment 10 in a wrapped configuration around a leg form, which simulates a leg of a wearer. The leg form has a size, shape, and rigidity similar to those of a human leg. Accordingly, for the purpose of analyzing the performance of the algorithms described in this disclosure, the leg form is a suitable analog for a leg of a human wearer. Unless otherwise specified, all data shown herein were acquired in an experimental set-up using a leg form.

This graph shows signals from an experimental set-up in which pressure sensors are used to measure pressure in the individual bladders 13a, 13b, 13c and the pressure sensor 27 is used to measure pressure in the manifold 29. As described in further detail below, using this experimental set-up, the pressures measured in the individual bladders 13a, 13b, 13c are compared to the pressure measured by the pressure sensor 27 in the manifold 29. It should be appreciated that, in normal use, the controller 5 receives the signals from pressure sensor 27 to control operation of the compression system 1. FIG. 4 shows the correspondence between the manifold pressure measured by pressure sensor 27 and the pressure measured by pressure sensors disposed in each bladder 13a, 13b, 13c.

A single compression cycle for at least one of the bladders 13a, 13b, 13c includes an inflation phase, a decay phase, and a vent phase for the bladders 13a, 13b, and an inflation phase and a vent phase for the bladder 13c. Pressure plot 402 shows a pressure signal throughout a single therapeutic compression cycle for the distal bladder 13a, pressure plot 404 shows a pressure throughout a single therapeutic compression cycle for the intermediate bladder 13b, pressure plot 406 shows a pressure throughout a single therapeutic compression cycle for the proximal bladder 13c, and pressure plot 408 shows the manifold pressure measured by pressure sensor 27 during each of the aforementioned therapeutic compression cycles. Each plot 402, 404, 406 includes an initial bladder fill period which defines the inflation phase of the therapeutic compression cycle for the respective bladder 13a, 13b, 13c. Once a respective target pressure is achieved in the bladders 13a, 13b, inflation is stopped and the pressure in the bladder can be held at or near the target pressure defining the decay phase of the therapeutic compression cycle for bladders 13a, 13b. After the decay phase, in the case of bladders 13a, 13b, or immediately after the inflation phase, in the case of bladder 13c, fluid in each bladder 13a, 13b, 13c is evacuated from the respective bladder during the vent phase of the therapeutic compression cycle for each bladder 13a, 13b, 13c.

At the beginning of the therapeutic compression cycle, the valves 25b, 25c, and 25d are energized to a closed position. To inflate the distal bladder 13a, pressurized fluid from the pressurized fluid source 21 is delivered to the distal bladder 13a via the valve 25a and the tubing 23. Once a target pressure for the distal bladder 13a is achieved, or after a period of time measured by timer 31 after which the target pressure is expected to be achieved, the valve 25a is energized to close, holding the pressurized fluid in the distal bladder 13a. Next the intermediate bladder 13b is inflated by de-energizing valve 25b to an open position such that pressurized fluid from the pressurized fluid source 21 flows into the intermediate bladder 13b. Once a target pressure for the intermediate bladder 13b is achieved, or after a period of time measured by the timer 31 after which the target pressure is expected to be achieved, the valve 25b is energized to close, holding the pressurized fluid in the intermediate bladder 13b. Next, the proximal bladder 13c is inflated by de-energizing valve 25c to an open position such that pressurized fluid from the pressurized fluid source 21 flows into the proximal bladder 13c. Once a target pressure for the proximal bladder 13c is achieved, or after a period of time measured by the timer 31, after which the target pressure is expected to be achieved, valves 25a, 25b, and 25d are also de-energized to respective open positions. The open vent valve 25d allows for the fluid in each of the bladders 13a, 13b, 13c to vent to atmosphere.

The compression system 1 has been described as individually inflating each bladder 13a, 13b, 13c such that only one bladder is being filled with pressurized fluid at a time. It should be appreciated, however, that the bladders 13a, 13b, 13c can additionally or alternatively be inflated simultaneously or in any combination with one another. In certain embodiments, the opening and closing of valves 25a, 25b, 25c, and 25d are timed such that only one bladder 13a, 13b, 13c is in fluid communication with the pressure sensor 27 and the manifold 29 at a time. This facilitates, for example, the use of the pressure sensor 27 to measure a signal indicative of each of the pressure of each of the bladders 13a, 13b, 13c.

The computer executable instructions embodied on the computer readable storage medium 33 include instructions to cause the one or more processors 7 to receive a measured pressure signal from the pressure sensor 27 throughout the therapeutic compression cycle. As the distal bladder 13a is inflated, the one or more processors 7 receive from the pressure sensor 27 a signal indicative of pressure in the manifold 29, which is representative of the pressure in the distal bladder 13a. In this manner, pressure throughout the inflation phase of the distal bladder 13a is measured, including an end of inflation pressure just before valve 25a is closed. As the intermediate bladder 13b is inflated, the one or more processors 7 receive from the pressure sensor 27 a signal indicative of the pressure in the manifold 29, which is representative of the pressure in the intermediate bladder 13b. Pressure throughout the inflation phase of the intermediate bladder 13b is measured, including an end of inflation pressure just before valve 25b is closed. As the proximal bladder 13c is inflated, the one or more processors 7 receive from the pressure sensor 27 a signal indicative of the pressure in the manifold 29, which is representative of the pressure in the proximal bladder 13c. Pressure throughout the inflation phase of the proximal bladder 13c is measured, including an end of inflation pressure.

The computer executable instructions include instructions to cause the one or more processors 7 to determine an end-of-cycle pressure in each bladder 13a, 13b, 13c. As used herein, the end-of-cycle pressure is the pressure in each respective bladder 13a, 13b, 13c prior to the vent phase. Thus, for the bladders 13a, 13b, the end-of-cycle pressure for each bladder 13a, 13b is the pressure in each bladder 13a, 13b at the end of the respective decay phase of the therapeutic compression cycle of each bladder 13a, 13b. For bladder 13c, the end-of-cycle pressure is the pressure in the bladder 13c at the end of the inflation phase of the bladder 13c.

To measure the end-of-cycle pressure, the valves 25a, 25b, 25c are sequentially toggled open and closed after the proximal bladder 13c is inflated to its target pressure to measure an end-of-cycle pressure in each of the bladders 13a, 13b, 13c (FIG. 4). Because the valve 25c is open from having just inflated the proximal bladder 13c, the end of cycle pressure for the proximal bladder 13c is measured first. As will be understood from viewing the pressure profile in FIG. 6, the end of inflation pressure and the end of cycle pressure for the proximal bladder 13c are the same because the proximal bladder does not undergo a decay phase. Valve 25c can be toggled off and then toggled back on at the end of the compression cycle of the proximal bladder 13c. The one or more processors 7 toggle open valve 25a and close valve 25c to measure an end of cycle pressure for the distal bladder 13a. The one or more processors 7 toggle open valve 25b and close valve 25a to measure an end of cycle pressure for the intermediate bladder 13b. While a specific toggling sequence of the valves 25a, 25b, 25c is described, it should be appreciated that other toggling sequences of the valves 25a, 25b, 25c are within the scope of the present disclosure. In one embodiment, each valve 25a, 25b, 25c is toggled open for about 150 milliseconds (ms) to measure the end of cycle pressure in the respective bladder 13a, 13b, 13c. The valves 25a, 25b, 25c could be toggled open for a shorter or longer period of time. For instance, the valves 25a, 25b, 25c could be toggled open for at least about 75 ms. Still other periods of time are envisioned. The pressure readings measured by the pressure sensor 27 are stored in the memory 33. During operation, the compression cycle is repeated multiple times in succession to complete a compression treatment.

The computer executable instructions can include instructions to cause the one or more processors 7 to determine a representative line fit using the end of inflation pressure and the end of cycle pressure for at least one of the bladders 13a, 13b. Using the two pressure points, a line representing the decay phase is produced. The values of this representative line are compared to the end of inflation pressure for a bladder 13b, 13c to determine whether the pressure of the subsequently inflated bladder 13b, 13c potentially rose above the pressure of the previously inflated bladder 13a, 13b at any point during the compression cycle.

Figure 5:
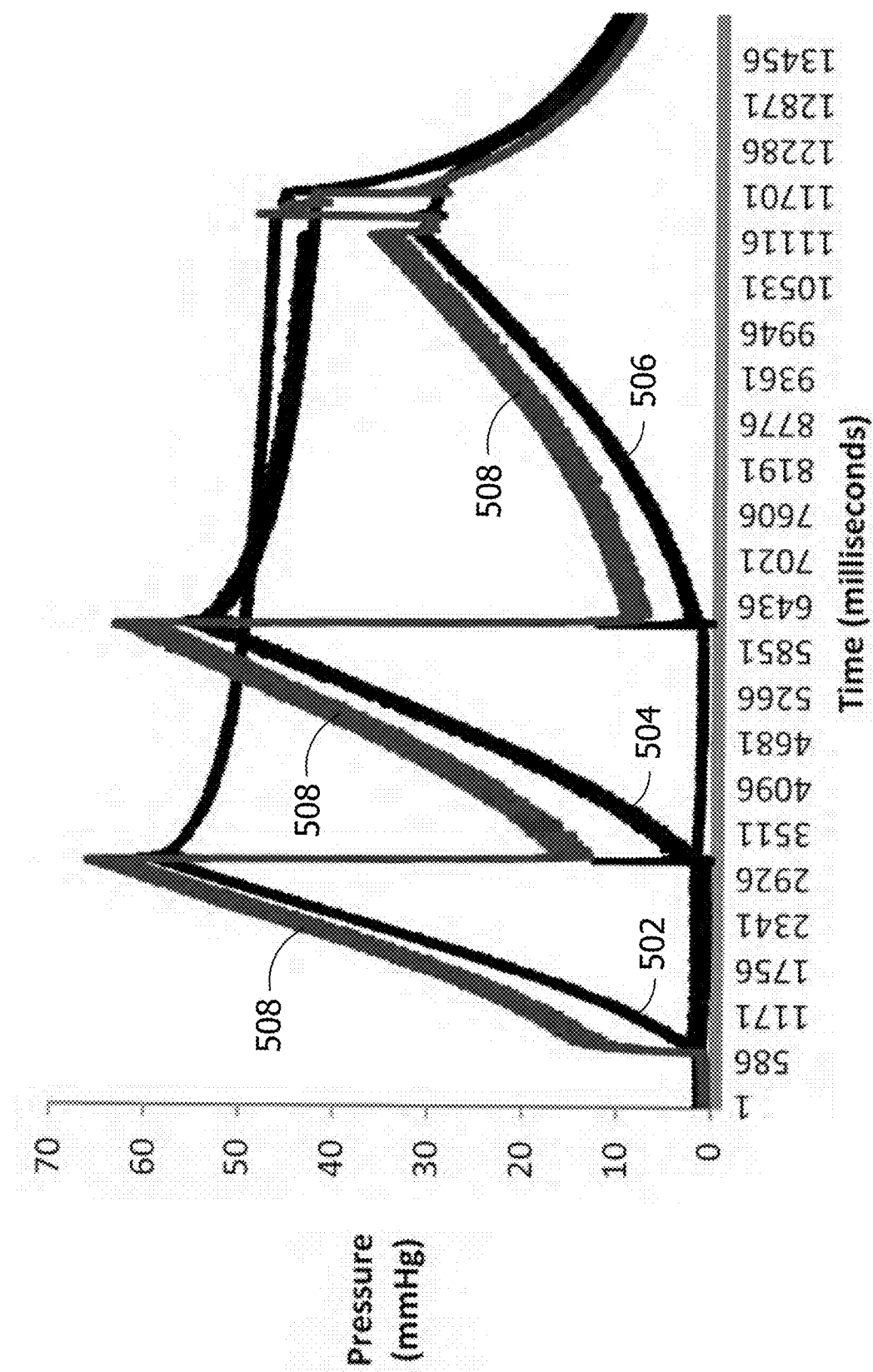
FIG. 5 is a graphical representation of a pressure profile produced by the compression system of FIG. 1 when a compression garment of the system is in an unwrapped configuration and away from a leg form, simulating a limb of a wearer.

Referring to FIG. 5, a representative compression cycle pressure profile for an unwrapped configuration of the compression system 1 is illustrated. Operation of the compression system 1 to produce the pressure profile of FIG. 5 is identical to the operation described above for the compression cycle pressure profile of FIG. 4. The only difference is the pressure signals in FIG. 5 were taken when the compression garment 10 was in the unwrapped configuration. Pressure plots 502, 504, 506 show an actual pressure of the distal bladder 13a, intermediate bladder 13b, and proximal bladder 13c throughout a single compression cycle when the garment 10 is in the unwrapped configuration. The pressure signal from the pressure sensor 27, which is representative of the pressure in the manifold 29 during the therapeutic compression cycle, is also shown in FIG. 5 as pressure plot 508.

Figure 6:
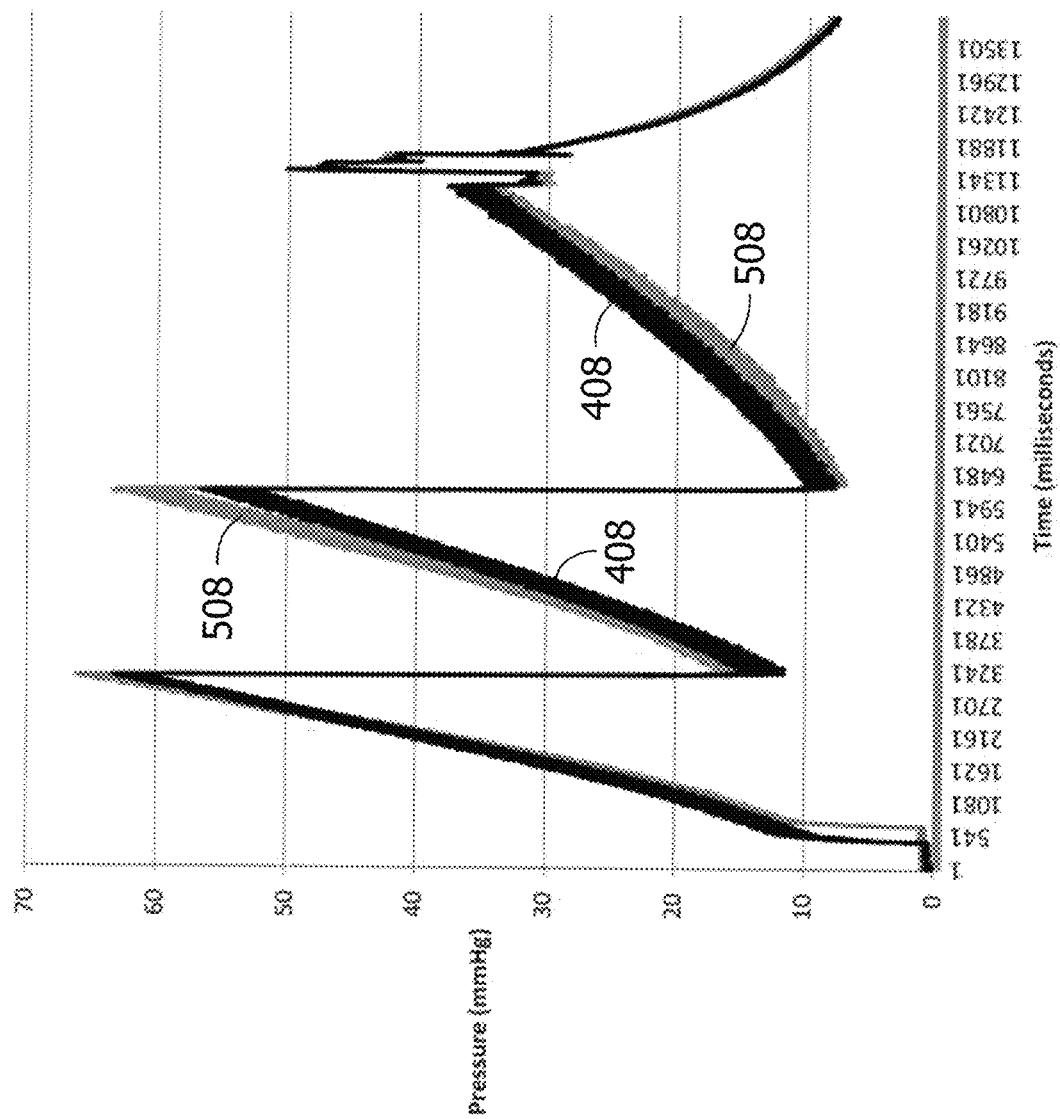
FIG. 6 is a graphical representation of the manifold pressure signals of the compression system of FIG. 1, the manifold pressure signals corresponding to manifold pressure signals for the wrapped and unwrapped compression garment configurations in FIGS. 4 and 5, respectively.

Referring to FIG. 6, the pressure signals of the representative compression cycle pressure profiles detected by the pressure sensor 27 for the wrapped and unwrapped configurations are plotted together. As will be explained in greater detail below, there are characteristics in the representative compression cycle pressure profiles which distinguish the wrapped and wrapped configurations. For instance, referring to FIG. 5, there is a period (e.g., around 6436 ms) when the intermediate bladder 13b (504) pressure exceeds the pressure of the distal bladder 13a (502). Additionally, the pressure in the bladders 13a, 13b, 13c before the bladders are inflated (i.e., initial pressure offset when time=0) is slightly higher in the unwrapped configuration. The offset is a result of more residual air being in the bladders 13a, 13b, 13c when the garment 10 is removed from the limb. Applicant believes this to be because the unwrapped sleeve is less constrained, thereby less evacuative force is applied to expel the residual air (i.e. the sleeve is able to remain "puffed out" thus appearing as though it is smaller in volume). Without wishing to be bound by theory, it is believed that this offset results from the unwrapped compression garment 10 being less constrained, resulting in less evacuative force being applied to expel residual air. Additionally, the end of inflation pressures for bladders 13a and 13b in the unwrapped configuration are slightly higher than the end of inflation pressures for bladders 13a and 13b in the wrapped configuration. The reverse condition is true for the proximal bladder 13c where the end of inflation pressure for the wrapped configuration is slightly higher than the end of inflation pressure for the unwrapped configuration. Another differentiating characteristic is that there is less differential between the end of inflation pressures in the distal and intermediate bladders 13a, 13b for the unwrapped configuration than for the wrapped configuration.

The computer executable instructions embodied on the computer readable storage medium 33 include instructions to cause the one or more processors 7 to model the pressure signals from the pressure sensor 27 in both the wrapped and unwrapped configurations. In an embodiment, the pressure signal from the inflation phase of the distal bladder 13a in the wrapped configuration is modeled by a best fit line. For example, the models are best fit lines generated by simple linear regression.

Analysis of the pressure signal data using the best fit line can provide an indication of whether the bladder 13a is in a compliant wrapped configuration, or a non-compliant unwrapped configuration when compression therapy is being applied. The difference between the best fit line and the observed pressure signals is mathematically quantifiable as a means squared error (MSE) value. In this instance, the MSE value is an indicator of the degree of curvature of the observed pressure trend over a given interval such as inflation of a bladder of the compression garment 10. Thus, a larger MSE value indicates that the curve fit data has a larger curvature, and a low MSE value indicates that the curve fit data has a smaller curvature. In an embodiment, the plot for the wrapped configuration is generally straighter (i.e., more nearly conforming to the corresponding best fit line) than the plot for the unwrapped configuration. Mathematically this translates to a smaller MSE value for the curve fit line of the plot for the wrapped configuration. In an embodiment, an MSE value under a predetermined number indicates that the bladder is in the wrapped configuration, while an MSE value greater than or equal to the predetermined number indicates that the bladder is in the unwrapped configuration. It is envisioned that other factors may provide an indication of the configuration of the bladder.

Figure 7:
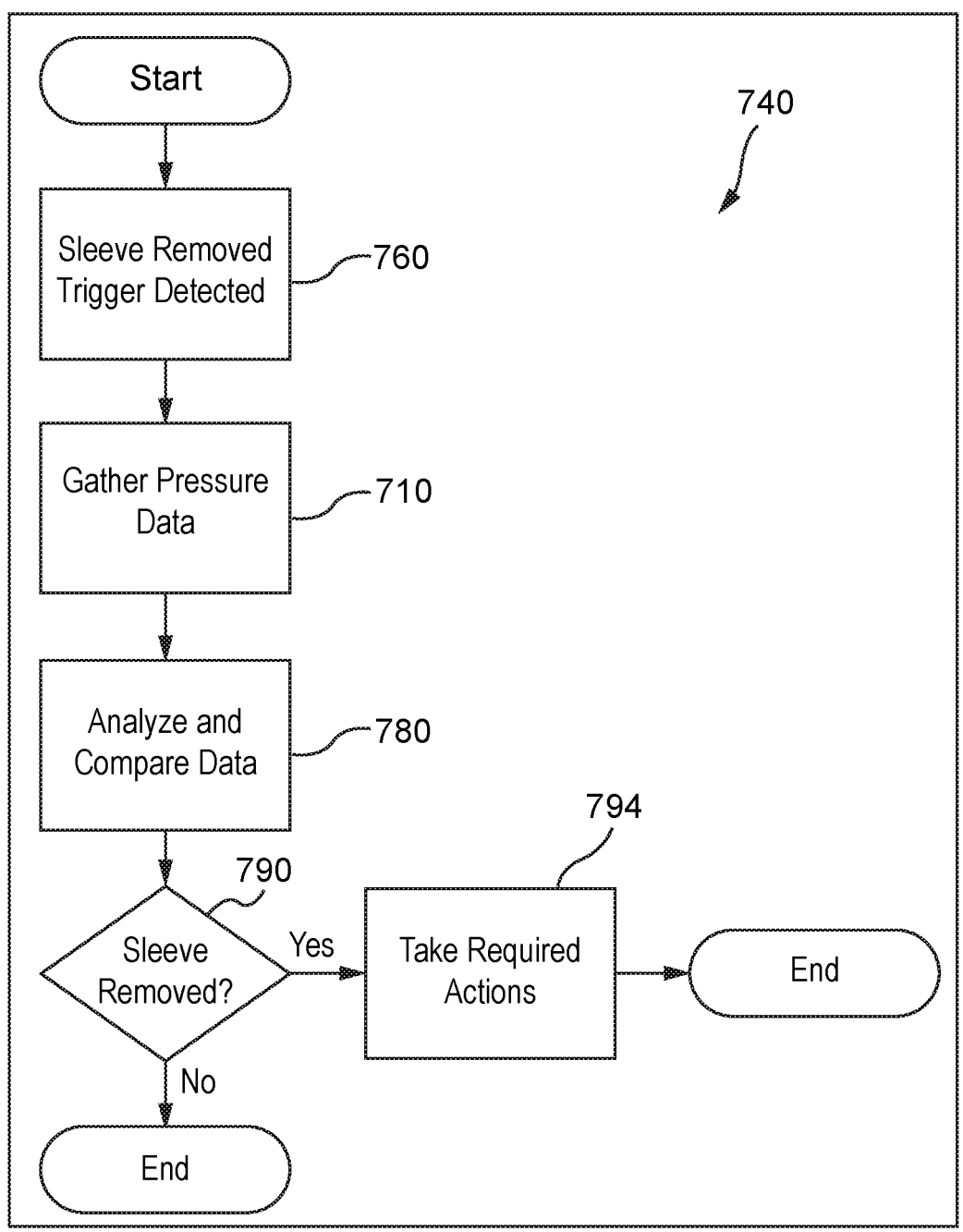
FIG. 7 is a flow diagram of a method of compliance monitoring using the compression system of FIG. 1.
Figure 8:
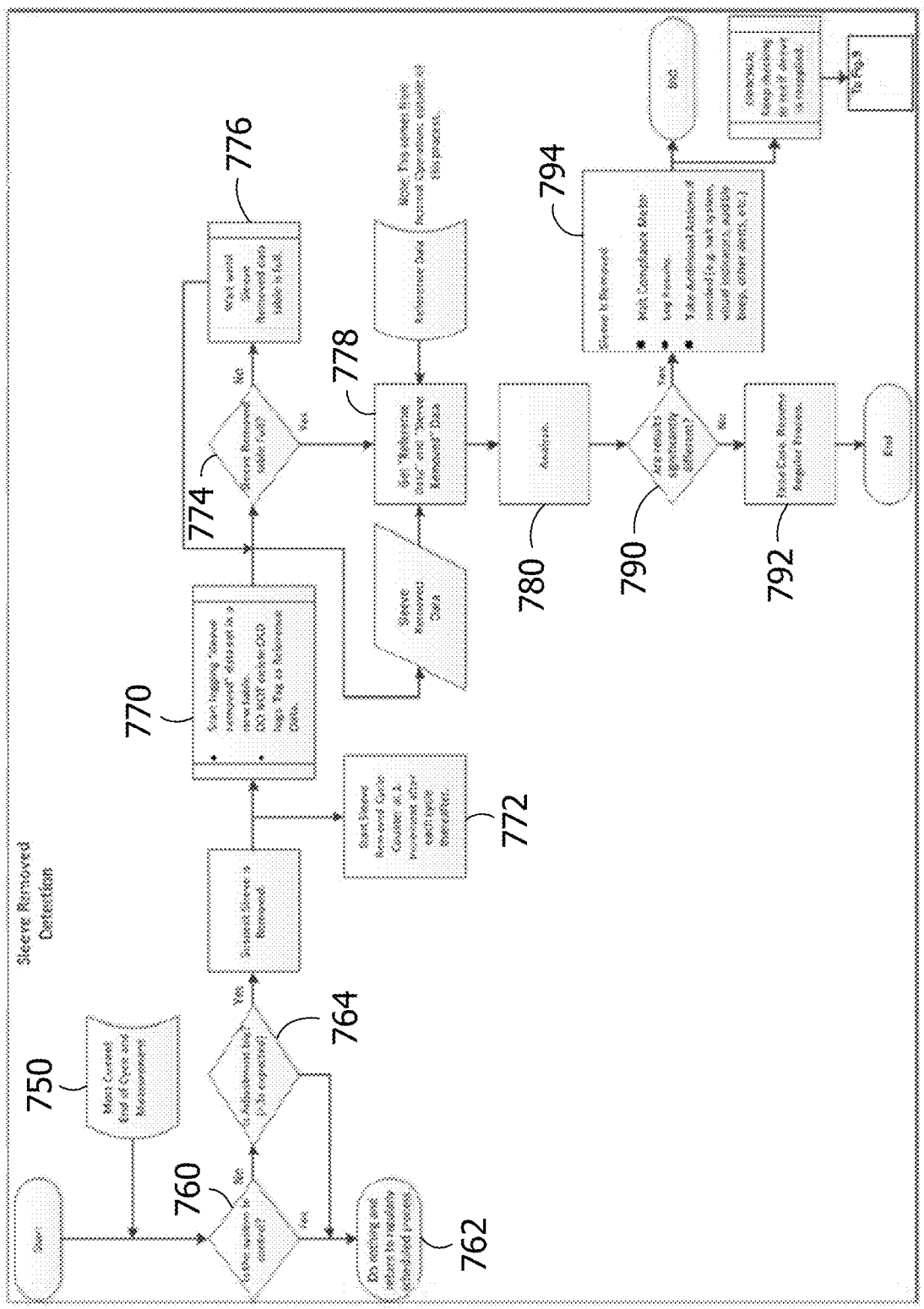
FIGS. 8 and 9 are flow diagrams of exemplary implementations of the compliance monitoring method of FIG. 7.
Figure 9:
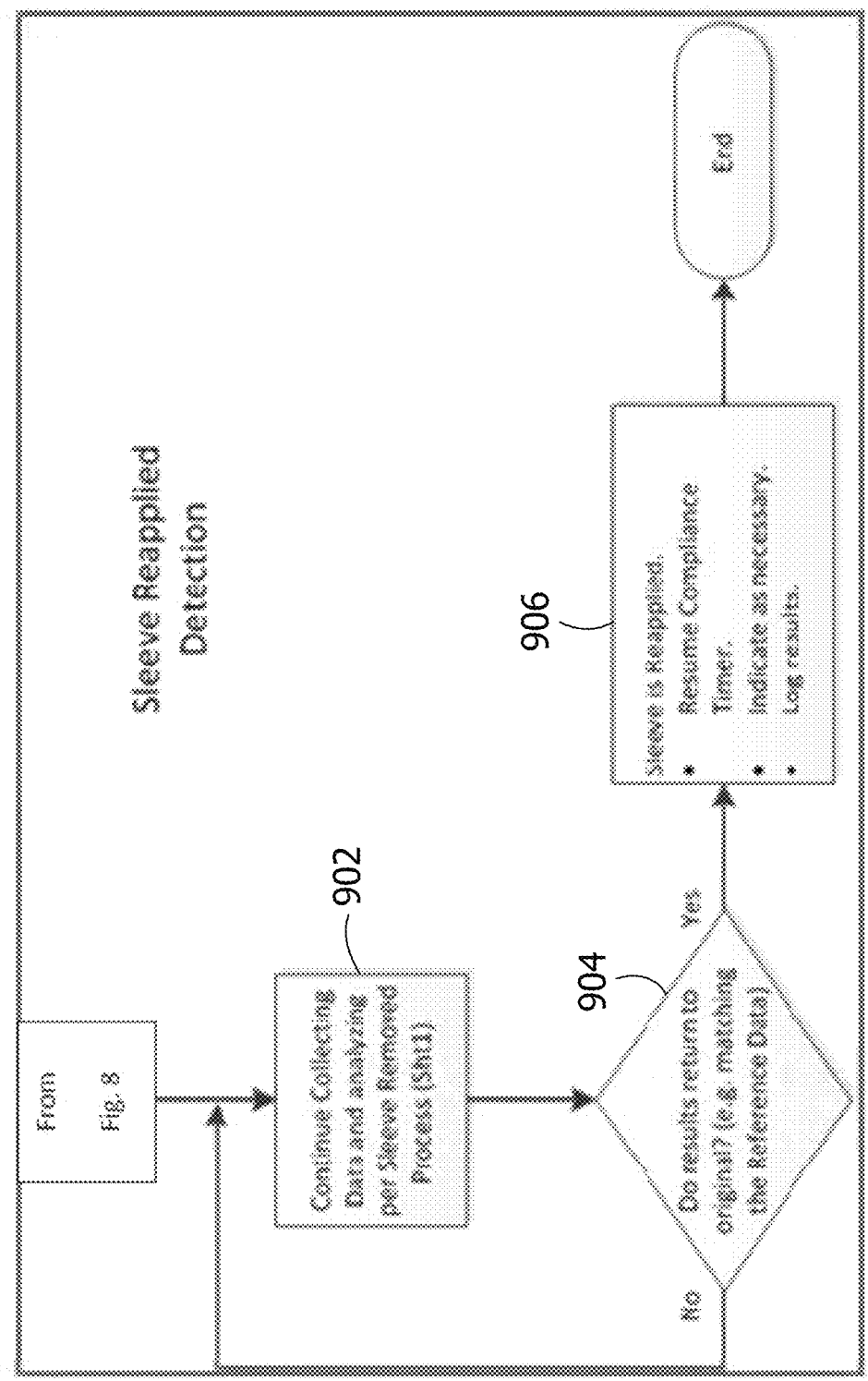

Referring to FIGS. 7-9, the computer executable instructions embodied on the computer readable storage medium 33 cause the one or more processors 7 to execute a method 740 of determining whether the compression garment 10 is in the wrapped or unwrapped configuration when compression therapy is being applied. The steps set forth in FIG. 7 describe the method of determining whether the compression garment 10 is in the wrapped or unwrapped configuration at a generally high level, and FIGS. 8 and 9 describe the method in greater detail. Reference will be made to all three of the figures in describing the compliance method executed by the one or more processors 7.

Referring to FIGS. 7 and 8, at the start of the compliance determination method 740, the compression system 1 operates to sequentially inflate and deflate the bladders 13a, 13b, 13c to apply compression treatment to a wearer's limb. The treatment is preferably made according to a predetermined compression regimen, which includes among other things, a prescribed period of time in which the patient should receive the treatment. Compliance of the patient with the prescribed treatment time is monitored. The compression system 1 is operated for several or more cycles as needed to allow the system to settle into a steady state and to collect steady state data before compliance determination begins. However, a compliance timer or counter can be started prior to onset of compliance determination. Thus, at the start of the compliance determination method 740 the compression garment 10 is in the wrapped configuration and operating under a normal (steady state) operating condition. The system 1 operates at step 750 under default conditions where the one or more processors 7 instruct the pressure sensor 27 to measure the pressure in the manifold 29 throughout the compression cycle. Pressure data is discarded over time and replaced with new more recent pressure data as it becomes available. The one or more processors 7 check at 760 for the occurrence of a trigger suggesting that the compression garment 10 may have been unwrapped.

In general, a trigger may occur when a measured result differs from an expected result, with the expected result based on the most recent adjustment history and steady state control error(s). A trigger may include, for example and without limitation one or more of the following: an end of cycle pressure change from the previous compression cycle(s) for at least one of the bladders 13a, 13b, 13c; an end of inflation pressure change from the previous compression cycle(s) for at least one of the bladders 13a, 13b, 13c; an adjustment of pump 21 caused by said pressure (e.g., an error in the target measurement); a curvature coefficients change from the previous inflation phase(s) of at least one of the bladders 13a, 13b, 13c; an inflation phase slope change from the previous compression cycle(s) for at least one of the bladders 13a, 13b, 13c; a change in the measured pressure of one or more of the bladders at the end of a cycle of operation, a change in the slope of measured pressure during the vent phase, a change in the initial offset of measured pressure from zero from the previous compression cycle(s); a pressure in one of the inflatable bladders 13b, 13c having a lower target pressure exceeding the pressure in another of the inflatable bladders 13a, 13b having a higher target pressure, a smaller difference in peak pressure between bladders 13a and 13b, a change in the magnitude of adjustment made to operation of the pump 21, a statistically significant change the pressure waveform and any unplanned disturbances in the measured pressures or unplanned adjustments made by the compression system 1.

Referring to FIG. 8, until a trigger occurrence is detected, the compression system 1 continues normal operation (step 762). If a trigger occurrence is detected, a determination is made at 764 whether the occurrence exceeds a predetermined condition such as, for example, an expected error for steady state operation. Additionally or alternatively, a pressure change/disturbance producing a control system response greater than three times that of an expected change/disturbance could serve as a predetermined condition. An "expected change/disturbance" could be pre-set or could be criteria established by the controller 5 through operation of the controller in a steady state for a period of time. Additionally or alternatively, an adjustment to pump 21 that is greater than a predetermined threshold as compared to a most recent adjustment could serve as a predetermined condition. For example, a trigger may occur when a new adjustment of pump 21 is greater than 100% of the previous adjustment. The compression system 1 continues 762 normal operation if it is determined that the trigger occurrence does not exceed the predetermined threshold or satisfy the criteria.

Referring to FIGS. 7 and 8, data gathering is begun at 770 if it is determined that the trigger occurrence is valid for use in confirming that a change in condition of the compression garment 10 from wrapped to unwrapped has occurred. The one or more processors 7 activate a "sleeve removed" compression cycle counter at 772 for counting a number of "sleeve removed" compression cycles for which data is gathered to confirm the trigger occurrence as an indication that the garment 10 has become unwrapped. The number of "sleeve removed" compression cycles are counted at 774 until a sufficient amount of data (i.e., pressure signals) is obtained. The number of "sleeve removed" compression cycles needed to obtain a sufficient amount of data to determine whether the garment 10 is in the unwrapped configuration can be different under different circumstances. In one embodiment, the number of "sleeve removed" compression cycles is between about ten to about twenty compression cycles. Generally, a sufficient amount of data is determined to be obtained when the pressure signals again reach a steady state after the initial trigger occurrence. The memory 33 stores the data associated with the "sleeve removed" cycle separately from the reference data obtained during normal operation of the system 1. Once enough data is obtained at 776, the one or more processors 7 retrieve the data obtained during the normal operation of the system 1 at step 778. The one or more processors 7 analyze the "sleeve removed" data after the pressure signals reach the steady state at 780 to determine bladder pressure values for comparing to the data obtained while the compression system 1 was operating in the normal condition.

The one or more processors 7 determine at step 790 whether the garment 10 is in the wrapped or unwrapped condition by comparing the "sleeve removed" data to the normal operating condition reference data. The compression system 1 continues normal operation if the one or more processors 7 determine at 792 that the garment 10 has not been removed and is still in the wrapped configuration. The one or more processors 7 alter recordation of a monitored parameter if it is determined at 794 that the garment 10 has been removed, placing the garment in an unwrapped configuration. Comparing the "sleeve removed" data to the normal operating condition data at step 790 can include without limitation one or more of: comparing the end of cycle pressure from the "sleeve removed" data to the end of cycle pressure from the normal operating condition data for at least one of the bladders 13a, 13b, 13c; comparing an end of inflation pressure from the "sleeve removed" data to the end of inflation pressure from the normal operating condition data for at least one of the bladders 13a, 13b, 13c; comparing curvature coefficients from a curve fit on "sleeve removed" data to curvature coefficients from a curve fit on normal operating condition data; comparing an inflation phase slope from the "sleeve removed" data to the inflation phase slope from the normal operating condition data for at least one of the bladders 13a, 13b, 13c; comparing the initial offset of measured pressure from zero on the "sleeve removed" data to the initial offset of measured pressure from zero from the normal operating condition data; comparing a vent phase slope from the "sleeve removed" data to a vent phase slope from the normal operating condition data for at least one of the bladders 13a, 13b, 13c; comparing measured pressures to determine if an inflatable bladder having a lower target pressure has a higher measured pressure than the measured pressure of an inflatable bladder having a higher target pressure; comparing the differences in peak pressures of inflatable bladders 13a, 13b from the "sleeve removed" data to the difference in peak pressures of the bladders 13a, 13b in the normal operating condition data for a decrease in the difference; comparing the magnitude of adjustments to operation of the pump 21 in the "sleeve removed" data to the magnitude of adjustments made in the normal operation data; looking for statistically significant differences in the pressure waveform between the "sleeve removed" data and the normal operation data. For instance, a pressure spike during the vent phase of one of the bladders 13a, 13b, 13c is an indication that the garment 10 is in the wrapped configuration. The comparing step 790 is a confirmatory analysis for confirming the trigger occurrence as an indication that the garment is in the unwrapped configuration.

If the data comparisons 790 indicate that a statistically significant change in pressure occurred for any one of the data comparisons, and for any one of the bladders 13a, 13b, 13c, the one or more processors 7 indicate that the garment 10 is in the unwrapped configuration and is no longer being used in a compliant manner. Additionally or alternatively, the one or more processors 7 require confirmation from at least two of the bladders 13a, 13b, 13c that a statistically significant change in pressure occurred for any one of the data comparisons. Additionally or alternatively, the one or more processors 7 require confirmation from all of the bladders 13a, 13b, 13c that a statistically significant change in pressure occurred for any one of the data comparisons. Additionally or alternatively, the one or more processors 7 require confirmation that a statistically significant change in pressure occurred for at least two of the data comparisons.

In response to a confirmation of a pressure change, the one or more processors 7 alter recordation of the monitored parameter at step 794 by at least one of halting a compliance meter so that no further compression cycles are indicated as being compliant with a compression therapy regimen (e.g., a compliance timer stops incrementing), providing an alarm indication alerting the wearer or clinician of the noncompliance, halting operation of the compression system 1, and storing the results of the comparison in the memory 33 (e.g., a flag).

Optionally, referring to FIG. 9, the method 740 of determining whether the compression garment 10 is in the wrapped or unwrapped configuration continues by collecting at step 902 additional "sleeve removed" data after the determination is made by the one or more processors 7 that the garment 10 is in the non-compliant, unwrapped configuration. The one or more processors 7 analyze and compare at 904 the additional "sleeve removed" data to the normal operating condition data. The one or more processors 7 determine at 906 that the garment 10 has returned to the wrapped configuration and is again being used in a compliant manner if the data comparisons at 904 indicate that the additional "sleeve removed" data matches or closely matches the normal operating condition data for any one of the bladders 13a, 13b, 13c. In response, the one or more processors 7 alter recordation of the monitored parameter by at least one of resuming operation of the compression system 1, resuming a compliance meter so that subsequent compression cycles are indicated as being compliant, providing a message alerting the wearer or clinician of the compliance, and storing the results of the comparison in the memory 33. The one or more processors 7 continue to collect at 902 additional "sleeve removed" data until the one or more processors 7 determine that the pressure signals, such as the measures described above, match or closely match the normal operating condition pressure signal if the data comparisons at 904 indicate that a statistically significant change in pressure remains for any one of the data comparisons.

As can be seen from FIGS. 4 and 5, the pressure measurement produced by the pressure sensor 27 is slightly higher than the actual pressure within the bladder 13a, 13b, 13c. For the purposes of using the pressure sensor signal to determine compliance, the difference in pressures is negligible. Alternatively, by briefly deactivating the fluid source 21 the pressure measured by the pressure sensor 27 normalizes to the actual pressure in the bladder in fluid communication with the manifold 29.

Additionally or alternatively, the linear regression for the inflation phases of the bladders 13a, 13b, 13c can be further analyzed for comparing between the wrapped and unwrapped conditions. For instance, standard deviation, P-values, max and min values, and an average value can be calculated and compared between the wrapped and unwrapped conditions to further distinguish between the two conditions. Advanced statistics associated with regression analyses (e.g. the curve fitting analysis described herein), such as analysis of residuals, for distinguishing sleeve-on and sleeve-off conditions is also within the scope of the present disclosure.

Figure 10:
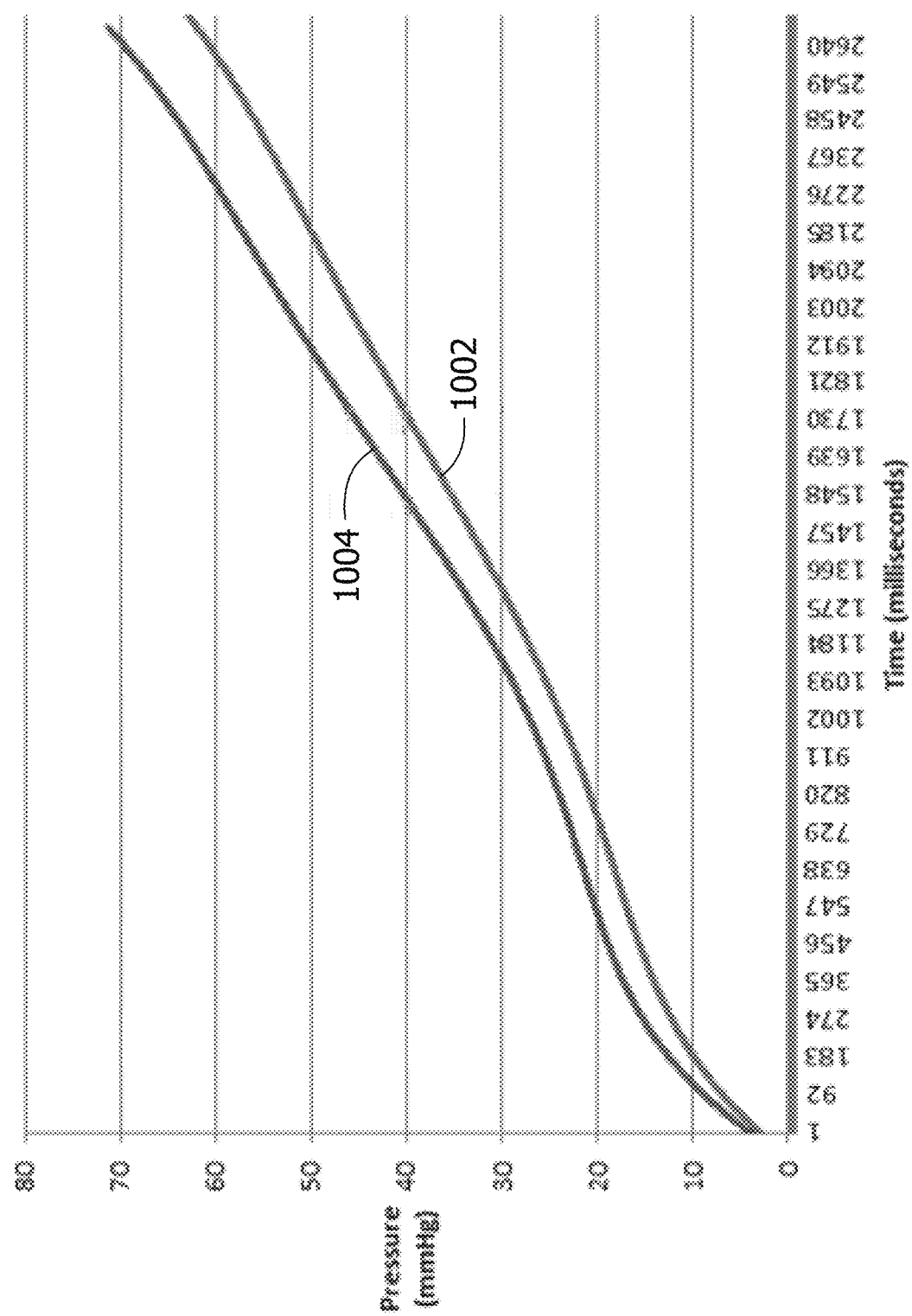
FIG. 10 is a graphical representation of polynomial curve fit lines of the pressure in the manifold during an inflation phase of a bladder of the compression garment in both the wrapped and unwrapped configurations.

While the curve fits for the inflation phase of the bladders 13a, 13b, 13c have been described as best fit lines, the models could be polynomial curve fits. Referring to FIG. 10, pressure signals from the inflation phase of bladder 13a are modeled with a fifth order polynomial curve fit in the wrapped configuration (1002) and the unwrapped configuration (1004). The fifth order polynomial curve fit accurately represents more dynamic curvature of the inflation phases without being overly responsive to the changes in the pressure signals. Other order polynomial curve fits are also envisioned. As an example, lower orders can be used such as when the curvature is less dynamic and higher orders are not required.

The polynomial curve fits during the inflation phases of the bladders 13a, 13b, 13c in the wrapped configurations are generally straighter (i.e., more linear) than the polynomial curve fits for the inflation phases of the bladders 13a, 13b, 13c in the wrapped configuration. Additionally, for the distal and intermediate bladders 13a, 13b, the pressures throughout the inflation phase in the unwrapped configuration are higher than the pressures throughout the inflation phase in the wrapped configuration. The reverse condition is true for the proximal bladder 13c where the pressures throughout most of the inflation phase in the wrapped configuration are higher than the pressures throughout most of the inflation phase in the unwrapped configuration. Additionally, the starting pressures, or offset, for the bladders 13a and 13b, in the unwrapped configuration are higher than the starting pressures for the bladders 13a and 13b in the wrapped configuration. By recognizing the occurrence of these differing characteristics the compression system 1 can determine when the garment 10 is in a compliant, wrapped configuration and when the garment 10 is in a non-compliant, unwrapped configuration.

Additionally or alternatively, the polynomial curve fits for the inflation phases of the bladders 13a, 13b, 13c can be further analyzed for comparing between the wrapped and unwrapped conditions. For instance, standard deviation, P-values, max and min values, and an average value can be calculated and compared between the wrapped and unwrapped conditions to further distinguish between the two conditions. Advanced statistics associated with regression analyses (e.g. the curve fitting analysis described herein), such as analysis of residuals, for distinguishing sleeve-on and sleeve-off conditions is also within the scope of the present disclosure.

Figure 11:
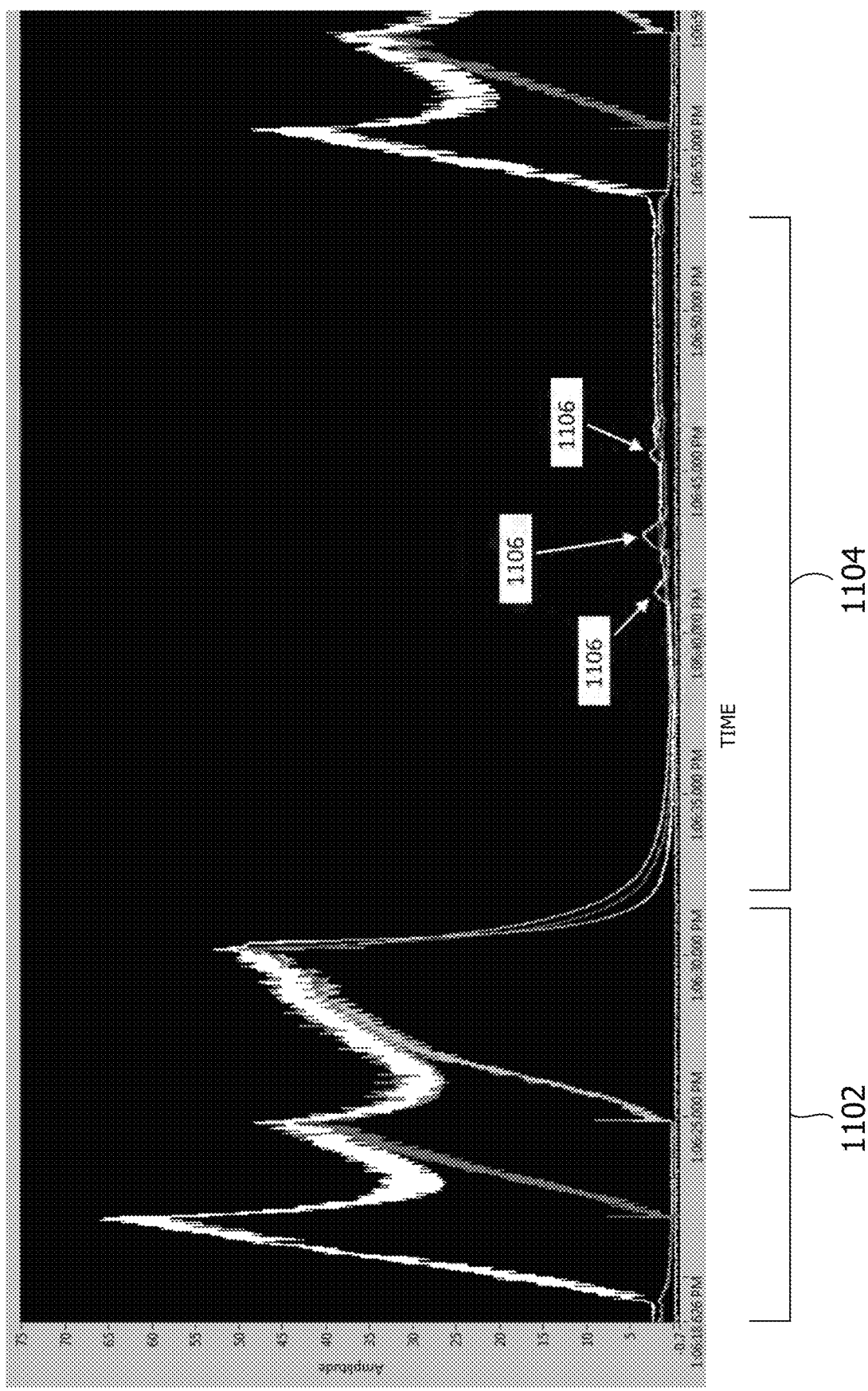
FIG. 11 is a graphical representation of a pressure profile produced by the compression system of FIG. 1 when the compression garment is in a wrapped configuration on a limb of a wearer.
Figure 12:
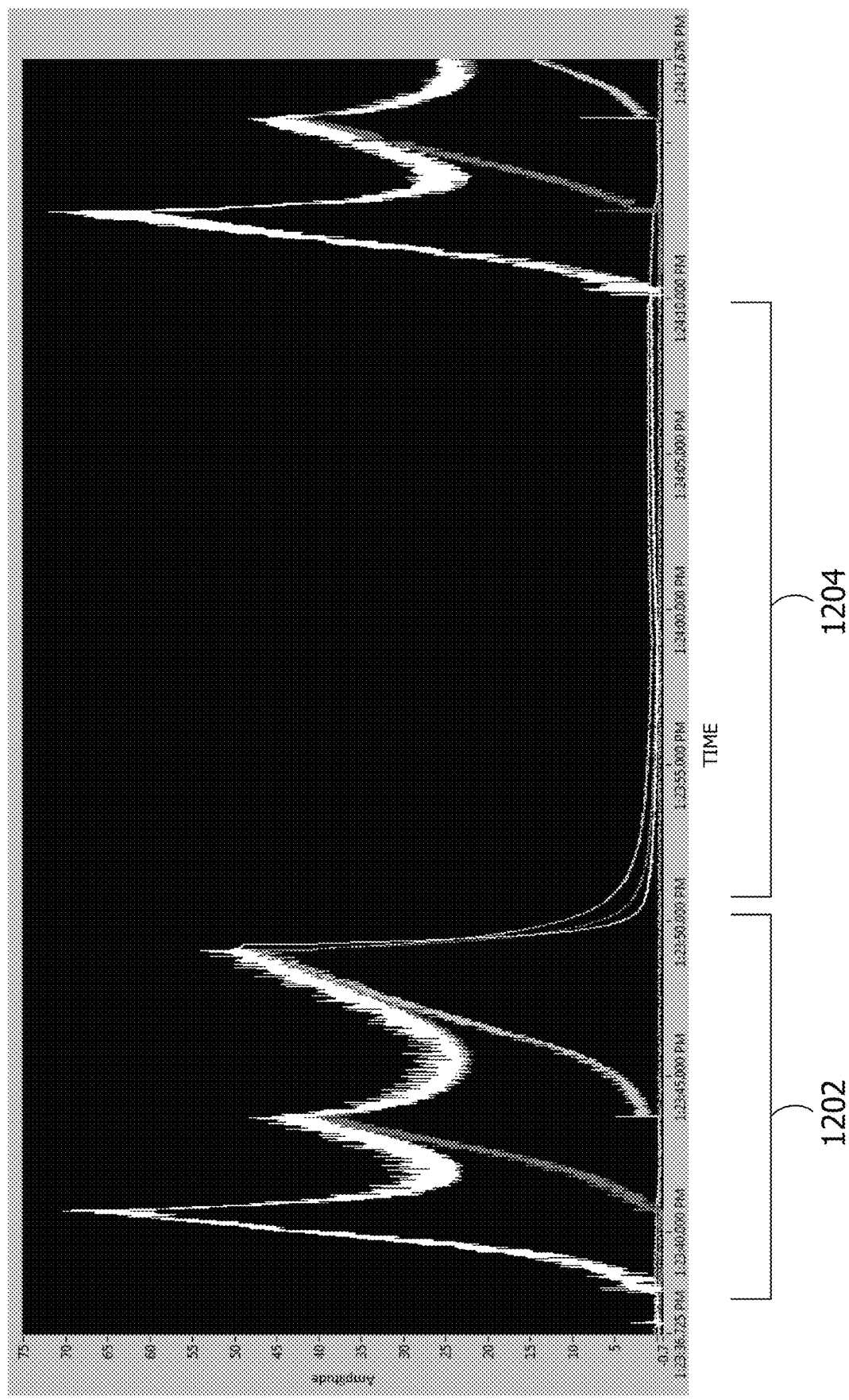
FIG. 12 is graphical representation of a pressure profile produced by the compression system of FIG. 1 when the compression garment is in an unwrapped configuration and away from a limb of a wearer.

Referring to FIG. 11, a representative compression cycle pressure profile for a wrapped configuration of the compression garment 10 is illustrated. This graph illustrates signals from the pressure sensor 27. A single compression cycle for all three of the bladders 13a, 13b, 13c in a wrapped configuration of the compression garment 10 includes a compression period 1102 and a decompression period 1104. Referring to FIG. 12, a representative compression cycle pressure profile for an unwrapped configuration of the compression garment 10 is illustrated. A compression period 1202 and a decompression period 1204 illustrate a single compression cycle for all three of the bladders 13a, 13b, 13c for the unwrapped configuration of the compression garment 10. The computer executable instructions embodied on the computer readable storage medium 33 include instructions to cause the one or more processors 7 to monitor the signals from the pressure sensor 27 that are indicative of the bladder pressures during the decompression periods 1104, 1204. The computer executable instructions cause the one or more processors 7 to detect a difference between the pressure signal of decompression period 1104 and the pressure signal of decompression period 1204. For example, the pressure signal during the decompression period 1104 includes pressure impulses, indicated generally at 1106 in FIG. 11, which the controller 5 interprets as indicative of wearer movement when the compression garment 10 is in a wrapped configuration. The pressure signal during the decompression period 1204 is relatively static (i.e., no impulses are present) which the controller 5 interprets as indicative of the compression garment 10 being in an unwrapped configuration. By analyzing the pressure signals of the decompression periods 1104, 1204, the computer executable instructions cause the one or more processors 7 to determine whether or not the compression garment 10 is in a wrapped configuration or unwrapped configuration based on the presence (i.e., occurrence) or absence (i.e., non-occurrence) of one or more pressure impulses 1106 during the decompression periods 1104, 1204.

Referring again to FIG. 11, in another embodiment of the compression system 1, bladder pressures of the bladders 13a, 13b, 13c are locked and the computer executable instructions cause the one or more processors 7 to detect a rise (e.g., increase) in the pressure signal during the decompression period 1104 when the compression garment 10 is in a wrapped configuration substantially around a limb of a wearer. The pressure signal during the decompression period 1204 (FIG. 12) is relatively static (i.e., no pressure rise is present) which the controller 5 interprets as indicative of the compression garment 10 being in an unwrapped configuration. The computer executable instructions cause the one or more processors 7 to determine whether the compression garment 10 is in a wrapped or unwrapped configuration based on the presence (i.e., occurrence) or absence (i.e., non-occurrence) of a pressure rise during the decompression periods 1104, 1204.

Figure 13:
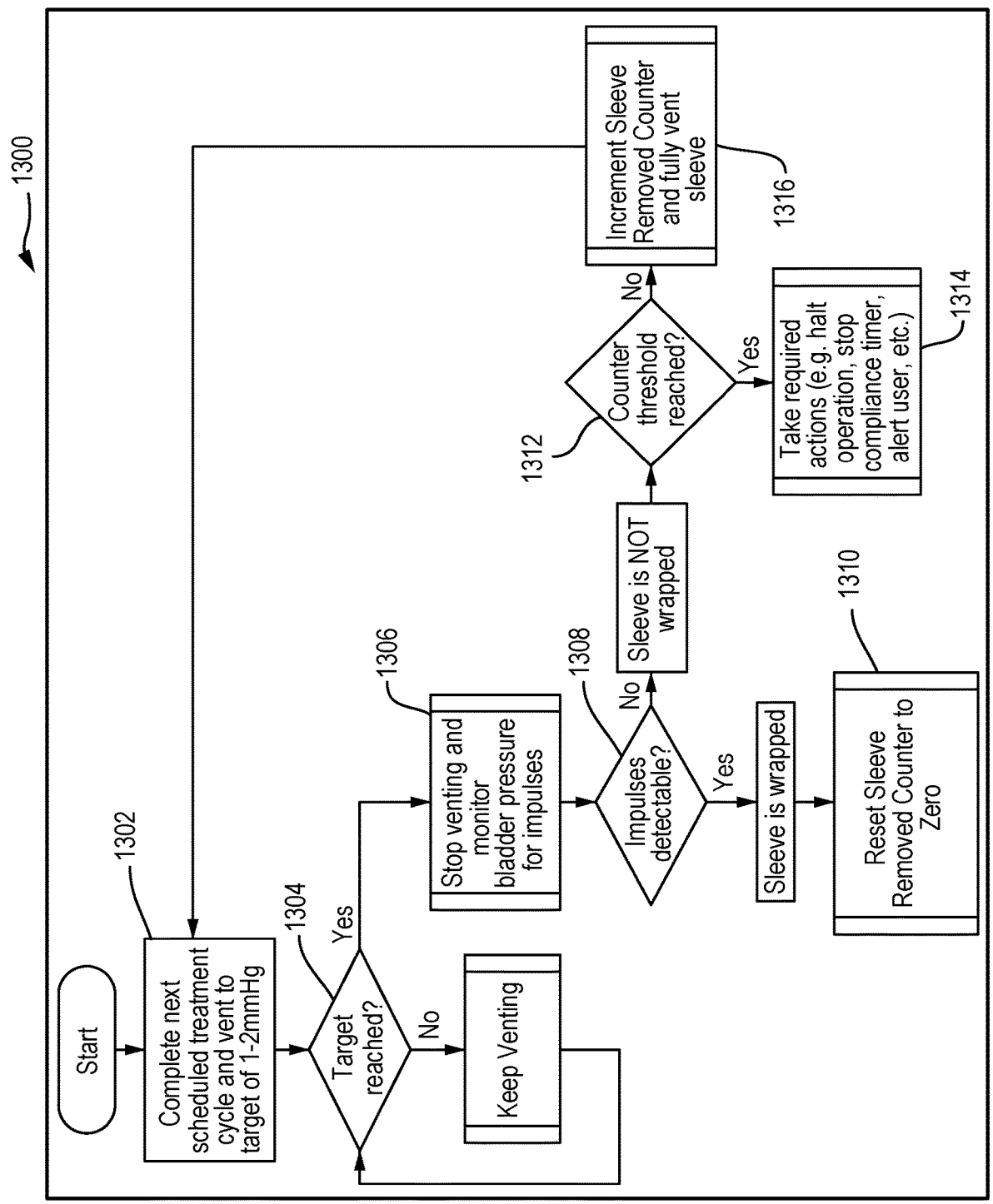
FIGS. 13 and 14 are flow diagrams of methods of compliance monitoring using the compression system of FIG. 1.

Referring to FIG. 13, the computer executable instructions embodied on the computer readable storage medium 33 cause the one or more processors 7 to execute a method 1300 of determining whether the compression garment is in the wrapped or unwrapped configuration by detecting one or more pressure impulses in the pressure signal received from the pressure sensor 27. The compression system 1 operates at step 1302 to inflate and deflate bladders 13a, 13b, 13c to apply compression treatment to a wearer's limb, and to vent the bladders 13a, 13b, 13c down to a target value, such as 1-2 mmHg. The computer executable instructions cause the one or more processors 7 to determine at step 1304 whether the pressure in the bladders 13a, 13b, 13c has reached the target value. If the target value has not been reached, the computer executable instructions cause the one or more processors 7 to continue venting the bladders 13a, 13b, 13c and the process returns back to step 1304. If the target value has been reached, the computer executable instructions cause the one or more processors 7 to stop venting the bladders 13a, 13b, 13c and monitor the pressure signal from pressure sensor 27 for impulses during the decompression period at step 1306. It is appreciated that a filtered signal may be assumed such that any impulse observed would be above baseline signal noise without departing from the scope of the present disclosure. The signal may be filtered, for example, by filtering circuitry in controller 5 and/or by digital filtering techniques implemented by the one or more processors 7 via the computer executable instructions. It is appreciated that the computer executable instructions may cause the one or more processors 7 to perform waveform peak detection to determine the amplitude of anomalous peaks versus peaks within the expected noise without departing from the scope of the present disclosure. It is also appreciated that the computer executable instructions may cause the one or more processors 7 to utilize signal threshold limit detection without departing from the scope of the present disclosure. For example, if an impulse greater than 1 mmHg above noise is detected, then that impulse is considered a pressure impulse. The computer executable instructions cause the one or more processors 7 to implement a counter, with which a count is kept for the number of consecutive cycles in which no impulses are observed.

At step 1308, the computer executable instructions cause the one or more processors 7 to determine whether an impulse was detected by the processor 7 at step 1306. If an impulse was detected during step 1306, the computer executable instructions cause the one or more processors 7 to reset 1310 the counter to zero because the impulse is indicative of the compression garment 10 being in a wrapped configuration substantially around a limb of a wearer. If an impulse was not detected during step 1306, then such a nonoccurrence (i.e., absence) of an impulse is indicative of the compression garment 10 being in an unwrapped configuration away from a limb of a wearer. In such a case, the computer executable instructions cause the one or more processors 7 to determine whether the count of the counter has met or exceeded a counter threshold at step 1312. For example, the threshold may be ten consecutive cycles, but one skilled in the art will appreciate that the threshold may be any integer value. Meeting or exceeding the threshold indicates that the compression garment 10 is in the unwrapped configuration away from the limb of the wearer because a pressure anomaly (e.g., pressure impulse) would have been detected by the one or more processors 7 if the compression garment 10 were in the wrapped configuration.

If the one or more processors 7 determine at step 1312 that the count of the counter has met or exceeded a counter threshold, then the computer executable instructions cause the one or more processors to take a required action at step 1314. For example, the one or more processors 7 may halt operation, stop a compliance timer, alert a user (e.g., the wearer or caregiver), and the like. If the one or more processors 7 determine at step 1312 that the count of the counter has not reached the counter threshold, then the computer executable instructions cause the one or more processors 7 to increment the count of the counter and fully vent the bladders 13a, 13b, 13c at step 1316 and the process returns to step 1302.

In an alternative embodiment, the method 1300 of FIG. 6 is implemented during Venous Refill Measurements. In such an embodiment, bladder 13b is vented to a higher pressure (e.g., 5-7 mmHg) and therefore is more firmly in contact with the limb of the wearer. In this embodiment, pressure impulses due to patient movement are even more evident in the pressure signal of pressure sensor 27.

Figure 14:
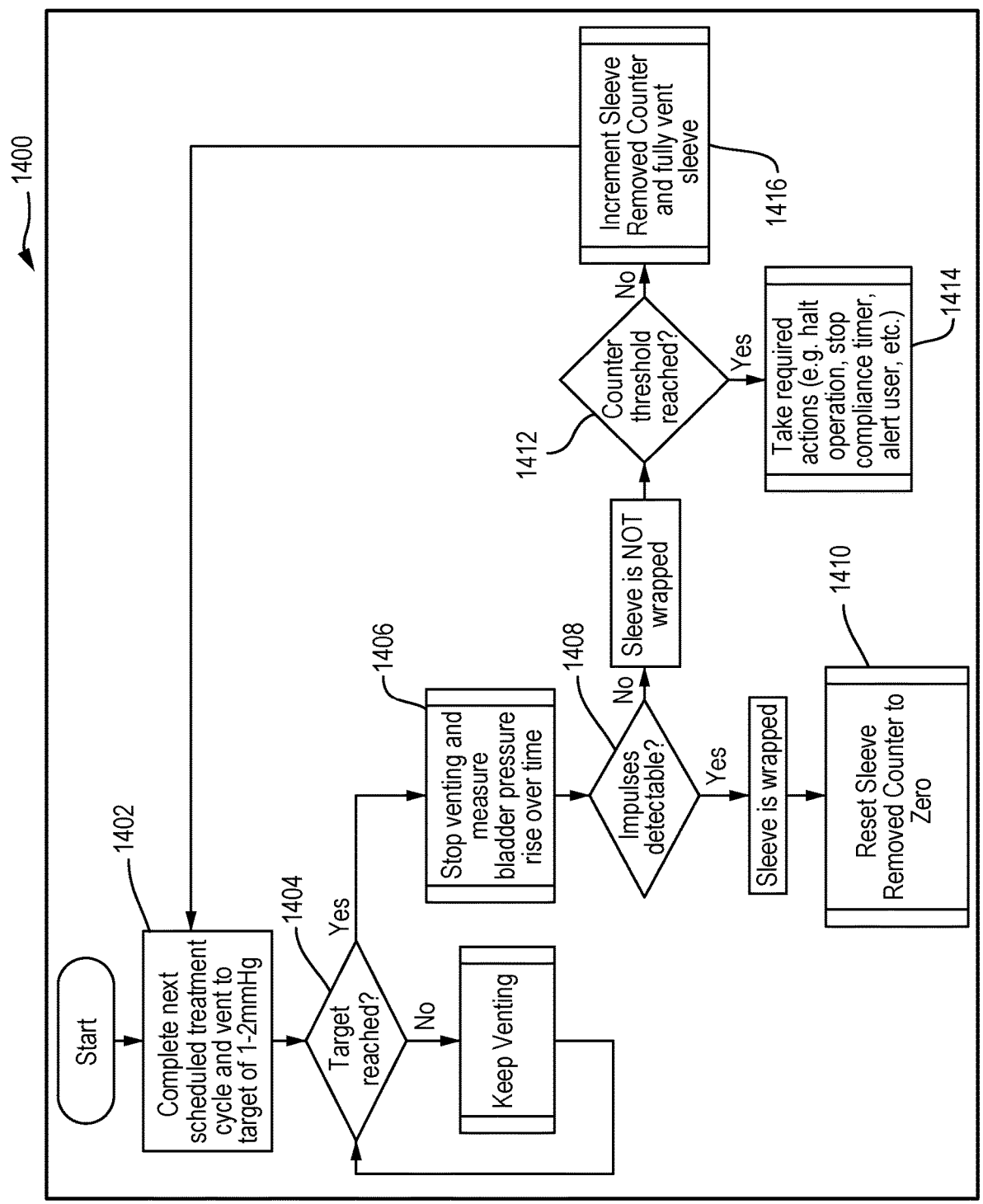

Referring to FIG. 14, the computer executable instructions embodied on the computer readable storage medium 33 cause the one or more processors 7 to execute a method 1400 of determining whether the compression garment is in the wrapped or unwrapped configuration by detecting a rise (e.g., increase) in the pressure signal received from the pressure sensor 27. The compression system 1 operates at step 1402 to inflate and deflate bladders 13a, 13b, 13c to apply compression treatment to a wearer's limb, and to vent the bladders 13a, 13b, 13c down to a target value, such as 1-2 mmHg. The computer executable instructions cause the one or more processors 7 to determine at step 1404 whether the pressure in the bladders 13a, 13b, 13c has reached the target value. If the target value has not been reached, the computer executable instructions cause the one or more processors 7 to continue venting the bladders 13a, 13b, 13c and the process returns to step 1404. If the target value has been reached, the computer executable instructions cause the one or more processors 7 to stop venting the bladders 13a, 13b, 13c and monitor the pressure signal from pressure sensor 27 for a rise during the decompression period at step 1406. In an embodiment, a filtered signal is assumed such that any rise observed would be above baseline signal noise. The signal may be filtered for example, by filtering circuitry in controller 5 and/or by digital filtering techniques implemented by the one or more processors 7 via the computer executable instructions. The one or more processors 7 monitor the pressure signal for a pressure rise greater than a threshold value (e.g., 1-2 mmHg), which indicates that the compression garment 10 is in a wrapped configuration substantially around a limb of a wearer. A lack of a rise in the pressure signal, or a rise less than the threshold value, indicates that the compression garment 10 is in an unwrapped configuration away from a limb of a wearer. The computer executable instructions cause the one or more processors 7 to implement a counter, with which a count is kept for each cycle failing to achieve the threshold pressure rise.

At step 1408, the computer executable instructions cause the one or more processors 7 to determine whether a pressure rise greater than the threshold value was detected by the processor 7 at step 1406. If a pressure rise greater than the threshold was detected during step 1406, the computer executable instructions cause the one or more processors 7 to reset 1410 the counter to zero because the pressure rise is indicative of the compression garment 10 being in a wrapped configuration substantially around a limb of a wearer. If a rise above the threshold was not detected during step 1406, then such a nonoccurrence of a pressure rise is indicative of the compression garment 10 being in an unwrapped configuration away from a limb of a wearer. In such a case, the computer executable instructions cause the one or more processors 7 to determine whether the count of the counter has met or exceeded a counter threshold at step 1412. For example, the threshold may be ten consecutive cycles, but one skilled in the art will appreciate that the threshold may be any integer value. Meeting or exceeding the threshold indicates that the compression garment 10 is in the unwrapped configuration away from the limb of the wearer because a pressure anomaly (e.g., pressure rise) would have been detected by the one or more processors 7 if the compression garment 10 were in the wrapped configuration.

If the one or more processors 7 determine at step 1412 that the count of the counter has met or exceeded a counter threshold, then the computer executable instructions cause the one or more processors to take a required action at step 1414. For example, the one or more processors 7 may halt operation, stop a compliance timer, alert a user (e.g., the wearer or caregiver), and the like. If the one or more processors 7 determine at step 1412 that the count of the counter has not reached the counter threshold, then the computer executable instructions cause the one or more processors 7 to increment the count of the counter and fully vent the bladders 13a, 13b, 13c at step 1416 and the process returns to step 1402.

In alternative embodiment, the actual shape of the pressure profile of the signal generated by pressure sensor 27 is in itself a potential indicator. For example, the shape of the profile could be calculated such that when the resulting function (i.e., the shape) matches a pre-determined function (i.e., shape), the computer executable instructions cause the one or more processors 7 to determine that the compression garment 10 is in the wrapped configuration. Conversely, failure of the resulting function to match the pre-determined function would result in the computer executable instructions causing the one or more processors 7 to determine that the compression garment 10 is in the unwrapped configuration. Such an embodiment may be used with the counters described in conjunction with methods 1300, 1400 described above.

Referring to FIG. 15A, a pressure signal from the pressure sensor 27 is shown for one of the bladders 13a, 13b, 13c in a wrapped configuration of the compression garment 10 on a limb of the wearer during a representative bladder inflation period 1502 and a pressure hold period 1504. In the example in FIG. 15A, the pressure hold period 1504 is about twenty-seven seconds in duration and represents the bladder 13a, 13b, 13c inflated to about 45 mmHg, which is a typical inflation threshold of a therapeutic cycle of the bladders 13a, 13b, 13c. In accordance with another embodiment of the disclosure, the pressure hold period 1504 may be about twenty seconds in duration and represent one of the bladders 13a, 13b, or 13c inflated to about 200 mmHg. Accordingly, the oscillation amplitude in the pressure signal for a bladder inflated to about 200 mmHg will be higher than the oscillation amplitudes illustrated herein associated for a bladder inflated to about 45 mmHg.

Figure 15B:
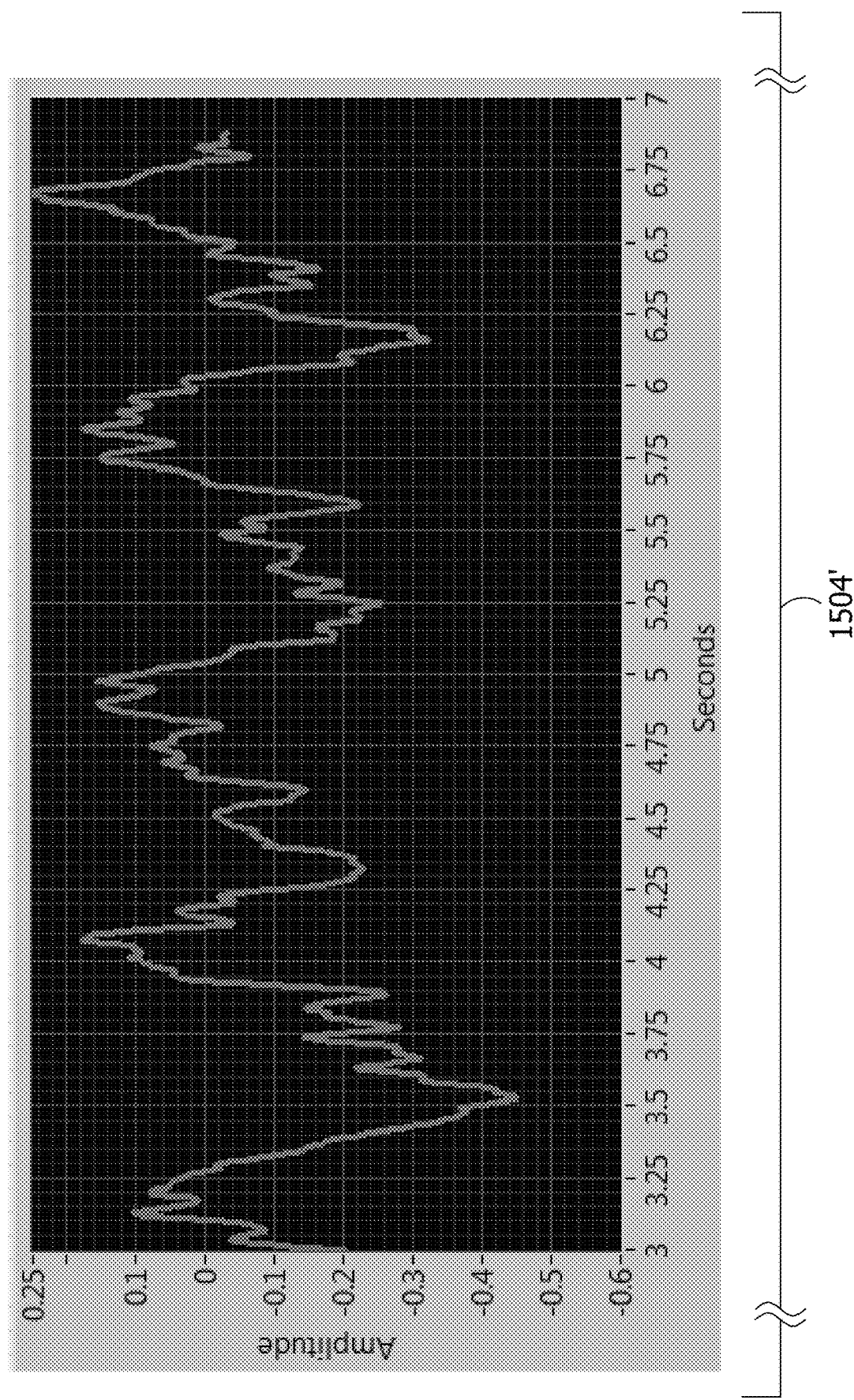

Referring to FIG. 15B, a waveform 1504' shows the result of a band-pass filtering technique applied to a subset signal of interest of the pressure hold period 1504 such that a frequency range (e.g., 0.5 Hz to 25 Hz, 0.5 Hz to 5 Hz, etc.) has been extracted. The representative subset portion of the pressure hold period 1504 is shown on a smaller scale, as compared to FIG. 15A, such that pulses are visible in the pressure signal during the pressure hold period 1504'. The pulses in the pressure pulse in FIG. 15B are associated with a pressure effect produced on the bladder 13a, 13b, or 13c by the pulse of the wearer. Waveform pulsations associated with the pulse of the wearer of the compression garment 10 remain evident in waveform 1504'. The computer executable instructions embodied on the non-transitory, computer readable storage medium 33 include instructions to cause the one or more processors 7 to receive a signal from the pressure sensor 27, the received signal being indicative of the fluid pressure in one or more of the bladders 13a, 13b, 13c during the bladder inflation period 1502 and the pressure hold period 1504.

In certain embodiments, the computer executable instructions further include instructions to cause the one or more processors 7 to refine further the signal from the pressure sensor 27 to extract, during the pressure hold period 1504, only frequencies associated with the typical cardiac cycle range of a human. For example, the computer executable instructions can include computer executable instructions to cause the one or more processors 7 to extract (e.g., through a band-pass filtering technique) frequencies in the range of 0.5 Hz to 25 Hz.

FIG. 15B shows that, as the oscillation amplitude decreases, the impact of noise on the signal is more significant (i.e., the signal-to-noise ratio is smaller). Additional pre-processing and/or post-processing of the data can be useful to obtain less distorted results. In some embodiments, the computer executable instructions further include instructions to cause the one or more processors 7 to filter the signal of the pressure hold period 1504 to remove frequencies that are not associated with a pulse of a human wearer and to cause the one or more processors 7 to implement one or more peak detection algorithms and/or compliance monitoring algorithms. In certain embodiments, the one or more computer executable instructions further include instructions to cause the one or more processors 7 to perform the additional pre-processing and/or post-processing to decrease the impact of noise on the signal received from the pressure sensor 27. It should be appreciated that the signal received from the pressure sensor 27 and processed by the one or more processors 7 includes pulsation associated with the heartbeat of the wearer and not the actual heart rate of the wearer. For example, the blood flow as the wearer's heart beats creates pressure on at least one of inflatable bladders 13a, 13b, 13c, which the pressure sensor 27 detects and generates pressure signals representative thereof.

Figure 15C:
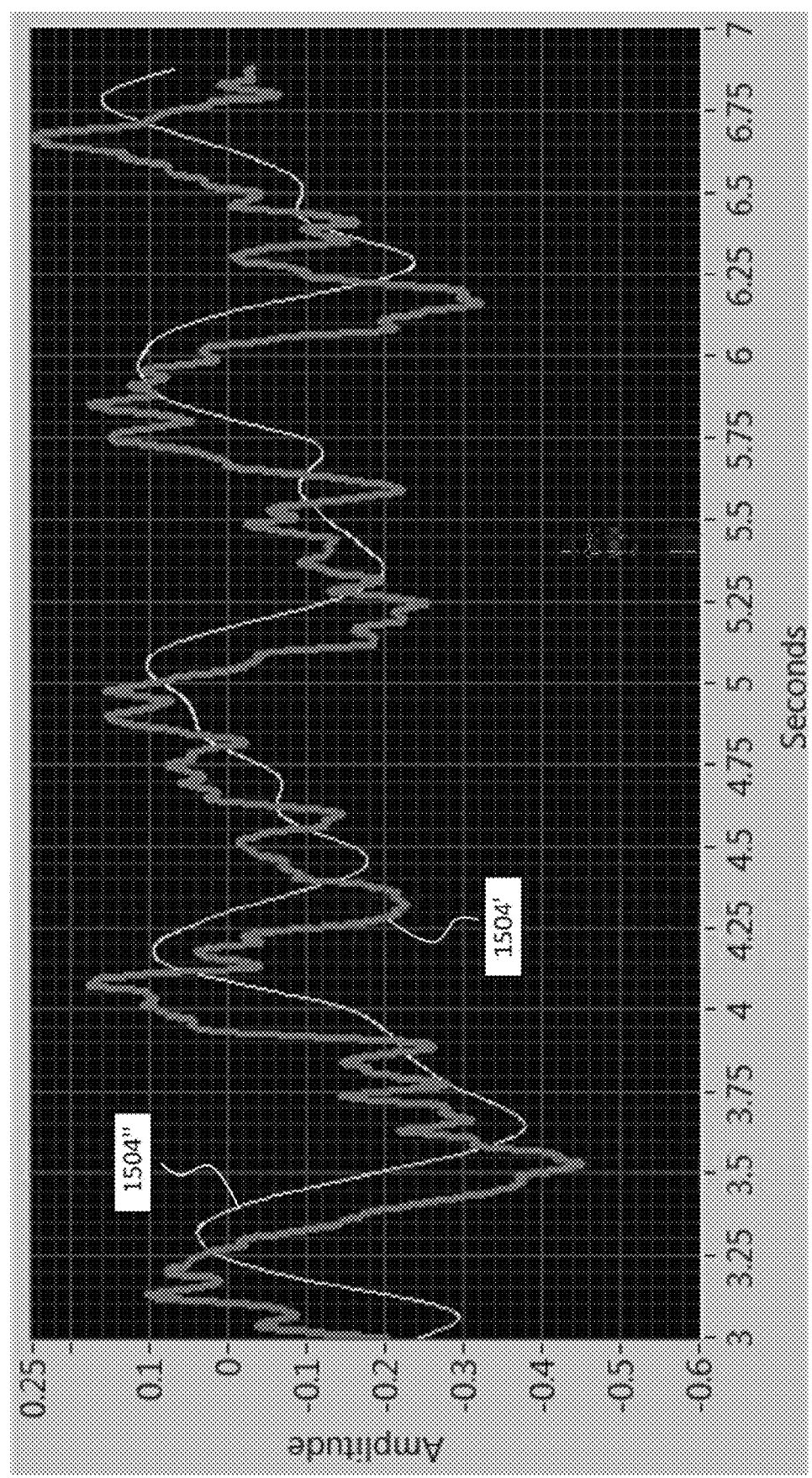

Referring to FIG. 15C, the waveform 1504' is overlaid on a waveform 1504", the waveform 1504" being the result of a smoothing algorithm filtering technique applied to waveform 1504' by the one or more processors 7. In this exemplary embodiment in FIG. 15C, the smoothing follows a rectangular window at five times (e.g., 5×) the moving range. Even at pressures as low as those associated with typical Venous Refill Detection (VRD) techniques (e.g., about 5 to about 20 mmHg), the waveform still provides evidence of pulsations indicative of sufficient contact between the wearer and the compression garment 10.

Figure 16:
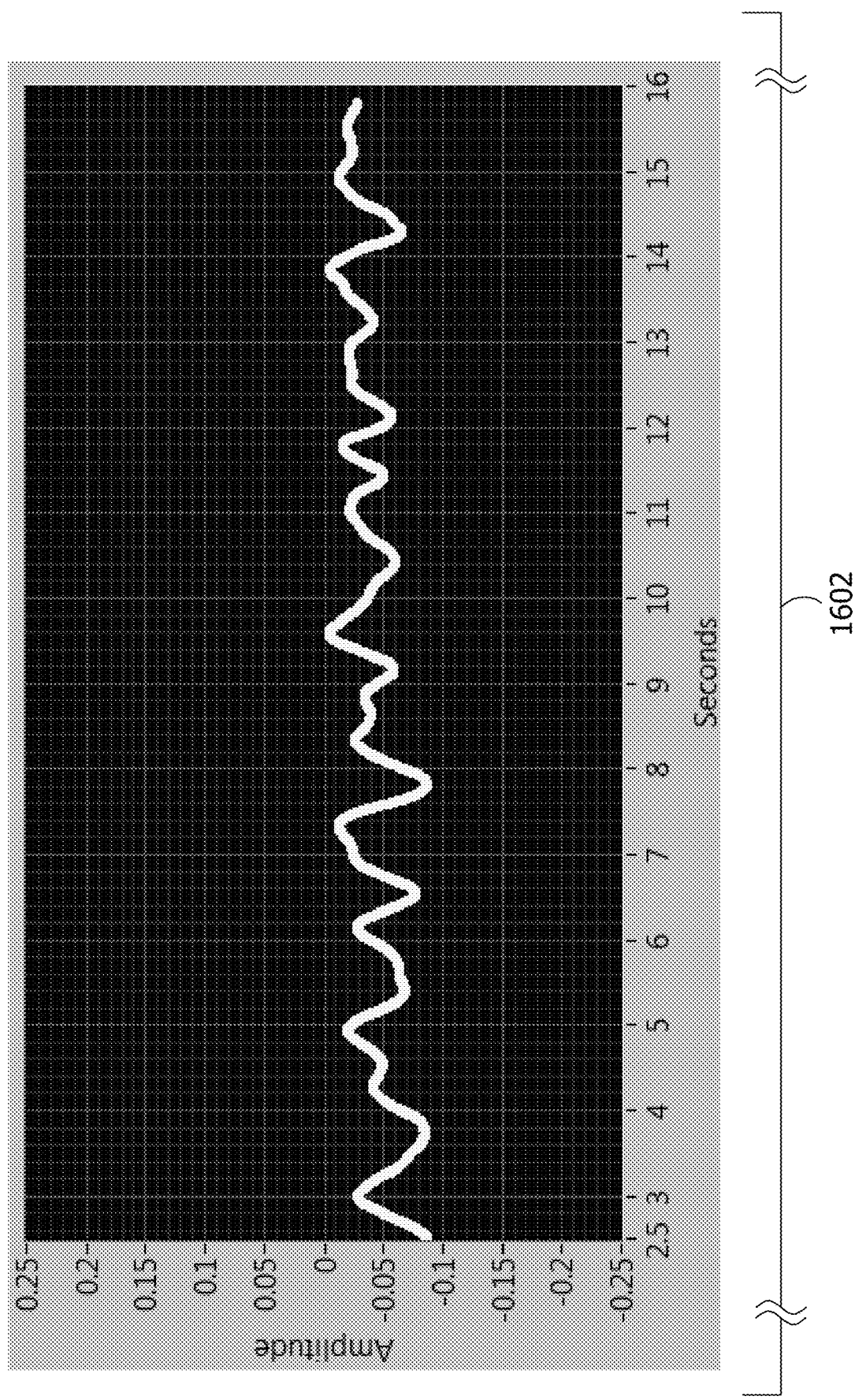
FIG. 16 is graphical representation of another pressure profile produced by the compression system of FIG. 1 when the compression garment is in an unwrapped configuration and away from a limb of a wearer.

FIG. 16 shows a pressure signal received from the pressure sensor 27 during a representative bladder pressure hold period 1602 pressure profile of one of the bladders 13a, 13b, 13c for an unwrapped configuration of the compression garment 10. The overall amplitude of the pressure profile 1602 is less than the amplitudes of the analogous pressure hold period 1504 (shown in FIG. 15A). The absence of clear, repeating pulses in the pressure profile 1602 is an indication that the compression garment 10 is in an unwrapped configuration or is not properly worn by the wearer.

Figure 17A:
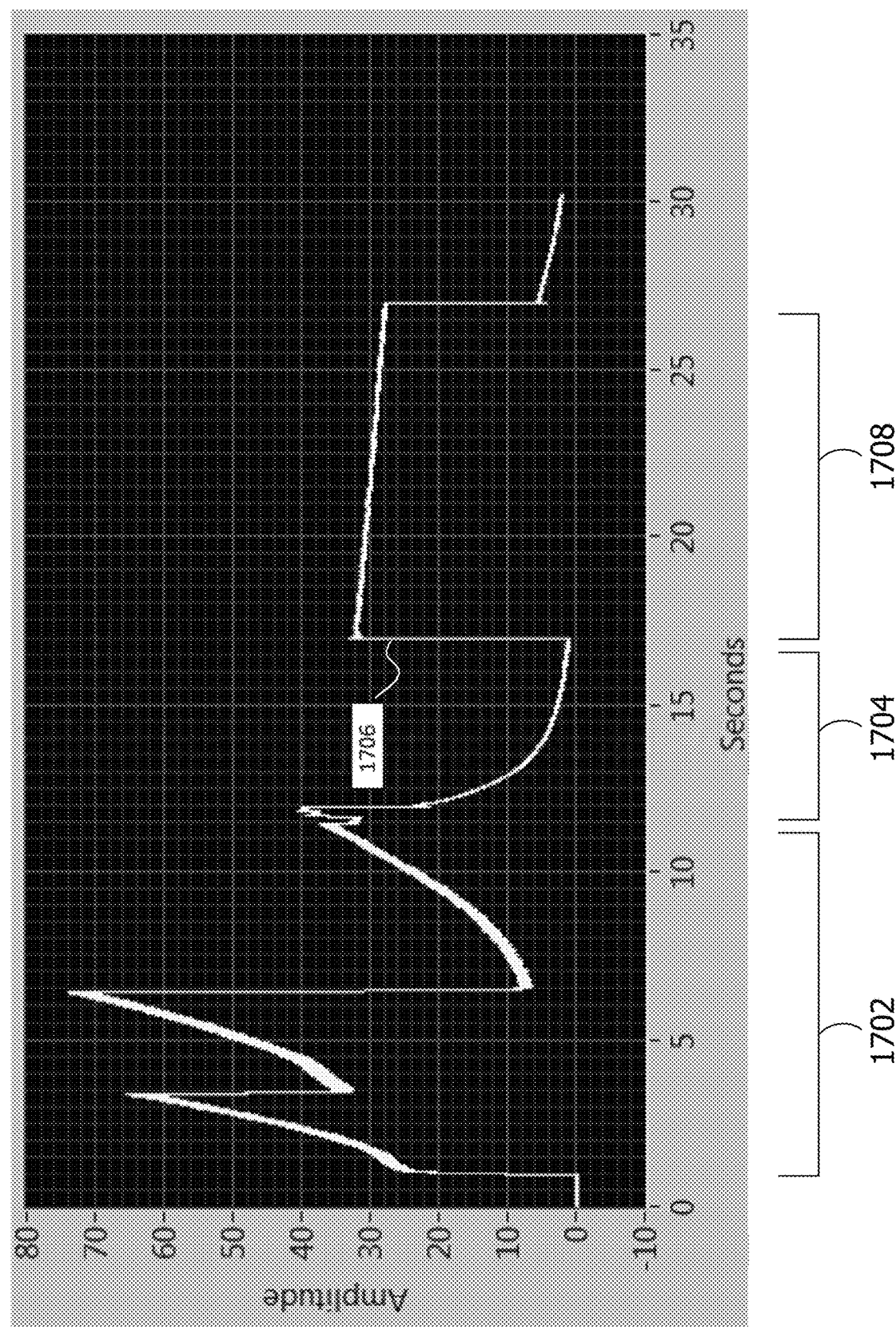
FIGS. 17A and 17B are graphical representations of another pressure profile produced by the compression system of FIG. 1 when the compression garment is in a wrapped configuration on a limb of a wearer.

FIG. 17A shows a pressure signal received from the pressure signal 27 and representative bladder pressure profile for one of bladders 13a, 13b, 13c. The pressure profile includes a therapy cycle period 1702, a bladder vent period 1704, a bladder test inflation period 1706, and a bladder pressure hold period 1708. At the end of the therapy cycle 1702, the tested bladder (e.g., one of bladders 13a, 13b, 13c) vents during the bladder vent period 1704. After the bladder vent period 1704, a short inflation is applied to the tested bladder during the bladder inflation period 1706 until the tested bladder achieves a pressure of about 30 mmHg. The one or more processors 7 execute computer executable instructions such that pulse detection, as further described below, is performed by the one or more processors 7 during the bladder pressure hold period 1708, which is about ten seconds in this exemplary embodiment. The bladder pressure hold period 1708 can be for a longer or shorter duration, provided that the duration is long enough to ensure that multiple pulses occur within the duration.

Figure 17B:
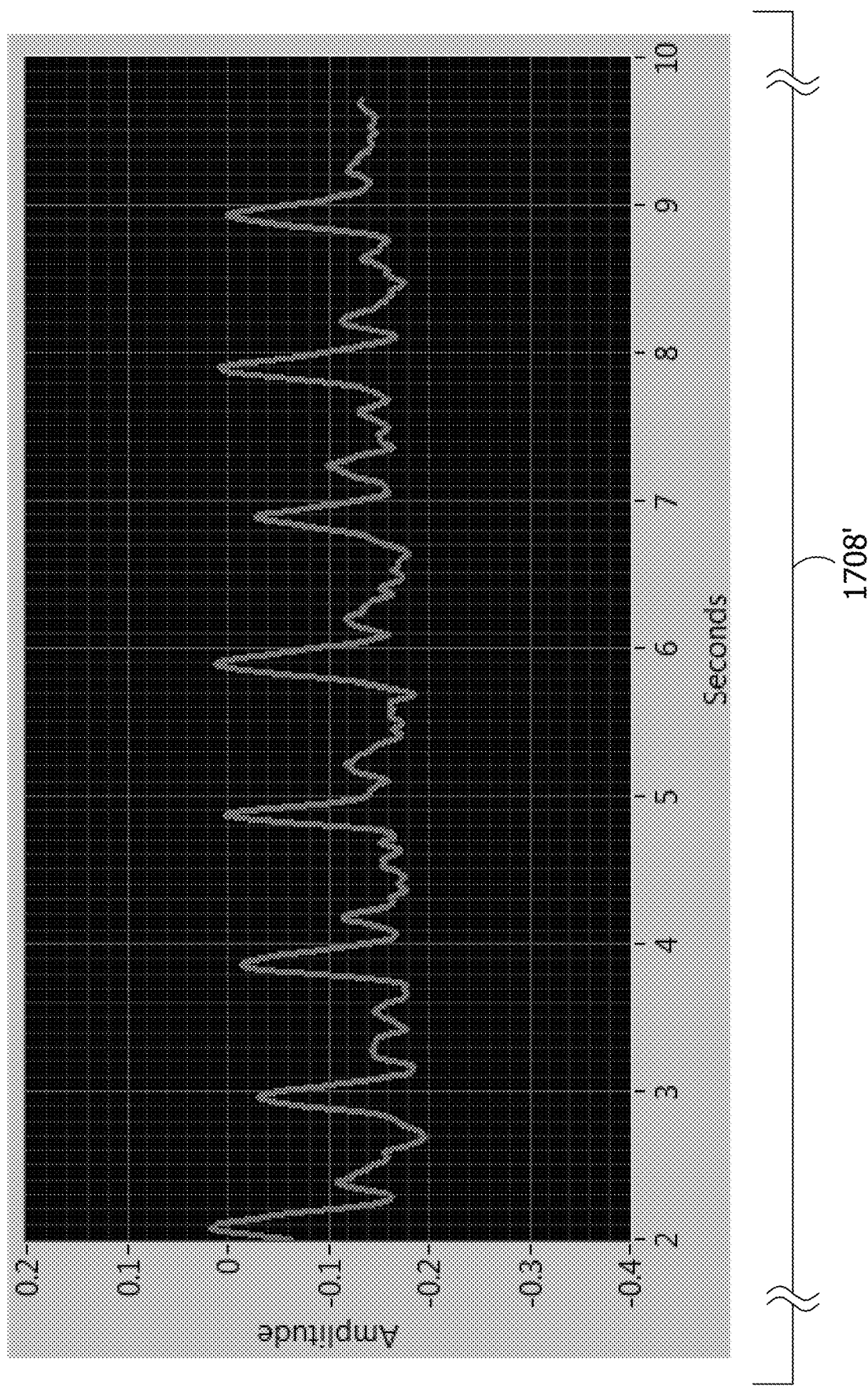

FIG. 17B illustrates a waveform 1708' indicative of the result of a filtering technique applied to a signal of interest during the pressure hold period 1708. In some embodiments, the computer-executable instructions include instructions to cause the one or more processors 7 to detect dominant peaks and check that the waveform falls within an expected range (e.g., 60-100 beats per minute (bpm) for a human wearer). In some embodiments, the expected range is 60-100 beats per minute (bpm) for a human wearer. It should be appreciated, however, that a wider range (e.g., 30-120 bpm) can be used to account for wearers who may be of ill-health and/or to account for measurements that may occur at locations on the body far away from the heart (e.g., the lower leg). In this exemplary embodiment, the one or more processors 7 detect pulsation associated with the heartbeat of the wearer and not the actual heart rate of the wearer.

Figure 18:
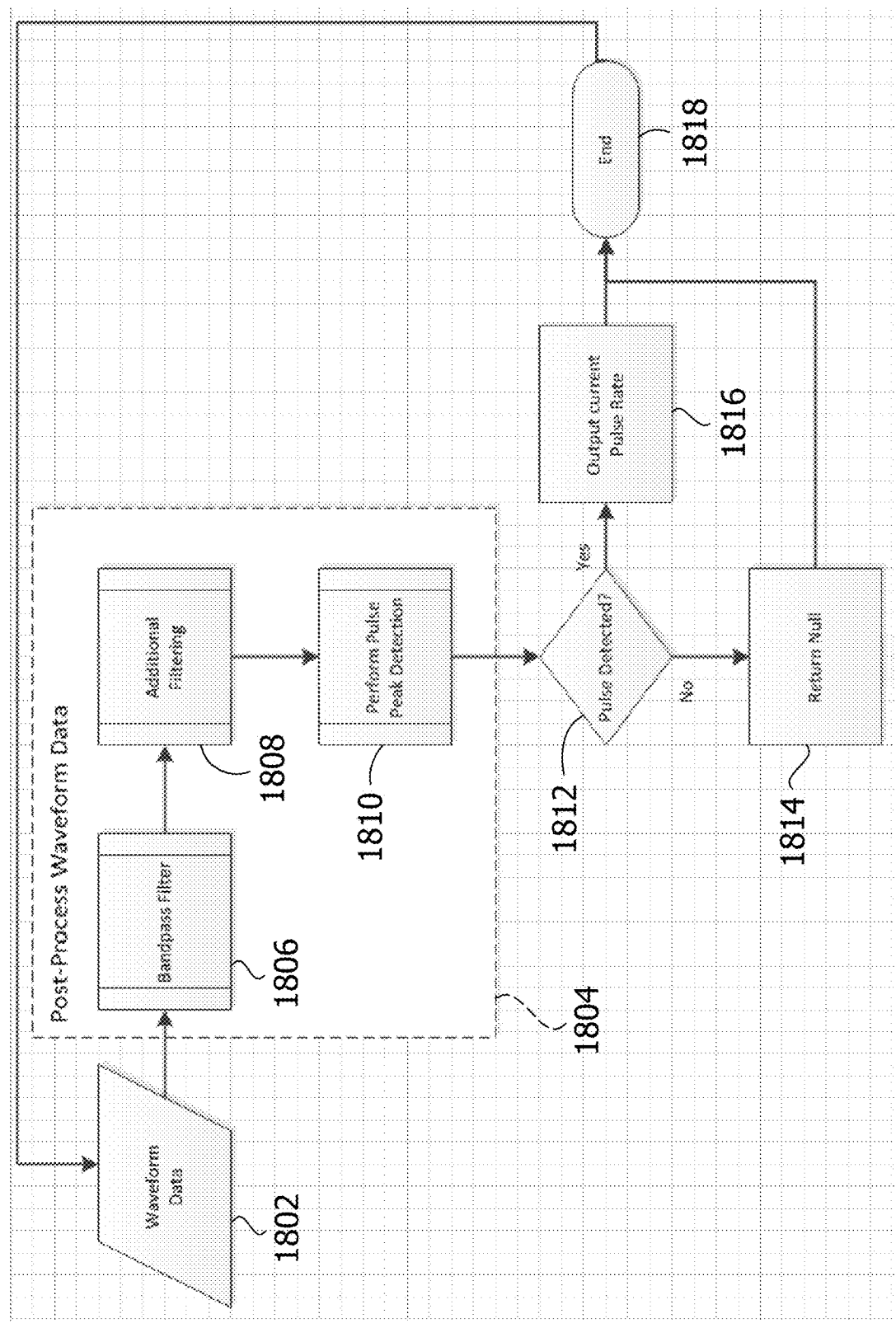
FIGS. 18-23C are flow diagrams of methods of compliance monitoring using the compression system of FIG. 1.

FIG. 18 is a schematic representation of an exemplary method 1800 of analyzing waveform data received from the pressure sensor 27 to determine whether the compression garment 10 is in the wrapped or unwrapped configuration around a limb of a wearer of the garment by detecting pulsations associated with the heartbeat of the wearer. This exemplary method can be carried out by the one or more processors 7 through execution of computer executable instructions embodied on the non-transitory, computer readable storage medium 33.

The one or more processors 7 execute computer executable instructions to sample 1802 initial pressure. In some embodiments, the initial pressure sampling is done at a rate of 100 Hz or higher and typical signal conditioning is used to remove baseline noise. Additionally or alternatively, the sampling 1802 may be expanded to include attenuation of frequencies just under a low cutoff (e.g., 0.25 Hz).

A post-process waveform analysis 1804 further includes a bandpass filter 1806, an additional filtering 1808, and a peak detection 1810. During the bandpass filter 1806, the signal of interest is filtered using a bandpass filtering technique in a typical range of frequencies associated with a typical heartrate range of a human wearer (e.g., 0.5-4 Hz for a human wearer).

During the additional filtering 1808, the peaks of the bandpass filtered signal are further refined. The additional filtering can include a lowpass filter with a cutoff of 5 Hz to produce a filtered value. Additionally or alternatively, the additional filtering can include a smoothing algorithm using the five most recent samples of the moving range to produce a filtered value. It should be appreciated that more than one filtering technique may be applied to the bandpass filtered signal during the additional filtering step 1808.

During a peak detection 1810, a peak detection is performed to check that the peaks of the filtered signal correspond to a heartbeat range of a typical human wearer. The peak detection 1810 can be based on a predetermined threshold (e.g., look only at peaks with a magnitude greater than 0.05 mmHg). Additionally or alternatively, the peak detection 1810 can be based on examining for repeating signals with frequencies within a heartbeat range of a typical human wearer, independent of magnitude (e.g., expanded to 30-240 bpm for margin). For example, a frequency analysis computation may be performed to check that a repeating signal with frequency within the heartbeat range of a typical human wearer is detected. Additionally or alternatively, the peak detection 1810 can be based on the highest magnitude peaks and checking that the frequency of those peaks falls within the expected heartbeat range of a typical human wearer. It should be appreciated that more than one peak detection technique may be used during the peak detection 1810. In some embodiments, peak detection 1810 includes a combination of peak detection based on a predetermined threshold and based on the highest magnitude peaks and checking that the frequency of those peaks falls within the expected heartbeat range of a typical human wearer because the signal-to-noise ratio is high enough that the pulses are plainly evident.

The computer executable instructions cause the one or more processors 7 to determine 1812 whether a features of a pulse of the wearer were detected during the peak detection 1810. If features of a pulse are determined 1812 to be present, the results of a positive determination can be indicated 1816. For example, the indication 1816 can include sending a visual representation to a display device associated with the compression system 1. Additionally or alternatively, the indication 1816 can include incrementing and/or pausing a timer. Upon the indication 1816, the process ends at step 1818 and returns back to step 1802. If an impulse is not detected at step 1812, the computer executable instructions cause the one or more processors 7 to return a null value at step 1814. After step 1814, the process ends at step 1818 and returns to sampling 1802.

Figure 19:
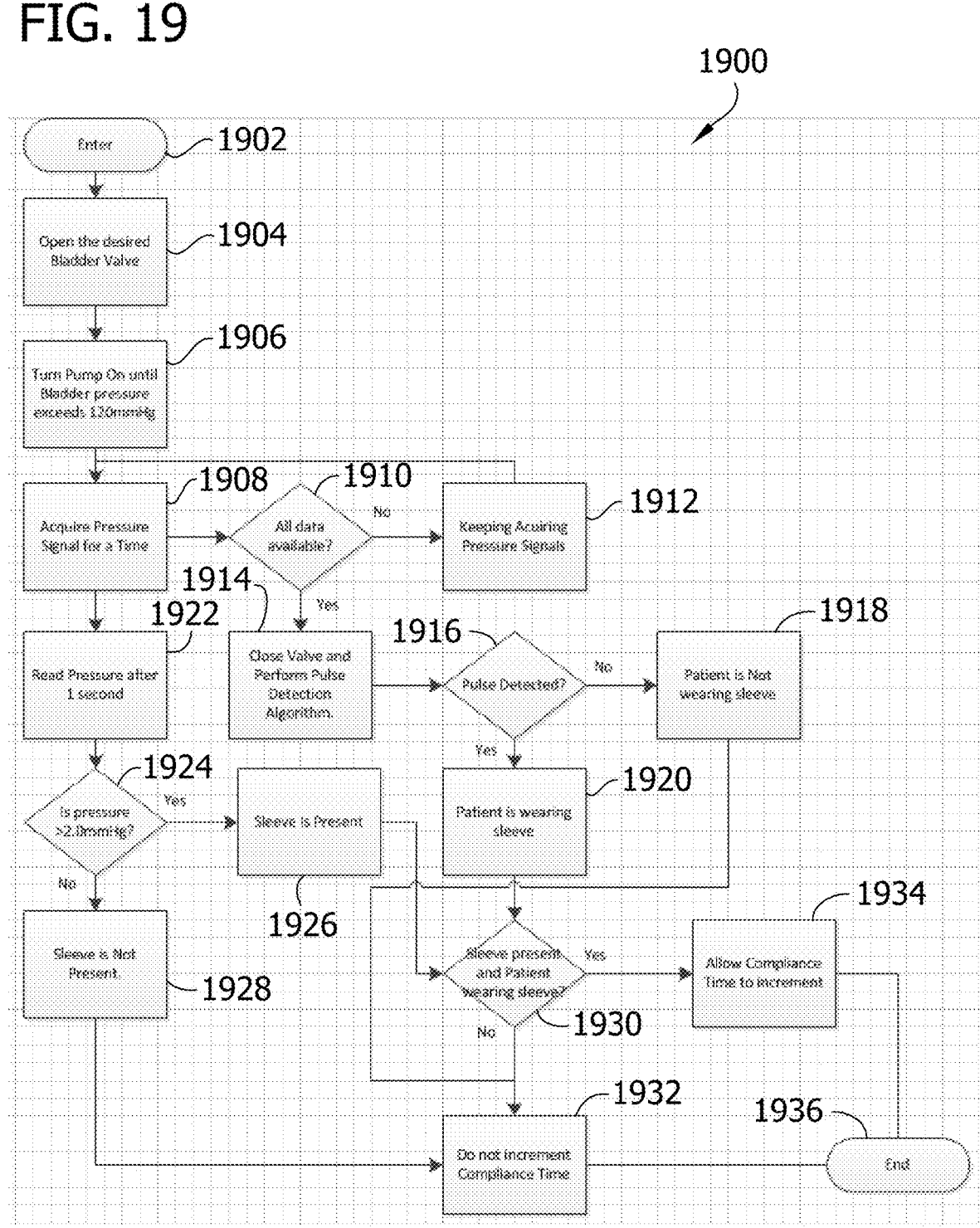

Referring to FIG. 19, is a schematic representation of an exemplary method 1900 of analyzing waveform data received from a pressure sensor (e.g., the pressure sensor 27) to determine whether a compression garment (e.g., compression garment 10) is in the wrapped or unwrapped configuration during a garment verification process. For ease of explanation and for the sake of clarity, the method 1900 is described for a single bladder (e.g., one of the bladders 13a, 13b, or 13c). It should be appreciated, however, that the method 1900 can be repeated to check for additional bladders corresponding to different valves.

The method 1900 begins at step 1902 and the desired bladder valve (e.g., bladder valve 25a, 25b, 25c) is opened 1904. A pressurized fluid source (e.g., pressurized fluid source 21) is turned on 1906 until pressure in the corresponding bladder exceeds about 120 mmHg.

A pressure signal is received 1908 from the pressure sensor 27 for a period of time. A determination 1910 is made regarding whether all data are available. If all data are not available, pressure signals continue to be acquired 1912 and the pressure signal is received 1908. If the determination 1910 is made that all data are available at step 1910, close the corresponding valve is closed 1914 and a pulse detection algorithm is performed.

In some embodiments, the pulse detection algorithm includes one or more steps of the post-process waveform analysis 1804 described above.

A determination 1916 is made regarding whether a pulse is detected after the valve is closed 1914 and fluid is isolated in the bladder. The lack of detection of a pulse is indicative of the compression garment 10 being in an unwrapped configuration away from a limb of the wearer at step 1918 and the method proceeds to step 1932, where a compliance time is not incremented, before ending the method at step 1936. The detection of a pulse at step 1916 is indicative of the compression garment 10 being in a wrapped configuration around a limb of the wearer at step 1920 and the method continues to step 1930.

At step 1922, the computer executable instructions cause the one or more processors 7 to read the pressure after one second has elapsed after the pump is turned on in step 1906. At step 1924, the computer executable instructions cause the one or more processors 7 to determine whether the pressure is greater than 2.0 mmHg. The pressure exceeding 2.0 mmHg at step 1924 is indicative of the compression garment 10 being present (e.g., in fluid communication with valve 25a, 25b, 25c) at step 1926 and the method proceeds to step 1930. The pressure not exceeding 2.0 mmHg at step 1924 is indicative of the compression garment 10 not being present (e.g., not in fluid communication with valve 25a, 25b, 25c) at step 1928 and the method proceeds to step 1932, where a compliance time is not incremented, before ending the method at step 1936.

At step 1930, the computer executable instructions cause the one or more processors 7 to determine whether the compression garment 10 is present and in a wrapped configuration around a limb of the wearer. If either the compression garment 10 is determined to not be present or not be in a wrapped configuration around a limb of the wearer, then the method proceeds to step 1932 where a compliance time is not incremented before ending the method at step 1936. If the compression garment 10 is determined by the one or more processors 7 to be present and be in a wrapped configuration, then the method proceeds to step 1934 where a compliance time is incremented before ending the method at step 1936.

Figure 20:
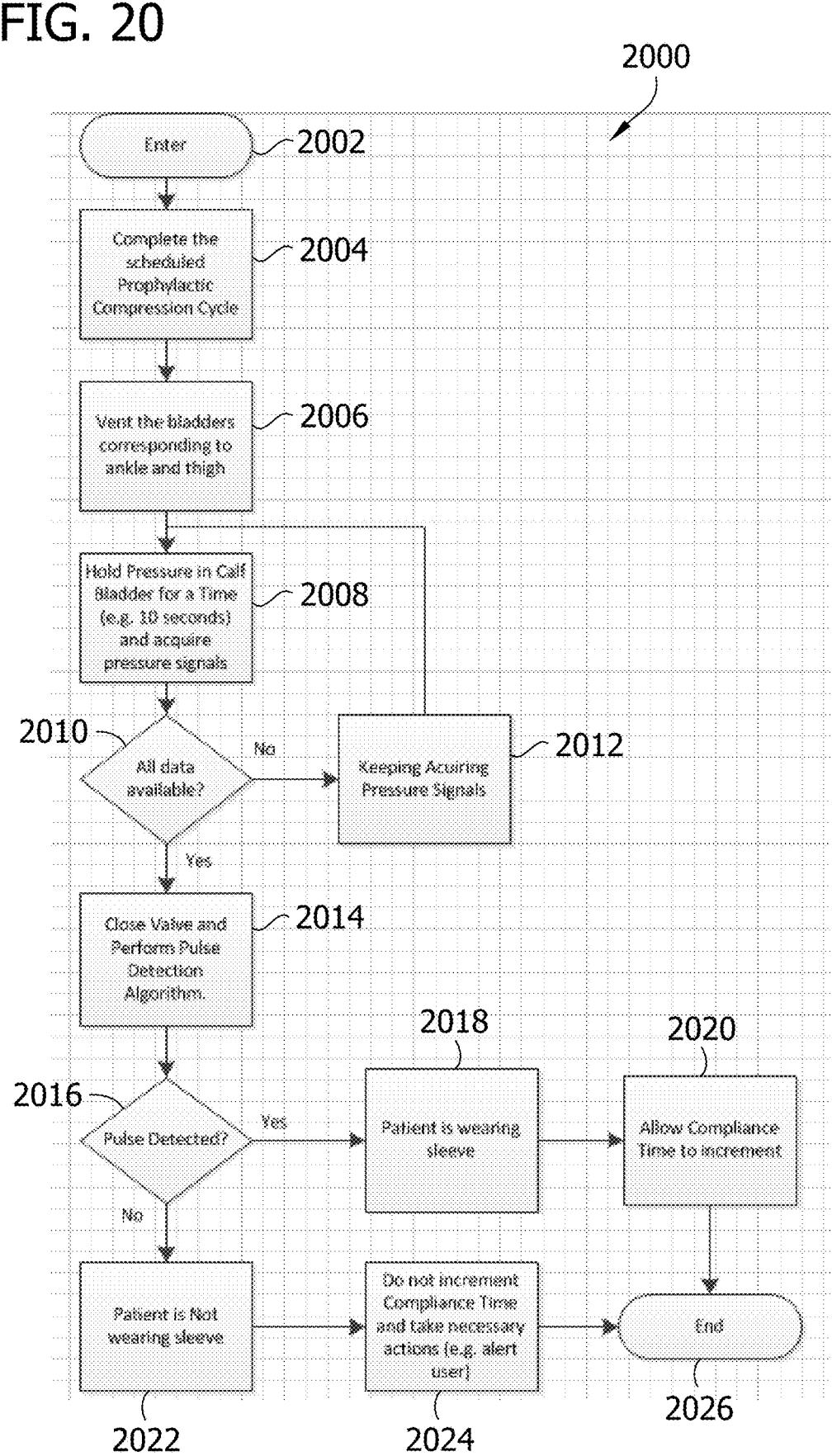

Referring to FIG. 20, the computer executable instructions embodied on the computer readable storage medium 33 cause the one or more processors 7 to execute a method 2000 of analyzing waveform data received from the pressure sensor 27 to determine whether the compression garment is in the wrapped or unwrapped configuration following the end of a cycle pressure. The method 2000 begins at step 2002 and proceeds to step 2004, where the computer executable instructions cause the one or more processors 7 to complete a prophylactic compression cycle. At step 2006, the computer executable instructions cause the one or more processors 7 to vent the bladders corresponding to the ankle and thigh of the wearer (e.g., bladders 13a and 13c). At step 2008, the computer executable instructions cause the one or more processors 7 to hold the pressure in the bladder corresponding to the calf of the wearer (e.g., bladder 13b) for a predetermined period of time (e.g., 10 seconds) and acquire pressure signals via the pressure sensor 27.

At step 2010, the computer executable instructions cause the one or more processors 7 to determine whether all of the data is available. If all of the data is not available at step 2010, then the method proceeds to step 2012 to continue acquiring pressure signals from the pressure sensor 27 before continuing back to step 2008. If all of the data is available at step 2010, then the method proceeds to step 2014 where the computer executable instructions cause the one or more processors 7 to perform the pulse detection algorithm. In some embodiments, the pulse detection algorithm includes one or more steps of the post-process waveform analysis 1804 described above. At step 2016, the computer executable instructions cause the one or more processors 7 to determine whether a pulse is detected at step 2014. The lack of detection of a pulse is indicative of the compression garment 10 being in an unwrapped configuration away from a limb of the wearer at step 2022. The method then proceeds to step 2024, where the computer executable instructions cause the one or more processors 7 to not increment a compliance time and cause the one or more processors 7 to take one or more actions (e.g., alert the user) before ending the method at step 2026. The detection of a pulse at step 2016 is indicative of the compression garment 10 being in a wrapped configuration around a limb of the wearer at step 2018. The method then proceeds to step 2020, where the computer executable instructions cause the one or more processors 7 to increment a compliance time before ending the method at step 2026.

Figure 21:
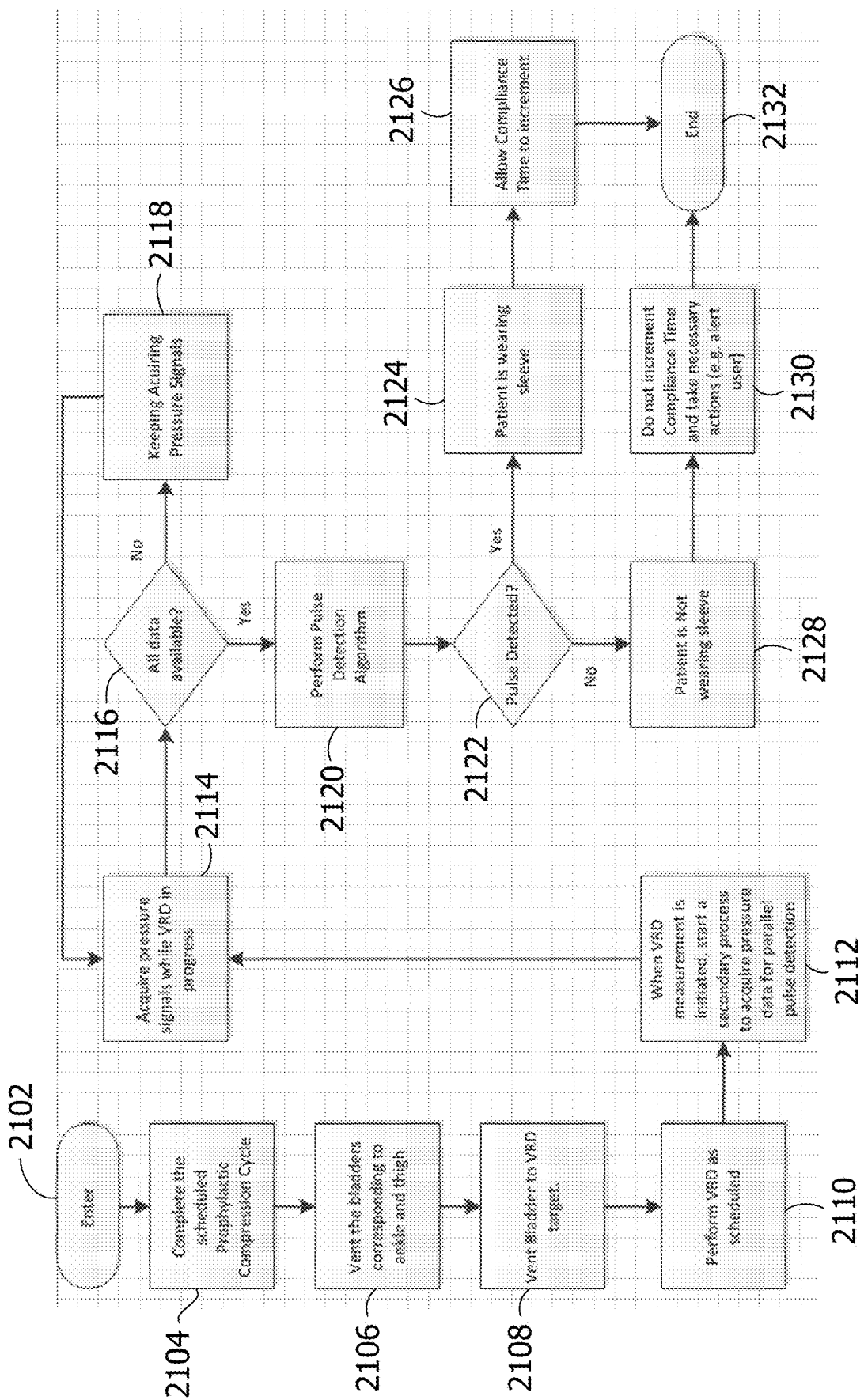

Referring to FIG. 21, the computer executable instructions embodied on the computer readable storage medium 33 cause the one or more processors 7 to execute a method 2100 of analyzing waveform data received from the pressure sensor 27 to determine whether the compression garment is in the wrapped or unwrapped configuration during a Venous Refill Determination (VRD). The method 2100 begins at step 2102 and proceeds to step 2104, where the computer executable instructions cause the one or more processors 7 to complete a prophylactic compression cycle. At step 2106, the computer executable instructions cause the one or more processors 7 to vent the bladders corresponding to the ankle and thigh and of the wearer (e.g., bladders 13a and 13c). At step 2108, the computer executable instructions cause the one or more processors 7 to vent the pressure in the bladder corresponding to the calf of the wearer (e.g., bladder 13b) to a VRD target. At step 2110, the computer executable instructions cause the one or more processors 7 to perform VRD as scheduled. Once the VRD measurement is initiated, the computer executable instructions cause the one or more processors 7 to start a secondary process to acquire pressure data from the pressure sensor 27 for parallel pulse detection. At step 2114, the computer executable instructions cause the one or more processors 7 to acquire pressure signals from the pressure sensor 27 while VRD is in progress.

At step 2116, the computer executable instructions cause the one or more processors 7 to determine whether all of the data is available. If all of the data is not available at step 2116, then the method proceeds to step 2118 to continue acquiring pressure signals from the pressure sensor 27 before continuing back to step 2114. If all of the data is available at step 2116, then the method proceeds to step 2120 where the computer executable instructions cause the one or more processors 7 to perform the pulse detection algorithm. In some embodiments, the pulse detection algorithm includes one or more steps of the post-process waveform analysis 1804 described above. At step 2122, the computer executable instructions cause the one or more processors 7 to determine whether a pulse is detected at step 2120. The lack of detection of a pulse is indicative of the compression garment 10 being in an unwrapped configuration away from a limb of the wearer at step 2128. The method then proceeds to step 2130, where the computer executable instructions cause the one or more processors 7 to not increment a compliance time and cause the one or more processors 7 to take one or more actions (e.g., alert the user) before ending the method at step 2132. The detection of a pulse at step 2122 is indicative of the compression garment 10 being in a wrapped configuration around a limb of the wearer at step 2124. The method then proceeds to step 2126, where the computer executable instructions cause the one or more processors 7 to increment a compliance time before ending the method at step 2132.

Figure 22:
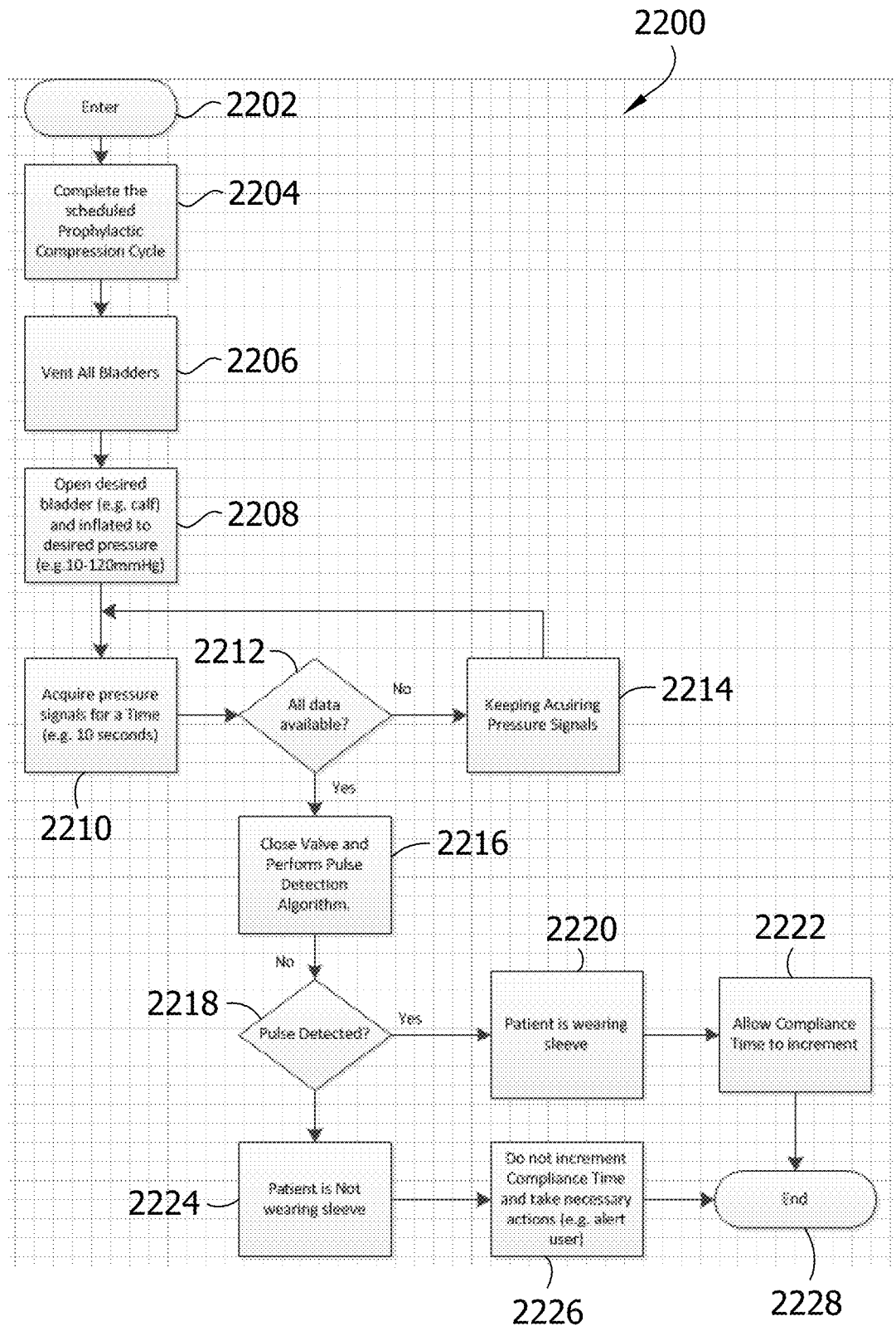

Referring to FIG. 22, the computer executable instructions embodied on the computer readable storage medium 33 cause the one or more processors 7 to execute a method 2200 of analyzing waveform data received from the pressure sensor 27 to determine whether the compression garment is in the wrapped or unwrapped configuration as an independent cycle. The method 2200 begins at step 2202 and proceeds to step 2204, where the computer executable instructions cause the one or more processors 7 to complete a prophylactic compression cycle. At step 2206, the computer executable instructions cause the one or more processors 7 to vent all bladders 13a, 13b, 13c. At step 2208, the computer executable instructions cause the one or more processors 7 to open a desired valve (e.g., valve 25b) and inflate a desired bladder (e.g., bladder 13b) to a desired pressure (e.g., 10-120 mmHg). At step 2210, the computer executable instructions cause the one or more processors 7 to acquire pressure signals via the pressure sensor 27 for a predetermined period of time (e.g., 10 seconds).

At step 2212, the computer executable instructions cause the one or more processors 7 to determine whether all of the data is available. If all of the data is not available at step 2212, then the method proceeds to step 2214 to continue acquiring pressure signals from the pressure sensor 27 before continuing back to step 2210. If all of the data is available at step 2212, then the method proceeds to step 2216 where the computer executable instructions cause the one or more processors 7 to close the corresponding valve (e.g., 25b) and perform the pulse detection algorithm. In some embodiments, the pulse detection algorithm includes one or more steps of the post-process waveform analysis 804 described above. At step 2218, the computer executable instructions cause the one or more processors 7 to determine whether a pulse is detected at step 2216. The lack of detection of a pulse is indicative of the compression garment 10 being in an unwrapped configuration away from a limb of the wearer at step 2224. The method then proceeds to step 2226, where the computer executable instructions cause the one or more processors 7 to not increment a compliance time and cause the one or more processors 7 to take one or more actions (e.g., alert the user) before ending the method at step 2228. The detection of a pulse at step 2218 is indicative of the compression garment 10 being in a wrapped configuration around a limb of the wearer at step 2220. The method then proceeds to step 2222, where the computer executable instructions cause the one or more processors 7 to increment a compliance time before ending the method at step 2228.

Figure 23A:
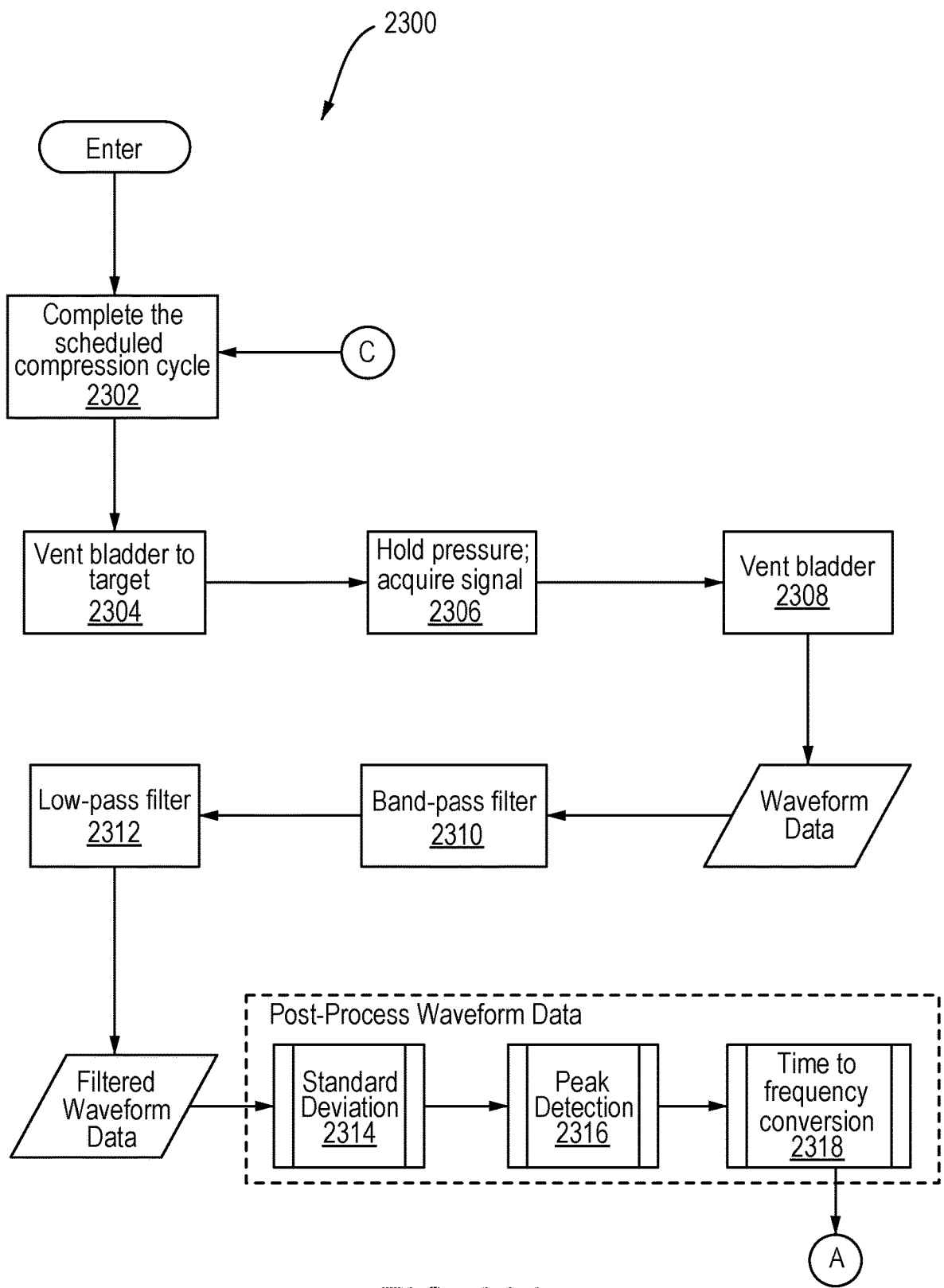
Figure 23B:
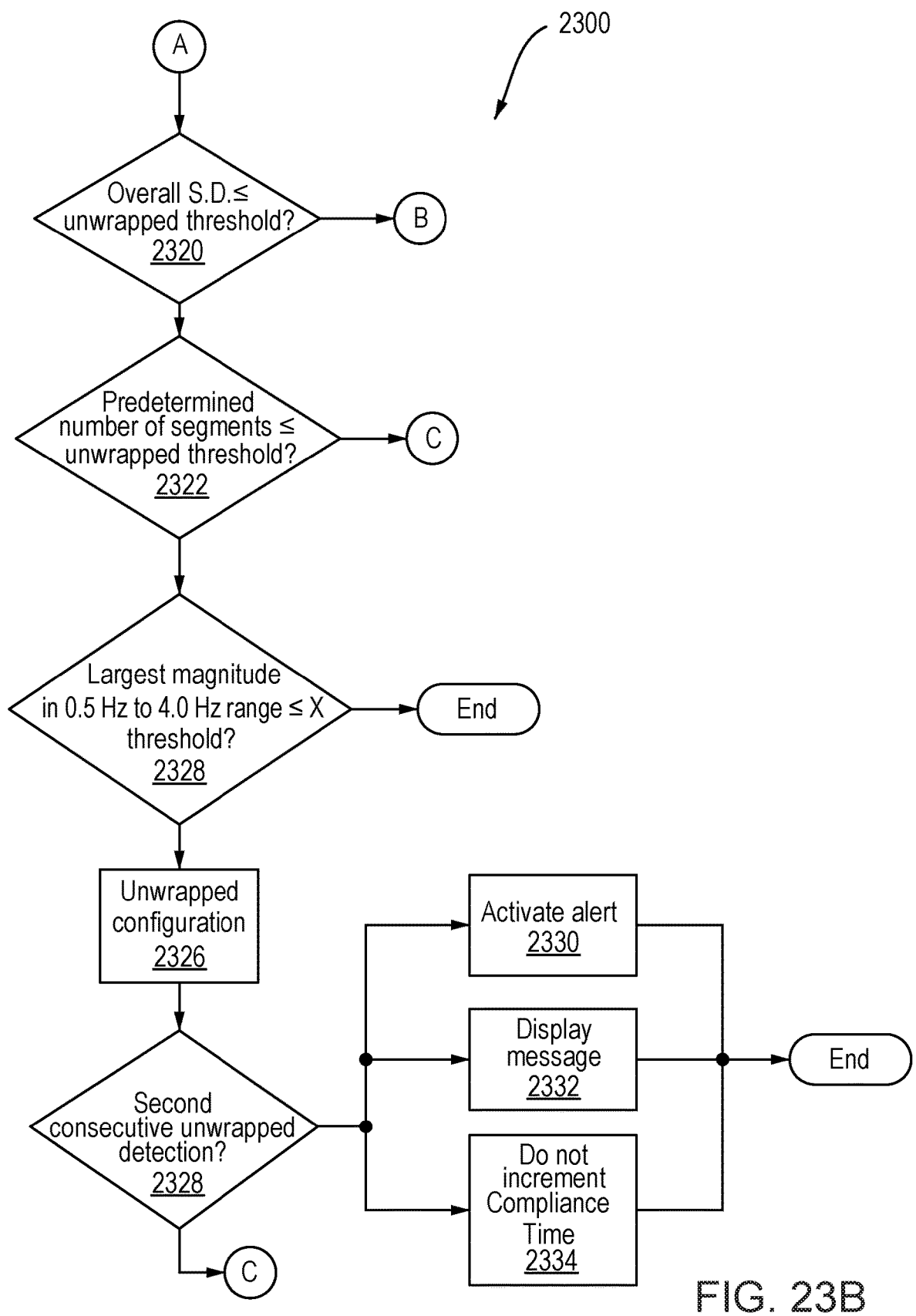
Figure 23C:
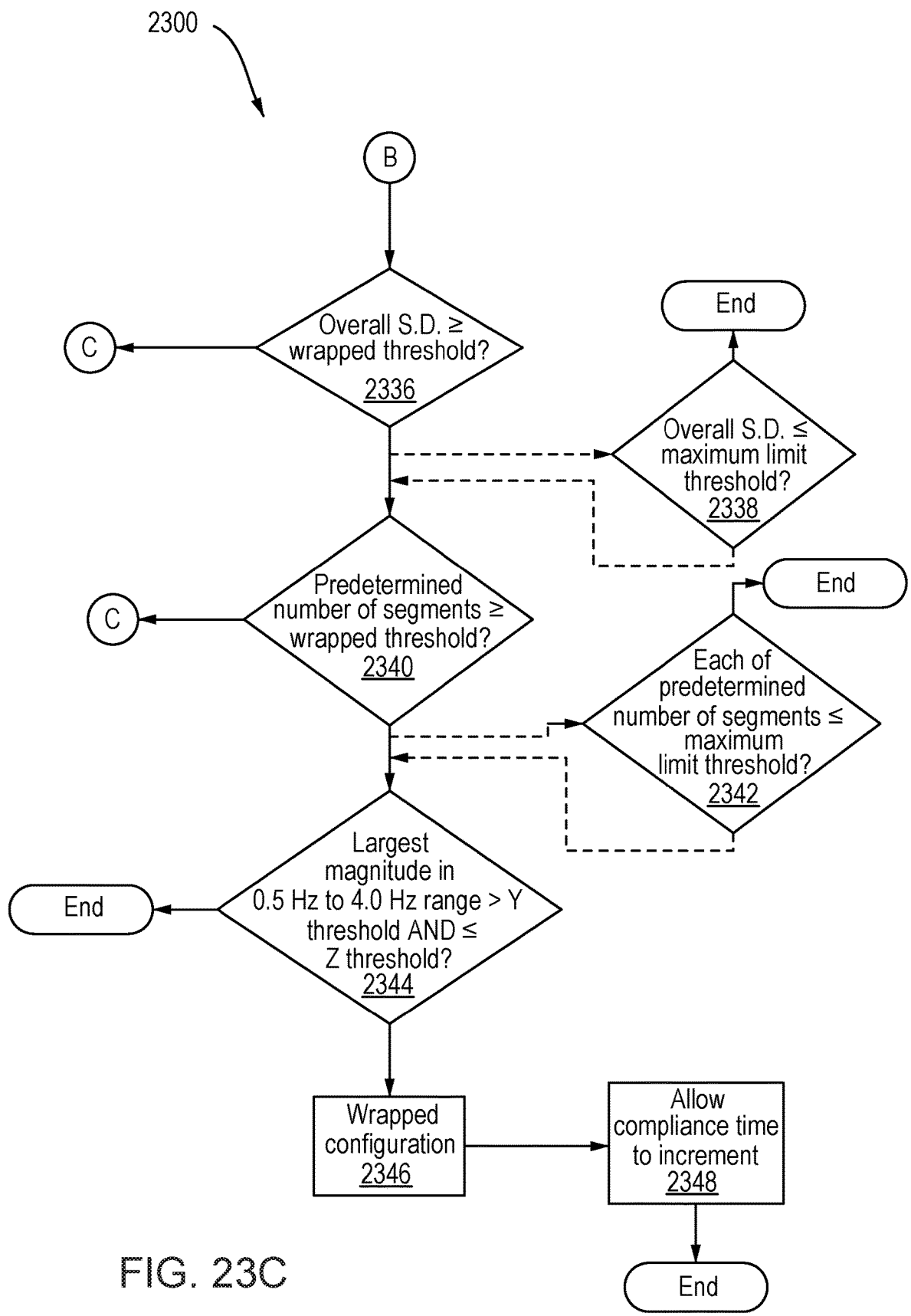

FIGS. 23A-C are a schematic representation of an exemplary method 2300 of analyzing waveform data received from the pressure sensor 27 to determine whether the compression garment 10 is in the wrapped or unwrapped configuration around a limb of a wearer of the garment by detecting pulsations associated with the heartbeat of the wearer. This exemplary method can be carried out by the one or more processors 7 through execution of computer executable instructions embodied on the non-transitory, computer readable storage medium 33.

The method 2300 begins and proceeds to step 2302, where the computer executable instructions cause the one or more processors 7 to complete a prophylactic compression cycle. At step 2304, the computer executable instructions cause the one or more processors 7 to vent the bladders corresponding to, for instance, the ankle and thigh of the wearer (e.g., bladders 13a and 13c) and to vent the bladder corresponding to, for instance, the calf of the wearer (e.g., bladder 13b) until a target pressure is achieved. In an embodiment, the target pressure comprises an initial lower target pressure of about 5 to about 7 mmHg. Alternatively, the target pressure comprises about 26 to about 32 mmHg when the initial lower target pressure does not produce the expected result. The initial lower target pressure provides an exemplary benefit of exerting less pressure against the limb of the wearer, which is more comfortable for the patient relative to higher pressures, before re-trying at the higher target pressure, which is less comfortable for the patient.

Upon reaching the target pressure, the computer executable instructions cause the one or more processors 7 to retain the pressure in the bladder corresponding to the calf of the wearer (e.g., bladder 13b) while the signal is acquired at a rate of about 100 Hz for a period of at least about 15 seconds. In an embodiment, the period comprises pressure hold period 1504, as further described herein. A hold period of longer than about 15 seconds may also be utilized without departing from the scope of the invention. At step 2308, the computer executable instructions cause the one or more processors 7 to vent the pressure in the bladder corresponding to the calf of the wearer (e.g., bladder 13b).

Following the venting of the measurement bladder (e.g., bladder 13b), the computer executable instructions cause the one or more processors 7 to perform further signal conditioning which prepares the data for the patient detection algorithm. As shown in FIG. 23A, the computer executable instructions cause the one or more processors 7 to band-pass filter 2310 the waveform data. In an embodiment, the most recent 1024 acquired samples, which correspond to a time window of about 10 seconds, are passed through band-pass filter 2310 having a pass-band of about 0.5-25 Hz to isolate the signals reflective of a cardiac cycle of the wearer. In an embodiment, the first three samples of the 1024 acquired samples are disregarded as a settle time period. It will be understood by one of ordinary skill in the art that other amounts of most recent acquired samples may be utilized without departing from the scope of the invention. For example, any number of most recent acquired samples being a power of two aids in frequency calculation.

Figure 24:
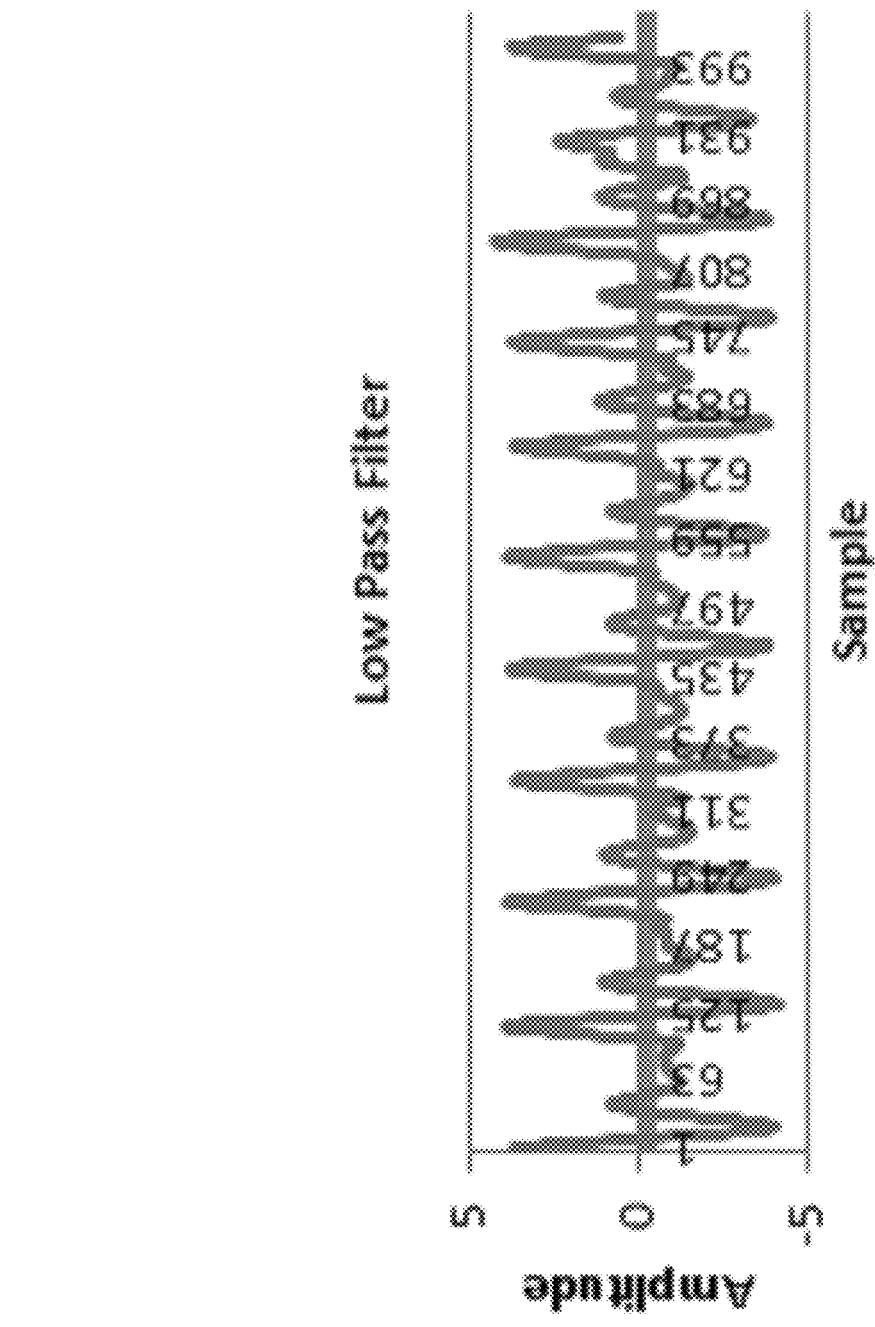
FIGS. 24 and 25 are graphical representations of another pressure profile produced by the compression system of FIG. 1 when the compression garment is in a wrapped configuration on a limb of a wearer.

The computer executable instructions cause the one or more processors 7 to pass the output of the band-pass filter 2310 through a low-pass filter 2312 having a low pass cutoff frequency of about 5 Hz. In an embodiment, low-pass filter 2312 further removes noise in the waveform data and reveals pulsations associated with the circulatory system of the lower limb of the wearer. Referring to FIG. 24, an exemplary signal from the output of low-pass filter 2312 is shown. In this embodiment, the signal includes about 1024 samples having crisp pulsations associated with the circulatory system of the lower limb of the wearer.

With the filtered waveform data available, the computer executable instructions cause the one or more processor 7 to perform several subsequent calculations on the filtered waveform data to determine whether the compression garment 10 is in the wrapped or unwrapped configuration around a limb of a wearer of the garment. In an embodiment, the subsequent calculations are referred to as post-processing of the filtered waveform.

Referring again to FIG. 23A, the computer executable instructions cause the one or more processors 7 to perform post-processing of the filtered waveform at 2314, 2316, and 2318. As shown, one or more processors 7 calculate the standard deviation of the filtered waveform data and/or portions thereof. It is empirically known that a compression garment in an unwrapped configuration (i.e., idle) has a stable, flat pressure signal including only normal white noise. In contrast, a pressure signal representative of a pressure in a compression garment in a wrapped configuration around a limb of a wearer of the garment includes pulsations and/or other measureable signal characteristics. Therefore, it is possible to distinguish a compression garment in a wrapped configuration around a limb of a wearer from a compression garment in an unwrapped configuration based, in whole or in part, on this calculation.

In an embodiment, the computer executable instructions cause the one or more processors 7 to divide the low-pass filtered signal (e.g., 1024 samples) into five sample groups and calculate the standard deviation 2314 ($\sigma$) for each group. It will be understood by one of ordinary skill in the art that the low-pass filtered signal may be divided into a different number of samples groups, such as when a different number of samples are used for example. An exemplary purpose of dividing the low-pass filtered signal into sample groups is to isolate portions of time. For example, it is known that large anomalous pressure spikes (e.g., due to wearer sneezing, coughing, and the like) in a representative pressure signal occur during normal treatment due to movement of the limb of the wearer and/or other factors. Time-slicing of the signal (e.g., dividing the signal into sample groups) allows the one or more processors 7 to determine if the entire waveform is "steady" or if there is an anomaly within a particular range of the sample. In an embodiment, the computer executable instructions cause the one or more processors 7 to calculate the total standard deviation 2314 ($\sigma$) for the entire low-pass filtered signal (e.g., 1024 samples).

Figure 25:
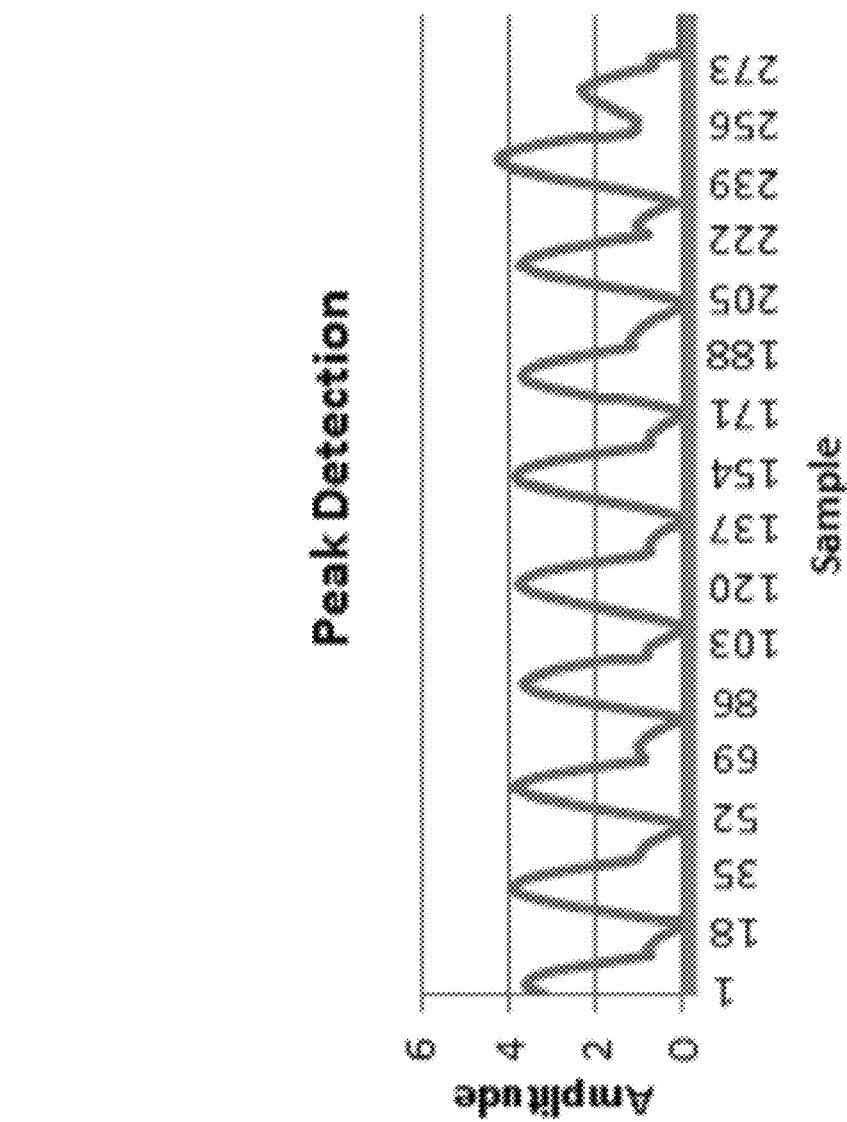

After calculating the standard deviation, the computer executable instructions cause the one or more processors 7 to perform peak detection 2316. In an embodiment, the one or more processors 7 process the filtered waveform (e.g., 1024 samples) using a windowing technique comprising 32 samples per window. The one or more processors 7 index the peak from each 32-sample window one after the other to produce a down-sampled waveform comprising only the signal peaks (e.g., the signal of interest). For example, the one or more processors 7 may initially index each peak from 1 to 32 and then increment the index by one (e.g. from 2 to 33) as additional waveform signal data is generated. The one or more processors 7 ignore negative peaks. In an embodiment, the 32-sample window leaves a local maximum for each window. Additionally and/or alternatively, the 32-sample window reduces the number of samples by one-quarter, removes negative peaks, and provides awareness that the down-sampled signal is representative of about 10 seconds of real time. Referring to FIG. 25, an exemplary signal from the output of peak detection 2316 is shown, including only the true peaks which ultimately reveal the pulsation of interest. In this embodiment, the signal includes about 250 to 300 samples which still correspond to about 10 seconds of real time. In an embodiment, the number of samples will vary depending on the number of peaks identified by the one or more processors 7. In the embodiment illustrated in FIG. 25, the sampling frequency is calculated as the result of the number of samples divided by the amount of time (e.g., Sampling f=N samples/10.24 seconds).

Referring further to FIG. 23A, with the down-sampled peak detection waveform available, the one or more processors 7 utilize the fundamental frequency to assist in confirming if the compression garment 10 is in the wrapped configuration around a limb of a wearer of the garment by performing a time to frequency conversion 2318. In an embodiment, the computer executable instructions cause the one or more processors 7 to compute a Fourier Transform (e.g., Fast Fourier Transform) of the signal and output the highest magnitude between 0.5 Hz (e.g., about 30 bpm) and 4 Hz (e.g., about 200 bpm). One having ordinary skill in the art will understand that transforms other than a Fast Fourier Transform may be used to discover a cardiac cycle of the wearer without departing from the scope of the invention.

After completing the post-processing, the computer executable instructions cause the one or more processors 7 to determine whether the compression garment 10 is in an unwrapped configuration or a wrapped configuration around a limb of a wearer of the garment. Referring to FIG. 23B, the computer executable instructions cause the one or more processors 7 to determine, at step 2320, whether the total standard deviation 2314 (σ) for the entire low-pass filtered signal (e.g., 1024 samples) is less than or equal to an unwrapped threshold (e.g., 0.25). When the one or more processors 7 determine the total standard deviation is not less than or equal to the unwrapped threshold, the method 2300 continues to step 2336 as further described herein. When the one or more processors 7 determine the total standard deviation is less than or equal to the unwrapped threshold, the method 2300 continues to step 2322.

At step 2322, the computer executable instructions cause the one or more processors 7 to determine whether a predetermined number of segments (e.g. sample groups) into which the low-pass filtered signal has been divided are each less than or equal to the unwrapped threshold (e.g., 0.25). In an alternative embodiment, the one or more processors 7 divide the low-pass filtered signal into five sample groups and determine at 2322 whether the standard deviation of each of the five sample groups is less than or equal to the unwrapped threshold. Alternatively, the one or more processors 7 divide the low-pass filtered signal into five sample groups and determine at 2322 whether the standard deviation of at least three of the five sample groups is less than or equal to the unwrapped threshold. When the one or more processors 7 determine each of the predetermined number of segments is not less than or equal to the unwrapped threshold, the method 2300 continues back to step 2302 to re-try the cycle. When the one or more processors 7 determine each of the predetermined number of segments is less than or equal to the unwrapped threshold, the process continues to step 2324.

At step 2324, the computer executable instructions cause the one or more processors 7 to determine whether the largest (e.g., highest amplitude) magnitude in the 0.5-4.0 Hz range of the time to frequency transformed (e.g., Fast Fourier Transform) signal is less than or equal to a threshold X (e.g., 0.2). When the one or more processors 7 determine the largest magnitude in the 0.5-4.0 Hz range is not less than or equal to the threshold X, the method 2300 ends. When the processors 7 determine at 2324 the largest magnitude in the 0.5-4.0 Hz range is less than or equal to the threshold X, the one or more processors 7 determine at 2326 that the compression garment 10 is in an unwrapped configuration. In an embodiment, the computer executable instructions cause the one or more processors 7 to declare the compression garment 10 is in an unwrapped configuration (e.g., the wearer is not wearing the compression garment) when the Boolean result of step 2320 is logical true AND the result of step 2322 is logical true AND the result of step 2324 is logical true.

At step 2328, the computer executable instructions cause the one or more processors 7 to determine whether the unwrapped configuration detection at 2326 is the second consecutive such determination. When the one or more processors 7 determine the unwrapped configuration detection 2326 is not the second consecutive detection, the method 2300 continues back to step 2302 to perform a second measurement on the next cycle for the corresponding limb of the wearer. When the one or more processors 7 determine the unwrapped configuration 2326 is the second consecutive detection, the method 2300 continues to at least one of three steps. At step 2330, the computer executable instructions cause the one or more processors 7 to activate an audible alert, such as via a speaker and/or other electromechanical devices that produce sound connected to controller 5 of compression system 1. In an embodiment, the alert is a multi-toned audible alert. At step 2332, the computer executable instructions cause the one or more processors 7 to display an error message on a display device associated with the compression system 1. At step 2334, the computer executable instructions cause the one or more processors 7 to not increment a compliance time before ending the method 2300. In an embodiment, therapy using compression garment 10 is not stopped by halting 2334 the compliance time and the compliance time remains in its current state until receiving a response via a display device and/or an input device (e.g. from a human user).

Referring to FIG. 23C, the computer executable instructions cause the one or more processors 7 to determine, at step 2336, whether the total standard deviation 2314 (σ) for the entire low-pass filtered signal (e.g., 1024 samples) is greater than or equal to a wrapped threshold (e.g., 0.35). When the one or more processors 7 determine the total standard deviation is not greater than or equal to the wrapped threshold, the method 2300 continues back to step 2302. When the one or more processors 7 determine the total standard deviation is greater than or equal to the wrapped threshold, the method 2300 continues to step 2338 and/or step 2340.

In an embodiment, the method 2300 continues to step 2338 in which the computer executable instructions cause the one or more processors 7 to determine whether the total standard deviation 2314 (σ) for the entire low-pass filtered signal (e.g., 1024 samples) is less than or equal to a maximum limit threshold (e.g. 10.0). When the one or more processors 7 determine the total standard deviation for the entire low-pass filtered signal is not less than or equal to the maximum limit threshold, the method 2300 ends. When the one or more processors 7 determine the total standard deviation of the entire low-pass filtered signal is less than or equal to the maximum limit threshold, the method 2300 continues to step 2340.

At step 2340, the computer executable instructions cause the one or more processors 7 to determine whether a predetermined number of segments (e.g., sample groups) into which the low-pass filtered signal has been divided are each greater than or equal to the wrapped threshold (e.g., 0.35). In an embodiment, the one or more processors 7 divide the low-pass filtered signal into five sample groups and determine 2340 whether the standard deviation of each of the five sample groups is greater than or equal to the wrapped threshold. Alternatively, the one or more processors 7 divide the low-pass filtered signal into five sample groups and determine 2340 whether the standard deviation of at least three of the five sample groups is greater than or equal to the wrapped threshold. When the one or more processors 7 determine each of the predetermined number of segments is not greater than or equal to the wrapped threshold, the method 2300 continues back to step 2302 to re-try the cycle. When the one or more processors 7 determine each of the predetermined number of segments is greater than or equal to the wrapped threshold, the process continues to step 2342 and/or step 2344.

At step 2342, the computer executable instructions cause the one or more processors 7 to determine whether each of a predetermined number of segments (e.g., sample groups) into which the low-pass filtered signal has been divided are each less than or equal to the maximum limit threshold (e.g., 10.0). When the one or more processors 7 determine the predetermined number of segments (e.g., all five or at least three out of five) is each not less than or equal to the maximum limit threshold, the method 2300 ends. When the one or more processors 7 determine the predetermined number of segments is each less than or equal to the maximum limit threshold, the method 2300 continues to step 2344.

At step 2344, the computer executable instructions cause the one or more processors 7 to determine whether the largest (e.g., highest amplitude) magnitude in the 0.5-4.0 Hz range of the time to frequency transformed (e.g., Fast Fourier Transform) signal is both greater than a threshold Y (e.g., 20) and less than or equal to a threshold Z (e.g., 50.0). When the one or more processors 7 determine the largest magnitude in the 0.5-4.0 Hz range is not both greater than the threshold Y and less than or equal to the threshold Z, the method 2300 ends. The one or more processors 7 determine the compression garment 10 is in a wrapped configuration 2346 around a limb of a wearer of the garment when the one or more processors 7 determine the largest magnitude in the 0.5-4.0 Hz range is both greater than the threshold Y and less than or equal to the threshold Z. In an embodiment, the computer executable instructions cause the one or more processors 7 to declare the compression garment 10 is in a wrapped configuration (e.g., the wearer is wearing the compression garment) when the Boolean result of step 2336 is logical true AND the result of step 2338 is logical true AND the result of step 2340 is logical true AND the result of step 2342 is logical true AND the result of step 2344 is logical true. Alternatively, the computer executable instructions cause the one or more processors 7 to declare the compression garment 10 is in a wrapped configuration when the Boolean result of step 2336 is logical true AND the result of step 2340 is logical true AND the result of step 2344 is logical true.

After determining the compression garment 10 is in the wrapped configuration 2346, the method 2300 continues to step 2348 in which the computer executable instructions cause the one or more processors 7 to increment a compliance time before ending the method 2300.

While certain embodiments have been described, other embodiments are additionally or alternatively possible.

While compression systems have been described as being used with thigh length compression sleeves, it should be understood that the compression systems can additionally or alternatively be used with other types of compression garments. For example, the compression systems can be used with knee-length compression sleeves and/or with sleeves having a different number of bladders configured to be disposed over different areas of the wearer's body.

Embodiments can be implemented in digital electronic circuitry, or in computer hardware, firmware, software, or in combinations thereof. The controller of the compression system can be implemented in a computer program product tangibly embodied or stored in a machine-readable storage device for execution by a programmable processor; and method actions can be performed by a programmable processor executing a program of instructions to perform functions of the controller of the compression system by operating on input data and generating output. The controller of the compression system can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD ROM disks. Any of the foregoing can be supplemented by, or incorporated in, ASICs (application-specific integrated circuits) or FPGAs (field programmable logic arrays).

A number of embodiments have been described. Nevertheless, it will be understood that various modifications may be made without departing from the spirit and scope of the disclosure. For example, while a controller with a single pressure sensor has been described, additional pressure sensors (e.g., one for each inflatable bladder) can also be used without departing from the scope of the present disclosure. Accordingly, other embodiments are within the scope of the following claims.

What is claimed is:

1. A compression device controller for monitoring the compliance of a user with respect to wearing a compression device, the controller comprising:
at least one computer readable storage medium configured for storing one or more monitored parameters;
one or more processors coupled to the at least one computer readable storage medium; and
computer-executable instructions embodied on the at least one computer readable storage medium, the computer-executable instructions including instructions for causing the one or more processors to:
direct a flow of fluid from a pressurized fluid flow source to inflate and deflate at least one inflatable bladder of a compression garment configured to be wrapped around a limb of a wearer of the garment;
receive first pressure signals indicative of fluid pressure in the at least one inflatable bladder from a pressure sensor communicatively coupled thereto during at least one of inflation and deflation of the at least one inflatable bladder in a first compression cycle;
receive second pressure signals indicative of fluid pressure in the at least one inflatable bladder from the pressure sensor communicatively coupled thereto during at least one of inflation and deflation of the at least one inflatable bladder in a second compression cycle;
process the received first and second pressure signals;
detect a variance between the first pressure signals and the second pressure signals, the variance indicative of a change in condition of the compression garment; and
change a state of at least one of the monitored parameters in the at least one computer readable storage medium in response to detecting the variance, wherein the changed state of the monitored parameter is representative of the change in condition of the compression garment;
wherein the changed state of the monitored parameter is selected from a group consisting of the garment being wrapped around the limb of the wearer of the garment, and the garment not being wrapped around the limb of the wearer of the garment.

2. The compression device controller of claim 1, wherein the instructions for causing the one or more processors to change the state of at least one of the monitored parameters include instructions to one of increment a compliance timer and pause the compliance timer.

3. The compression device controller of claim 1, the computer executable instructions including instructions for causing the one or more processors to:
in response to the detected variance, verify the change in condition of the compression garment using at least one confirmatory analysis over subsequent cycles of inflation and deflation of the at least one inflatable bladder; and
based at least in part on the results of the at least one confirmatory analysis, change the state of the monitored parameter,
wherein changing the state of the monitored parameter comprises one of ceasing to increment a timer representative of the time the wearer is in compliance with the compression therapy regimen and starting to increment the timer.

4. The compression device controller of claim 1, the computer-executable instructions including instructions for causing the one or more processors to actuate a vent valve to maintain a non-therapeutic pressure in the at least one bladder.

5. The compression device controller of claim 1, wherein the variance is an oscillating amplitude as a function of time representative of a pulse of the wearer of the compression garment.

6. The compression device controller of claim 5, wherein the instructions to receive the first and second pressure signals indicative of fluid pressure in the at least one inflatable bladder include instructions to receive the first and second pressure signals indicative of fluid pressure while the at least one inflatable bladder is inflated to a non-therapeutic pressure.

7. The compression device controller of claim 5, wherein the instructions to process the received first and second pressure signals include instructions to:
band-pass filter the received first and second pressure signals to extract frequencies of 0.5 Hz to about 5 Hz;
low-pass filter the band-pass filtered signals at a frequency of about 5 Hz or under;
time-slice the low-pass filtered signals into a plurality of sample groups; and
detect an anomaly comprising at least a portion of the low-pass filtered signals within one or more of the plurality of sample groups by calculating a standard deviation of the plurality of sample groups as a whole and calculating a standard deviation of each sample group.

8. The compression device controller of claim 7, wherein the instructions to process the received first and second pressure signals include instructions to detect peaks in the low-pass filtered signals in a frequency range of 0.5 Hz to about 3.5 Hz.

9. The compression device controller of claim 1, wherein the at least one computer readable storage medium includes at least two computer readable storage mediums.

10. The compression device controller of claim 9, wherein the at least one computer readable storage medium comprises a memory.

11. A computer-implemented method comprising:
controlling, by computer-executable instructions executing on one or more processors, a pressurized fluid flow source through a cycle of operation in which at least one inflatable bladder of a compression garment configured to be wrapped around a limb of a patient is inflated and deflated;
receiving, by the one or more processors executing instructions therefor, first pressure signals indicative of fluid pressure in the at least one inflatable bladder from a pressure sensor communicatively coupled thereto during at least one of inflation and deflation of the at least one inflatable bladder in a first compression cycle;
receiving, by the one or more processors executing instructions therefor, second pressure signals indicative of fluid pressure in the at least one inflatable bladder from the pressure sensor communicatively coupled thereto during at least one of inflation and deflation of the at least one inflatable bladder in a second compression cycle;
detecting, by computer-executable instructions executing on the one or more processors, a variance between the first pressure signals and the second pressure signals, the variance in the received pressure signals indicative of a change in condition of the compression garment during the inflation and deflation of the at least one inflatable bladder; and
changing, by computer-executable instructions executing on the one or more processors, a state of at least one monitored parameter stored in a memory device in response to detecting the variance, wherein the memory device is coupled to the one or more processors, and wherein the changed state of the monitored parameter is representative of a change in condition of the compression garment;

wherein the changed state of the monitored parameter is selected from a group consisting of the garment being wrapped around the limb of the wearer of the garment, and the garment not being wrapped around the limb of the wearer of the garment.

12. The method of claim 11, wherein changing the state of the at least one of the monitored parameters comprises at least one of incrementing and pausing a compliance timer.

13. The method of claim 11, further comprising:
verifying, by computer executable instructions executing on the one or more processors, the change in condition of the compression garment using at least one confirmatory analysis over subsequent cycles of inflation and deflation of the at least one inflatable bladder, wherein said verifying is performed in response to the detected variance; and
changing, by the computer-executable instructions executing on the one or more processors, the state of the monitored parameter based at least in part on the results of the at least one confirmatory analysis.

14. The method of claim 11, wherein the variance is one of a pressure rise and a pressure impulse, the method further comprising indicating, by computer executable instructions executing on the one or more processors, whether the compression garment is worn by the patient.

15. The method of claim 14, further comprising actuating, by the one or more processors executing instructions therefor, a vent valve to maintain a non-therapeutic pressure in the at least one inflatable bladder.

16. The method of claim 11, wherein the variance is an oscillating amplitude as a function of time representative of a pulse of the patient.

17. The method of claim 16, wherein said detecting variance in the received first and second pressure signals comprises:
band-pass filtering, by the computer-executable instructions executing on the one or more processors, the received first and second pressure signals to extract frequencies of 0.5 Hz to about 5 Hz;
low-pass filtering, by the computer-executable instructions executing on the one or more processors, the band-pass filtered signals at a frequency of about 5 Hz or under;
time-slicing, by the computer-executable instructions executing on the one or more processors, the low-pass filtered signals into a plurality of sample groups;
detecting, by the computer-executable instructions executing on the one or more processors, an anomaly comprising at least a portion of the low-pass filtered signals within one or more of the plurality of sample groups by calculating a standard deviation of the plurality of sample groups as a whole and calculating a standard deviation of each sample group; and
detecting, by the computer-executable instructions executing on the one or more processors, one or more peaks in the low-pass filtered signals in a frequency range of about 0.5 Hz to about 3.5 Hz.

18. The method of claim 16, wherein said receiving first and second pressure signals indicative of fluid pressure in the bladder comprises receiving the first and second pressure signals while the at least one inflatable bladder is inflated to a non-therapeutic pressure.

19. A system for monitoring the compliance of a user with respect to wearing a compression device, system comprising:
a compression garment including at least one inflatable and deflatable bladder, the compression garment securable about a limb of a wearer; and
a controller comprising:
at least one computer readable storage medium configured for storing one or more monitored parameters;
one or more processors coupled to the at least one computer readable storage medium; and
computer-executable instructions embodied on a computer readable storage medium, the computer-executable instructions including instructions for causing the one or more processors to:
direct a flow of fluid from a pressurized fluid flow source to inflate and deflate the bladder of the compression garment;
receive first pressure signals indicative of fluid pressure in the bladder from a pressure sensor communicatively coupled thereto during at least one of inflation and deflation of the at least one inflatable bladder in a first compression cycle;
receive second pressure signals indicative of fluid pressure in the at least one inflatable bladder from the pressure sensor communicatively coupled thereto during at least one of inflation and deflation of the at least one inflatable bladder in a second compression cycle;
process the received first and second pressure signals;
detect a variance between the first pressure signals and the second pressure signals, the variance indicative of a change in condition of the compression garment; and
change a state of at least one of the monitored parameters in the at least one first computer readable storage medium in response to detecting the variance, wherein the changed state of the monitored parameter is representative of the change in condition of the compression garment;
wherein the changed state of the monitored parameter is selected from a group consisting of the compression garment being secured around the limb of the wearer, and the compression garment not being secured around the limb of the wearer.

20. The system of claim 19, further comprising:
at least one valve,
wherein the at least one valve is in fluid communication with the pressurized fluid flow source and the bladder,
wherein the at least one valve is in electrical communication with the controller, and
wherein the computer-executable instructions include instructions for causing the one or more processors to actuate the at least one valve to control fluid communication between the pressurized fluid flow source and the bladder.

21. The system of claim 19, wherein the pressurized fluid flow source is in electrical communication with the controller, and wherein the computer-executable instructions include instructions for causing the one or more processors to adjust a speed of the pressurized fluid flow source based at least in part on the detected variance in the pressure signals.

22. The system of claim 19, wherein the at least one inflatable bladder extends around a circumference of the limb of the wearer when secured about the limb of the wearer.

* * * * *